United States Patent [19]

Baker, Jr. et al.

[11] Patent Number: 5,998,153
[45] Date of Patent: Dec. 7, 1999

[54] THYROID PEROXIDASE EPITOPIC REGIONS

[75] Inventors: James R. Baker, Jr.; Ronald J. Koenig, both of Ann Arbor, Mich.

[73] Assignee: The Regents of the University of Michigan, Ann Arbor, Mich.

[21] Appl. No.: 08/313,200

[22] PCT Filed: Apr. 22, 1993

[86] PCT No.: PCT/US93/03837

§ 371 Date: Nov. 8, 1994

§ 102(e) Date: Nov. 8, 1994

[87] PCT Pub. No.: WO93/23073

PCT Pub. Date: Nov. 25, 1993

Related U.S. Application Data

[63] Continuation-in-part of application No. 07/885,656, May 19, 1992, abandoned.

[51] Int. Cl.$^6$ ...................... G01N 33/564; G01N 33/573; A61K 38/43
[52] U.S. Cl. .................. 435/7.21; 435/7.4; 435/7.92; 435/192; 435/975; 436/506; 436/518; 436/536; 436/811; 530/326; 530/854; 930/240
[58] Field of Search ..................................... 435/7.4, 7.92, 435/975, 192, 7.21; 436/811, 506, 518, 536; 530/326, 395, 854; 930/240

[56] References Cited

FOREIGN PATENT DOCUMENTS 0421139  10/1991  European Pat. Off. .
WO 91/02061  2/1991  WIPO .

OTHER PUBLICATIONS

Weetman et al., "Autoimmune thyroid disease: Developments in our understanding" *Endocrinol. Rev.* (1984) 5:309–355.

Yokoyama et al., "Thyroid peroxidase and thyroid microsomal autoantibodies" *J. Clin. Endocrinol. Metab.* (1989) 68:766–773.

Saller et al., "Heterogeneity of autoantibodies against thyroid peroxidase in autoimmune thyroid disease: Evidence against antibodies directly inhibiting peroxidase activity as regulatory factors in thyroid hormone metabolism" *J. Clin. Endocrinol. Metab.* (1991) 72:188–195.

Kimura et al., "Human thyroid peroxidase: Complete cDNA and protein sequence, chromosome mapping, and identification of two alternately spliced mRNAs" *Proc. Natl. Acad. Sci. USA* (1987) 84:5555–5559.

Nagayama et al., "Characterization, by molecular cloning, of smaller forms of thyroid peroxidase messenger ribonucleic acid in human thyroid cells as alternatively spliced transcripts" *J. Clin. Endocrinol. Metab.* (1990) 71:384–390.

Zanelli et al., "Evidence for an alternate splicing in the thyroperoxidase messenger from patients with Graves' disease" *Biochem. Biophys. Res. Comm.* (1990) 170:735–741.

Elisei et al., "Demonstration of the existence of the alternatively spliced form of thyroid peroxidase in normal thyroid" *J. Clin. Endocrinol. Metab.* (1991) 72:700–702.

Foti et al., "Carbohydrate moieties in recombinant human thyroid peroxidase: Role in recognition by antithyroid peroxidase antibodies in Hashimoto's thyroiditis" *Endocrinology* (1990) 126:2983–2988.

Finke et al., "Evidence for the highly conformational nature of the epitope(s) on human thyroid peroxidase that are recognized by sera from patients with Hashimoto's thyroiditis" *J. Clin. Endocrinol. Metab.* (1990) 71:53–59.

Libert et al., "Thyroperoxidase, an auto–antigen with a mosaic structure made of nuclear and mitochondrial gene modules" *EMBO J.* (1987) 6:4193–4196.

Ludgate et al., "Antibodies to human thyroid peroxidase in autoimmune thyroid disease: Studies with a cloned recombinant complementary deoxyribonucleic acid epitope" *J. Clin. Endocrinol. Metab.* (1989) 68:1091–1096.

Elisei et al., "Studies with recombinant autoepitopes of thyroid peroxidase: Evidence suggesting an epitope shared between the thyroid and the gastric parietal cell" *Autoimmunity* (1990) 8:65–70.

Libert et al., "Thyroperoxidase, but not the thyrotropin receptor, contains sequential epitopes recognized by autoantibodies in recombinant peptides expressed in the pUEX vector" *J. Clin. Endocrinol. Metab.* (1991) 73:857–860.

Nakajima et al., "Structure–activity analysis of microsomal antigen/thyroid peroxidase" *Mol. Cell. Endocrinol.* (1987) 53:15–23.

Yokoyama et al., "Studies with purified human thyroid peroxidase and thyroid microsomal autoantibodies" *J. Clin. Endocrin. Metab.* (1990) 70:758–765.

Mazzaferri, "Thyroid cancer" *Part III: The Thyroid Gland* Chapter 43, pp. 319–331.

Cooper et al., "Follicular and Hürthle cell carcinoma of the thyroid" *Thyroid Carcinoma* (1990) 19:577–591.

Robbins et al., "Thyroid cancer: A lethal endocrine neoplasm" *Annals of Intern. Med.* (1991) 115:133–147.

Kramer et al., "Thyroid carcinoma" *Adv. Surg.* (1989) 22:195–224.

(List continued on next page.)

*Primary Examiner*—James C. Housel
*Assistant Examiner*—James L. Grun
*Attorney, Agent, or Firm*—Morrison & Foerster

[57] ABSTRACT

Specific epitopic regions of thyroid peroxidase (TPO), a thyroid specific membrane autoantigen, have been identified within amino acid residues 456 to 933, 517 to 630, and 633 to 933 of the protein (SEQ ID NO:1), with at least one distinct binding region within TPO located from amino acid residues 592 to 613 (SEQ ID NO:3). The identification and production of these localized epitopes/epitopic regions provide specific diagnostic reagents for autoimmune thyroid disease.

6 Claims, 21 Drawing Sheets

OTHER PUBLICATIONS

Barnes, "Effects of external irradiation on the thyroid gland in childhood" *Horm. Res.* (1988) 30:84–89.

Banga et al., "Prediction of domain organisation and secondary structure of thyroid peroxidase, a human autoantigen involved in destructive thyroiditis" *FEBS Letters* (1990) 266:133–141.

Kimura et al., "Human myeloperoxidase and thyroid peroxidase, two enzymes with separate and distinct physiological functions, are evolutionarily related members of the same gene family" *Proteins* (1988) 3:113–120.

Baker et al., "Development of a human monoclonal antibody from a Graves' disease patient that identifies a novel thyroid membrane antigen" *J. Immunol.* (1988) 140:2593–2599.

Block et al., "The treatment of papillary and follicular carcinoma of the thyroid" *Otolaryngol. Clin. North Am.* (1990) 23:403–411.

Watne et al., "Follicular carcinoma of the thyroid" *Seminars in Surgical Oncology* (1991) 7:87–91.

Bisi et al., "The prevalence of unsuspected thyroid pathology in 300 sequential autopsies, with special reference to the incidental carcinoma" *Cancer* (1989) 64:1888–1893.

Clark et al., "Thyroid cancer: The case for total thyroidectomy" *Eur. J. Cancer Clin. Oncol.* (1988) 24:305–313.

Mazzaferri, "Thyroid cancer and Graves' disease" *J. Clin. Endocrinol. Metab.* (1990) 70:826–829.

Paul et al., "Thyrotoxicosis caused by thyroid cancer" *Endocrinol. Metabol. Clinics of North America* (1990) 19:593–612.

Krenning et al., "Clinical and radio–diagnostic aspects in the evaluation of thyroid nodules with respect to thyroid cancer" *Eur. J. Cancer Clin. Oncol.* (1988) 24:299–304.

Sisson, "Medical treatment of benign and malignant thyroid tumors" *Endocrinol. Metabol. Clinics of North America* (1989) 18:359–387.

Mazzaferri, "Papillary thyroid carcinoma: Factors influencing prognosis and current therapy" *Seminars in Oncology* (1987) 14:315–332.

Khan et al., "Variable presentations of medullary carcinoma of the thyroid gland" *Ear, Nose and Throat Journal* (1989) 68:31–32, 34, 39–40.

Kvols et al., "Chemotherapy of endocrine malignancies: A review" *Seminars in Oncology* (1987) 14:343–353.

Pacini et al., "Thyroid autoantibodies in thyroid cancer: Incidence and relationship with tumour outcome" *Acta Endocrinologica* (1988) 119:373–380.

Filetti et al., "The role of thyroid–stimulating antibodies of Graves' disease in differentiated thyroid cancer" *New Eng. J. Med.* (1988) 318:753–759.

Belfiore et al., "Increased aggressiveness of thyroid cancer in patients with Graves' disease" *J. Clin. Endocrinol. Metab.* (1990) 70:830–835.

Bagnasco et al., "Phenotypic and functional analysis at the clonal level of infiltrating T lymphocytes in papillary carcinoma of the thyroid: Prevalence of cytolytic T cells with natural killer–like or lymphokine–activated killer activity" *J. Clin. Endocrinol. Metab.* (1989) 69:832–836.

Bagnasco et al., "Expression of intercellular adhesion molecule–1 (ICAM–1) on thyroid epithelial cells in Hashimoto's thyroiditis but not in Graves' disease or papillary thyroid cancer" *Clin. Exp. Immunol.* (1991) 83:309–313.

Liaw et al., "Impaired cell–mediated immunity function in thyroid cancer" *Cancer* (1980) 46:285–288.

Aoki et al., "Lymphocyte blastogenic response to human thyroglobulin in Graves' disease, Hashimoto's thyroiditis, and metastatic thyroid cancer" *Clin. Exp. Immunol.* (1979) 38:523–530.

Boros et al., "Natural killer activity in thyroid cancer patients" *Haematologia* (1987) 20:189–193.

Sack et al., "Thyrocyte specific killer cell activity is decreased in patients with thyroid carcinoma" *Cancer* (1987) 59:1914–1917.

Durie et al., "High–risk thyroid cancer. Prolonged survival with early multimodality therapy" *Cancer Clin. Trials* (1981) 4:67–73.

Juhasz et al., "Immunogenetic and immunologic studies of differentiated thyroid cancer" *Cancer* (1989) 63:1318–1326.

Juhasz et al., "Interaction of IgG heavy–chain allotypes (GM) and HLA in conferring susceptibility to thyroid carcinoma" *Clin. Endocrinol.* (1986) 25:17–21.

MacKenzie et al., "Intrathyroidal T cell clones from patients with autoimmune thyroid disease" *J. Clin. Endocrinol. Metab.*(1987) 64:818–824.

Okayasu, "Transfer of experimental autoimmune thyroiditis to normal syngeneic mice by injection of mouse thyroglobulin–sensitized T lymphocytes after activation with concanavalin A" *Clin. Immunol. Immunopathol.* (1985) 36:101–109.

Charreire et al., "Syngeneic sensitization of mouse lymphocytes on monolayers of thyroid epithelial cells. III. Induction of thyroiditis by thyroid–sensitized T lymphoblasts" *Eur. J. Immunol.* (1982) 12:421–425.

Romball et al., "Transfer of experimental autoimmune thyroditis with T cell clones" *J. Immunol.* (1987) 138:1092–1098.

Maron et al., "T lymphocyte line specific for thyroglobulin produces or vaccinates against autoimmune thyroiditis in mice" *J. Immunol.* (1983) 131:2316–2322.

Creemers et al., "Experimental autoimmune thyroiditis. In vitro cytotoxic effects of T lymphocytes on thyroid monolayers" *J. Exp. Med.* (1983) 157:559–571.

Canonica et al., "Proliferation of T8–positive cytolytic T lymphocytes in response to thyroglobulin in human autoimmune thyroiditis: Analysis of cell interactions and culture requirements" *Clin. Immunol. Immunopathol.* (1985) 36:40–48.

Mauras et al., "Hasimoto thyroiditis associated with thyroid cancer in adolescent patients" *J. Pediatrics* (1985) 106:895–898.

Maceri et al., "Autoimmune thyroiditis: Pathophysiology and relationship to thyroid cancer" *Laryngoscope 96* (Jan. 1986) pp. 82–86.

Høie et al., "Surgery in papillary thyroid carcinoma: A review of 730 patients" *J. Surgical Oncology* (1988) 37:147–151.

Amino et al., "Immunologic aspects of human thyroid cancer" *Cancer* (1975) 36:963–973.

Lo Gerfo et al., "Immunotherapy of thyroid cancer by induction of autoimmune thyroiditis" *Surgery* (1983) 94:959–965.

Charreire, "Immune mechanisms in autoimmune thyroiditis" *Advances in Immunol.* (1989) 46:263–334.

Weetman, "Thyroid peroxidase as an antigen in autoimmune thyroiditis" *Clin. Exp. Immunol.* (1990) 80:1–3.

Bech et al., "Thyroid adenylate cyclase stimulating immunoglobulins in thyroid diseases" *Clin. Endocrinol.* (1979) 11:47–58.

Dong et al., "Cloning and sequencing of a novel 64–kDa autoantigen recognized by patients with autoimmune thyroid disease" *J. Clin. Endocrinol. Metab.* (1991) 72:1375–1381.

Parmentier et al., "Molecular cloning of the thyrotropin receptor" *Science* (1989) 246:1620–1622.

Wadsworth et al., "An insertion in the human thyrotropin receptor critical for high affinity hormone binding" *Science* (1990) 249:1423–1425.

Burman et al., "Immune mechanisms in Graves' disease" *Endocrine Reviews* (1985) 6:183–232.

Wick et al., "The obese strain of chickens: An animal model with spontaneous autoimmune thyroiditis" *Advances in Immunol.* (1989) 47:433–500.

Krco et al., "Immunogenetic aspects of human thyroglobulin–reactive T cell lines and hybridomas" *J. Immunogenetics* (1990) 17:361–370.

Sundick, "Iodine in autoimmune thyroiditis" *Immunol. Ser.* (1990) 52:213–228.

Fragu et al., "Human thyroid peroxidase activity in benign and malign thyroid disorders" *J. Clin. Endocrin. Metab.* (1977) 45:1089–1096.

De Micco et al., "Immunohistochemical study of thyroid peroxidase in normal, hyperplastic, and neoplastic human thyroid tissues" *Cancer* (1991) 67:3036–3041.

Christov et al., "Cytochemical localization of peroxidase activity in normal, proliferating and neoplastic thyroid tissues of rats. An ultrastructural study" *Acta Histochem. Bd.* (1977) 58:275–289.

Roman et al., "Induction of microsomal antigen and comparison with histologic localization of HLA–DR in Graves' thyroid tissue" *Autoimmunity* (1989) 2:253–263.

Kotani et al., "Experimental murine thyroiditis induced by porcine thyroid peroxidase and its transfer by the antigen–specific T cell line" *Clin. Exp. Immunol.* (1990) 80:11–18.

Studier et al., "Use of T7 RNA polymerase to direct expression of cloned genes" *Meth. Enzymol.* (1990) 185:60–89.

Portmann et al., "Anti–thyroid peroxidase antibody in patients with autoimmune thyroid disease: Possible identity with anti–microsomal antibody" *J. Clin. Endocrinol. Metab.* (1985) 61:1001–1003.

Maastricht et al., "Identification of localized autoantibody epitopes in thyroid peroxidase" *J. Clin. Endocrinol. Metab.* (1992) 75:121–126.

Spaulding, "Age and the thyroid" *Endocrinol. Metabol. Clinics* (1987) 16:1013–1025.

Flick et al., "Comparison of in vitro cell cytotoxic assays for tumor necrosis factor" *J. Immunol. Meth.* (1984) 68:167–175.

Weetman et al., "Enzyme–linked immunoassay of monoclonal and serum microsomal autoantibodies" *Clin. Chim. Acta* (1983) 138:237–244.

Fisfalen et al., "Microsomal antigen–reactive lymphocyte lines and clones derived from thyroid tissue of patients with Graves' disease" *J. Clin. Endocrinol. Metab.* (1988) 66:776–784.

Hamada et al., "Identification of a thyroid microsomal antigen by Western blot and immunoprecipitation" *J. Clin. Endocrinol. Metab.* (1985) 61:120–128.

Rapoport et al., "Clinical experience with a human thyroid cell bioassay for thyroid–stimulating immunoglobulin" *J. Clin. Endocrinol. Metab.* (1984) 58:332–338.

Ledent et al., "Thyroid adenocarcinomas secondary to tissue–specific expression of Simian virus–40 large T–antigen in transgenic mice" *Endocrinology* (1991) 129:1391–1401.

Ozaki et al., "Cloned protein antigen–specific, Ia–restricted T cells with both helper and cytolytic activities: Mechanisms of activation and killing" *Cell. Immunol.* (1987) 105:301–316.

Higgs et al., "A novel pathway of human T lymphocyte activation. Identification by a monoclonal antibody generated against rheumatoid synovial T cell line" *J. Immunol.* (1988) 140:3758–3765.

Holoshitz et al., "Arthritis induced in rats by cloned T. lymphocytes responsive to mycobacteria but not to Collagen Type II" *J. Clin. Invest.* (1984) 73:211–215.

Goronzy et al., "Cloning of Human alloreactive T. cells" *Meth. Enzymol.* (1987) 150:333–341.

Lanier et al., "Presence of Ti(WT31) negative T lymphocytes in normal blood and thymus" *Nature* (1986) 324:268–270.

Bruderer et al., "Characterization of the Group I and Group II antibody response against PC–KLH in normal and T15 idiotype–suppressed BACL/c mice" *Immunol.* (1988) 64:385–390.

Mitsuya et al., "Generation of an HLA–restricted cytotoxic T cell line reactive against cultured tumor cells from a patient infected with human T cell leukemia/lymphoma virus" *J. Exper. Med.* (1983) 158:994–999.

Anichini et al., "Cytotoxic T lymphocyte clones from peripheral blood and from tumor site detect intratumor heterogeneity of melanoma cells. Analysis of specificity and mechanisms of interaction" *J. Immunol.* (1989) 142:3692–3701.

Germain, "The ins and outs of antigen processing and presentation" *Nature* (1986) 322:687–689.

Berzofsky et al., "Antigen processing for presentation to T lymphocytes: Function, mechanisms, and implications for the T–cell repertoire" *Immunol. Reviews* (1988) 106:5–31.

Grey et al., "How T cells see antigen" *Scientific American* (Nov. 1989) pp. 56–64.

Wrann et al., "T cell suppressor factor from human glioblastoma cells is a 12.5–kd protein closely related to transforming growth factor–$\beta$" *EMBO J.* (1987) 6:1633–1636.

Ranges et al., "Inhibition of cytotoxic T cell development by transforming growth factor $\beta$ and reversal by recombinant tumor necrosis factor $\alpha$" *J. Exp. Med.* (1987) 166:991–998.

Townsend et al., "The epitopes of influenza nucleoprotein recognized by cytotoxic T lymphocytes can be defined with short synthetic peptides" *Cell* (1986) 44:959–968.

Bjorkman et al., "Structure of the human class I histocompatibility antigen, HLA–A2" *Nature* (1987) 329:506–512.

Schumacher et al., "Direct binding of peptide to empty MHC class I molecules on intact cells and in vitro" *Cell* (1990) 62:563–567.

Kozlowski et al., "Excess $\beta_2$ microglobulin promoting functional peptide association with purified soluble class I MHC molecules" *Nature* (1991) 349:74–77.

Wilson et al., "Correction of CD18–deficient lymphocytes by retrovirus–mediated gene transfer" *Science* (1990) 248:1413–1416.

Shigekawa et al., "Electroporation of eukaryotes and prokaryotes: A general approach to the introduction of macromolecules into cells" *BioTechniques* (1988) 6:742–751.

Ljunggren et al., "Empty MHC class I molecules come out in the cold" *Nature* (1990) 346:476–480.

Sack et al., "Killer cell activity and antibody–dependent cell–mediated cytotoxicity are normal in Hashimoto's disease" *J. Clin. Endocrinol. Metab.* (1986) 62:1059–1064.

Ida et al., "An enzyme–linked immunosorbent assay for the measurement of human interleukin–6" *J. Immunol. Meth.* (1990) 133:279–284.

Okayama et al., "High efficiency cloning of full–length cDNA" *Mol. Cell. Biol.* (1982) 2:161–170.

Vitti et al., "Characterization of the optimal stimulatory effects of Graves' monoclonal and serum immunoglobulin G on adenosine 3',5'–monophosphate production in FRTL–5 thyroid cells: A potential clinical assay" *J. Endocrinol. Metab.* (1983) 57:782–791.

Valente et al., "Antibodies that promote thyroid growth. A distinct population of thyroid–stimulating autoantibodies" *New Eng. J. Med.* (1983) 309:1028–1034.

Lucas et al., "Generation of antibodies and assays for transforming growth factor β" *Meth. Enzymol.* (1991) 198:303–316.

Feldman et al., "TSH receptor antibody induction of thyroglobulin release from human thyroid cell monolayers" *Clin. Endocrinol.* (1986) 25:45–53.

Tominaga et al., "Interleukin 6 inhibits human thyroid peroxidase gene expression" *Acta Endocrinol.* (1991) 124:290–294.

Zanelli et al., "Use of recombinant epitopes to study the heterogeneous nature of the autoantibodies against thyroid peroxidase in autoimmune thyroid disease" *Clin. Exp. Immunol.* (1992) 87:80–86.

Doble et al., Autoantibodies to the thyroid microsomal/thyroid peroxidase antigen are polyclonal and directd to several distinct antigenic sites *Immunol.* (1988) 64:23–29.

Laver et al., "Epitopes on protein antigens: Misconceptions and realities" *Cell* (1990) 61:553–556.

Hirota et al., "Thyroid function and histology in forty–five patients with hyperthyroid Graves' disease in clinical remission more than ten years after thionamide drug treatment" *J. Clin. Endocrinol. Metab.* (1986) 62:165–169.

Baker, "Immunogenetics, the HLA system, and endocrine disease" *Part XI: Heritable Abnormalities of Endocrinology and Metabolism* Chapter 189, pp. 1401–1404.

Geysen et al., "Strategies for epitope analysis using peptide synthesis" *J. Immunol. Metabol.* (1987) 102:259–274.

Kawakami et al., "Interleukin 4 promotes the growth of tumor–infiltrating lymphocytes cytotoxic for human autologous melanoma" *J. Exper. Med.* (1988) 168:2183–2191.

Klein, "Production and characterization of antibodies" *Natural History of the Major Histocompatibility Complex* (1986) John Wiley & Sons, Inc., New York, p. 235.

Kotani et al., "Detection of autoantibodies to thyroid peroxidase in autoimmune thyroid diseases by micro–ELISA and immunoblotting" *J. Clin. Endocrinol. Metab.* (1986) 62:928–933.

Rapoport et al., "Studies on the cyclic AMP response to thyroid stimulating immunoglobulin (TSI) and thyrotropin (TSH) in human thyroid cell monolayers" *TSI Bioassay* (1982) pp. 1159–1167.

Pharmacia P–L Biochemicals, *Molecular and Cellular Biology Catalogue* (1992/1993) Pharmacia Biosystems, Inc., Milwaukee, Wisconsin, Chapter 8, pp. 144–160.

THYROID PEROXIDASE EPITOPIC REGIONS

RELATED APPLICATIONS

This is a continuation-in-part of U.S. application Ser. No. 07/885,656, entitled "Thyroid Peroxidase Epitopic Regions," filed May 19, 1992, now abandoned, herein incorporated by reference.

GENBANK INFORMATION

Thyroid peroxidase sequence has been previously accorded GenBank Accession No. J02969.

FIELD OF THE INVENTION

The present invention relates generally to thyroid peroxidase and, more specifically, to autoantibody epitopic regions of thyroid peroxidase and diagnostic and therapeutic applications thereof.

BACKGROUND OF THE INVENTION

Thyroid peroxidase (TPO) is the major thyroid-specific membrane autoantigen implicated in Hashimoto's thyroiditis, an autoimmune disease characterized by intense lymphocytic thyroiditis resulting in the destruction of the thyroid. Weetman, A. P. et al, *Endocrinol. Rev.* 5:309–355 (1984). TPO's role in autoimmune disease and the precise localization of autoantibody binding has, however, been a subject of much debate. For example, there has been controversy as to whether autoantibodies inhibit thyroid peroxidase activity, thereby contributing to thyroid dysfunction in autoimmune thyroid disease. See Yokoyama, N. et al., *J. Clin. Endocrinol. Metab.* 68:766–773 (1989); Saller, B. et al., *J. Clin. Endocrinol. Metab.* 72:188–195 (1991). Reports on variations in the structure of TPO have suggested alternative mRNA splicing as a source of antigenicity. Kimura, S. et al., *PNAS (USA)* 84:5555–5559 (1987); Nagayama, Y. et al., *J. Clin. Endocrinol. Metab.* 71:384–390 (1990); Zanelli, E. et al., *Biochem. Biophys. Res. Commun.* 170:735–741 (1990). The appearance of these alternative transcripts in normal thyroid glands has, however, brought the relationship of alternative splicing and autoimmunity into question. Elisei, R. et al., *J. Clin. Endocrinol. Metab.*, 72:700–702 (1991). It also now appears that carbohydrate structures are not involved in TPO antigenicity. Foti, D. et al., *Endocrinol.* 126:2983–2988 (1990).

Recent reports on the number and type of autoantibody epitopes found in human TPO have been conflicting. One group has suggested that TPO autoantibodies bind only to conformation epitopes and that no localized epitopes exist. Finke, R. et al., *J. Clin. Endocrinol. Metab.* 71:53–59 (1990). Given that this group demonstrated binding to recombinant TPO produced in CHO cells, but was unable to show binding to whole recombinant TPO in the bacterial expression system employed, the failure to identify localized epitopes could have resulted from a problem with the expression of intact TPO in bacteria. In contrast, another group has reported the identification of localized autoantibody of TPO epitopes using in vitro translated TPO cDNA clones. Libert, F. et al., *EMBO J.* 6:4193–4196 (1987); Ludgate, M. et al., *J. Clin. Endocrinol. Metab.* 68:1091–1096 (1989). Using sera from Hashimoto's disease patients, localized autoantibody binding was identified between amino acids 590 and 675 of the TPO coding sequence. Id. While initially identifying only a single antibody binding site in this region, more recent publications of this group indicated the presence of multiple antibody binding sites in the carboxyl half of the TPO molecule. Elisei, R. et al., *Autoimmunity* 8:65–70 (1990); Libert, F. et al., *J. Clin. Endocrinol. Metab.* 73:857–560 (1991). Several other studies using trypsin digests of purified native TPO have also suggested the presence of multiple autoantibody epitopes, including some which appear to be conformational and require disulfide bonds. Nakajima, Y. et al., *Mol. Cell Endocrinol.* 53:15–23 (1987); Yokoyama, N. et al., *J. Clin. Endocrinol. Metab.* 70:758–765 (1990). However, there has been no consensus on the exact number and type of epitopes present in TPO.

The identification of autoantibody thyroid-specific epitopes is important to the understanding and diagnosis of autoimmune thyroid disease and in developing effective immunotherapeutic strategies against thyroid disease and cancer. The identification of specific localized TPO epitopic regions would provide a powerful diagnostic tool for autoimmune diseases such as Hashimoto's to distinguish it from other thyroid conditions. The identification and ability to produce sequences encompassing specific TPO autoantibody epitopes would also be instrumental in developing immunotherapeutic strategies against autoimmune thyroid disease and thyroid cancer.

The development of new therapeutic approaches to treating thyroid cancer is of particular importance. Thyroid cancer is diagnosed in 10,000 individuals in the United States each year. Mazzaferri, E. L. "Thyroid Cancer," Ch. 43:319–331 (Becker, K. L. ed.) *Principles and Practice of Endocrinology and Metabolism,* J. B. Lippencott (Philadelphia Pa. 1990); Cooper, D. S. et al., *Encrinol. Metab. Clin. North Am.* 19(3):577–591 (1990). While modern techniques have led to early diagnosis and treatment, approximately 10% of thyroid cancer patients develop terminal metastatic disease. Robbins, J. et al., *Ann. Intern. Med.* 115(2):133–147 (1991). Thyroid cancer presents an important public health problem in that it most commonly occurs in otherwise healthy and productive individuals in the third and fourth decades of life. Mazzaferri, E. L. "Thyroid Cancer," Ch. 43:319–331 (Becker, K. L. ed.) *Principles and Practice of Endocrinology and Metabolism,* J. B. Lippencott (Philadelphia Pa. 1990). It is also an extremely important health problem for women, as it occurs three times as often in women than in men. Kramer, J. B. et al., *Adv. Surg.* 22:195–224 (1989). The disease can also be seen in children, especially after radiation exposure. Barnes, N. D., *Horm. Res.* 30:84–89 (1988). While less common in the elderly, thyroid cancer has a much worse prognosis in this population. Mazzaferri, "Thyroid Cancer," Ch. 43:319–313 (Becker K. L., ed.) *Principles and Practice of Endocrinology and Metabolism* (J. B. Lippencott, Philadelphia Pa. 1990); Cooper, D. S. et al., *Endocrinol. Metab. Clin. North Am.* 19(3):577–591 (1990).

Current therapeutic approaches for the two most prevalent types of thyroid cancer, papillary and follicular carcinoma, involve partial or complete thyroidectomy, often in conjunction with radioactive iodine therapy. However, a substantial number of patients show no response to conventional treatment. For example, some thyroid tumors do not respond to radioactive iodine treatment because the carcinoma is not sufficiently differentiated to concentrate lethal quantities of radioactivity. Additionally, the side effects attending conventional chemotherapeutic and radiation therapy have a serious adverse impact on patient health and well-being.

More sensitive diagnostic and alternative therapeutic strategies against thyroid disease and cancer would thus be desirable. Such strategies can be provided with the identification of specific thyroid peroxidase epitopic regions.

SUMMARY OF THE INVENTION

Specific epitopic regions of thyroid peroxidase (TPO), a thyroid-specific cell membrane enzyme and the autoantibody target in autoimmune thyroid disease, have been identified. The epitopic regions reside from amino acid 456 to 933 (SEQ ID NO:1), with two distinct regions located from amino acid 517 to 630 (SEQ ID NO:1) and from amino acid 633 to 933 (SEQ ID NO:1), the former region having at least one distinct binding region therewithin located from amino acid 592 to 613 (SEQ ID NO:1) inclusive. The latter region also has at least two distinct binding regions therewithin, located from amino acid 633 to 768 (SEQ ID NO:1) and from amino acid 768 to 933 (SEQ ID NO:1). The specific epitopic regions provide a sensitive diagnostic reagent for autoimmune thyroid disease and, as thyroid-specific structures, can be used for immunotherapy of thyroid disease and cancer. Nucleic acid sequences coding for TPO epitopic regions, and sequences complementary thereto, are also contemplated as being within the scope of the present invention.

Since TPO is expressed in most thyroid cancers, patients can be immunized with TPO epitope contained within these regions to induce or augment the immune response to TPO, specifically targeting the TPO-bearing cancer cells. Adoptive immunotherapy involving the harvesting of immune cells from the thyroid, their in vitro stimulation by TPO epitope and reimplantation into the patient is also now feasible. Monoclonal antibodies specific for TPO epitope/epitopic region can also be administered for passive immunotherapy.

Autoimmune thyroid disease, such as Hashimoto's thyroiditis, can also be treated by blocking or competing with autoantibody binding to native TPO in the thyroid. More sensitive assays utilizing TPO epitopic binding to screen for the presence of autoantibody are also useful in diagnosing patients with Hashimoto's disease and in distinguishing Hashimoto's from other thyroid disorders.

Other features and advantages of the present invention will become apparent from the following description and appended claims, taken in conjunction with the accompanying drawings.

DETAILED DESCRIPTION OF THE PREFERRED EMBODIMENTS

Identification of TPO Epitopic Regions

Figure 1A:
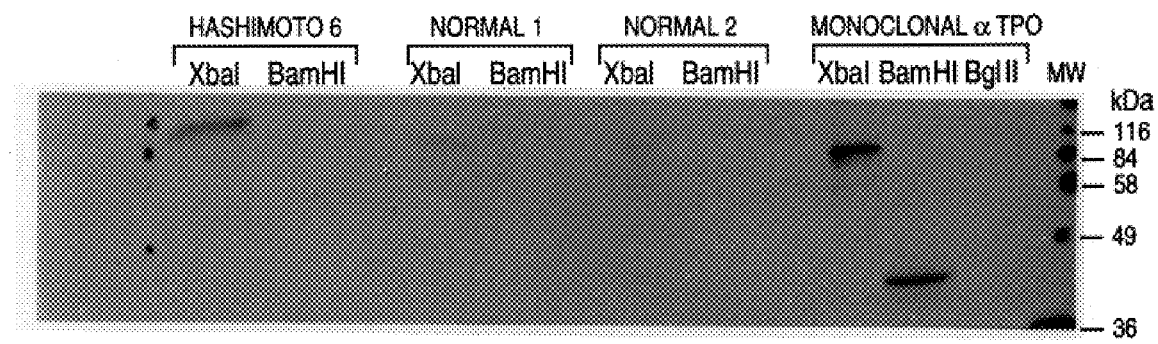
FIGS. 1A and 1B present immunoprecipitation studies of recombinant thyroid peroxidase (TPO) fragments produced from different length cDNA templates.

As detailed in Specific Example I, several distinct and localized areas of thyroid peroxidase (TPO) have been found to bind autoantibodies of patients with Hashimoto's disease. These autoantibody binding regions were localized from the TPO molecule's C-terminus (AA 933) to amino acid 455 (SEQ ID NO:1), and were recognized by over 90% of the Hashimoto's patients tested. At least one autoantibody epitopic region was located from amino acid 456 to 631 (SEQ ID NO:1), more specifically from amino acid 517 to 630 (SEQ ID NO:1), and another was located from amino acid 633 to 933 (SEQ ID NO:1), the former region having at least one distinct binding region therewithin located from amino acid 592 to 613 (SEQ ID NO:1). (See Specific Example V) Further studies indicated that the latter region also included at least two binding or epitopic regions from amino acid 633 to 768 (SEQ ID NO:1) and from amino acid 768 to 933 (SEQ ID NO:1). The absence of local autoantibody binding in the first 455 amino acids of TPO (SEQ ID NO:1) is remarkable, although the possibility that autoantibodies bind to conformational determinants in TPO involving areas both N-terminal and C-terminal to amino acid 456 cannot be excluded.

Despite difficulties in expressing full-length TPO in *E. coli*, the results of the immunoprecipitation studies described below permitted focusing on the C-terminal half of this antigen. It was postulated that, due to its smaller size, a construct encoding the C-terminal half of TPO would be more likely to be successfully expressed in bacteria. To further optimize expression, an expression system with a vector (pMAL, New England BioLabs) not previously used in thyroid peroxidase studies was used to produce a bacterial fusion protein, maltose binding protein (MBP). The construct MBP-TPO (AA 456–933) (SEQ ID NO:1) was able to produce full-length fusion protein and many smaller MBP fusion proteins were also produced. The expression of the smaller C-terminal truncated fusion proteins supplemented the Western blot analysis, since the shorter fragments potentially contained fewer autoantibody recognition sites. This appeared to be the case, since some of the smaller fragments reacted with only a subset of the Hashimoto's sera. These results provided evidence that multiple epitopes are present in TPO, and that patients' sera differ in their reactivity to these epitopes.

Several fragments of human TPO recognized by human autoantibodies from a majority of Hashimoto's patients were thus identified. As noted above, these fragments were located in the carboxyl half of the molecule, after amino acid 455, and were recognized in recombinant TPO proteins. At least one autoantibody epitope was located in the region from amino acid 517 to 630 (SEQ ID NO:1), and at least two additional areas of binding were identified within the region from amino acid 633 to 933 (SEQ ID NO:1), more specifically from amino acid 633 to 768 (SEQ ID NO:1) and from amino acid 768 to 933 (SEQ ID NO:1), the former region having at least one distinct binding region therewithin located from amino acid 592 to 613 (SEQ ID NO:1). Autoantibody binding to native TPO could be competitively inhibited by preincubation with these fragments and it appeared there was heterogeneity in the fragments recognized by different Hashimoto's patients.

The TPO fragments recognized by the sera of Hashimoto's patients appear localized to the regions encoded by exons 8, 9, 10, and possibly 11. Banga, J. P. et al., *FEBS Lett.* 266:133–141 (1990). This region has homology with the cytochrome oxidase gene and is potentially involved in TPO enzymatic activity, specifically the distal heme-iron binding region. Kimura, S. et al., *Proteins* 3:113–120 (1988). This suggests a potential relationship between autoantibody binding and TPO function. The TPO fragment where autoantibody binding is localized is also a region where alternative RNA splicing reportedly results in an internal deletion of amino acids 533 to 589 (SEQ ID NO:1). Kimura S. et al., *PNAS (USA)* 84:5555–5559 (1987). The significance of this is not evident, however, as other investigators have found alternative splicing to occur only in regions of the TPO molecule not related to the epitopes identified by the studies below. Nagayama, Y et al., *J. Clin. Endocrinol. Metab.* 71:384–390 (1990); Zanelli, E. et al., *Biochem. Biophys. Res. Commun.* 170:735–741 (1990). Moreover, since both of the alternative transcripts previously described also appear to be present in normal thyroid glands, the relationship of alternative splicing to the development of autoimmunity is somewhat questionable. Elisei, R. et al., *J. Clin. Endocrinol. Metab.* 72:700–702 (1991).

Immunodiagnostic Applications

Immunoassays utilizing isolated natural epitope, the recombinant protein, or a synthetic peptide representing specific TPO epitopic regions can be used to evaluate patients for autoimmune thyroid disease. By screening for antibodies against the TPO epitope or epitopic region, patients with autoimmune thyroid disease such as Hashimoto's can be distinguished from patients with other thyroid disorders, such as Graves' disease.

Current immunoassays for diagnosing Hashimoto's disease use whole thyroid microsomal antigen partially purified from bovine thyroid glands. While this material contains TPO, it is also contaminated with many other bovine proteins and has a slightly different structure from the human antigen. Possibly as a result of such contamination and species dissimilarities, current assays are only about 80% sensitive and do not correlate well with disease activity.

The present invention provides substantially pure TPO epitopic sequences which can be consistently produced in large quantities. As used with respect to the present invention described in the specification and claims, the term "TPO epitopic region, sequence, peptide or amino acid" is meant to include a region or sequence of TPO from amino acid 456 to 933 of SEQ ID NO. 1 or fragment thereof which includes at least one distinct TPO epitope, unless otherwise indicated or evident from the use of the term in context. It will be appreciated that this term thus also includes simply TPO epitope. The term should also be construed broadly as to the source of the TPO epitope or region, whether isolated from natural or recombinant sources or synthetically produced, unless otherwise indicated or evident from the context in which the term is used. By "substantially pure TPO epitopic region, sequence, peptide or amino acid" is meant TPO epitopic region or sequence from any of these sources which is substantially free from undesirable contaminants such as other proteins, with a purity of greater than 90%. The term is not meant to exclude TPO epitope or region which is linked, bound to or intentionally combined with other moieties such as carrier proteins, labels, flanking amino acid sequences and the like. Nucleic acid sequences, either DNA or RNA, consisting essentially of the coding sequences for the TPO epitopic regions or fragments thereof described above, and nucleic acid sequences complementary thereto, are also contemplated as within the scope of the present invention.

TPO epitopes encompassed by the present invention are specific for thyroid peroxidase and, in substantially pure form, show no measurable cross-reactivity with other types of peroxidase enzymes as seen with whole molecule immunoassays currently in use. The use of TPO epitope as an immunodiagnostic tool in accordance with the present invention thus has the distinct advantage that it is recognized only by antibodies against the specific binding site in human TPO, the actual autoantigen associated with the disease. Furthermore, recombinant or synthetic epitopic regions can be produced in homogenous or substantially pure form without contaminating animal proteins.

As described above and detailed in Specific Example I, the identification of specific TPO epitopic regions and the development of an exemplifying immunodiagnostic assay involved several steps. Prior to this work it was believed that TPO needed to be intact in order to be recognized by antibodies. Using a eukaryotic expression system, it was found that large portions of the TPO coding region could be removed without destroying the antigenic activity. As discussed in Specific Example I, a small segment of the TPO (SEQ ID NO:2) gene coding for approximately 180 of the 933 amino acids in the whole molecule was identified which seemed to identify the antigenic epitope. In order to produce large amounts of this protein for investigation, an expression system using a vector not previously employed in TPO studies was able to translate this specific segment of the molecule. By inserting a small segment of the TPO gene into an appropriate vector, an approximately 140 amino acid fragment of TPO fused to a carrier protein was produced. This fusion protein (MBP-TPO) reacted with human Hashimoto's sera but not with control sera, and inhibited binding to larger portions of the molecule. By using this unique expression system, a recombinant autoantibody epitope was identified and produced.

The further localization of the TPO epitope to a 140 amino acid region between amino acids 517 and 633 (SEQ ID NO:1) results in the ability to produce substantially pure natural or recombinant TPO epitopic sequences or synthetic peptides corresponding to or containing a TPO epitopic region. The specific TPO epitopes of the invention can be used in a variety of immunobinding assay schemes known to those skilled in the art to detect the presence of antibody in clinical or research settings. As described in detail in Specific Examples IV and V, the exact epitope of TPO autoantibodies directed to the fragment of TPO contained within amino acids was determined. A distinct binding region from amino acid 592 to 613 (SEQ ID NO:1) was found which is unique to thyroid peroxidase and has an amino acid sequence different from other peroxidase enzymes including loctoperoxidase and myeloperoxidase. This portion of TPO can be used to differentiate autoantibodies in Hashimoto's disease from those in Graves' disease.

An extremely sensitive and specific immunoassay for anti-TPO antibody is thus provided in accordance with the present invention. For example, an assay for autoimmune thyroiditis is provided, which includes (a) substantially pure thyroid peroxidase epitopic peptide which specifically binds to thyroid peroxidase autoantibody, the peptide having of an amino acid sequence of from residue 456 to 933 of SEQ ID NO. 1 or an epitopic fragment thereof; (b) reagent means for detecting the binding of the autoantibody to the epitopic peptide; and, (c) the epitopic peptide and reagent means each being present in amounts effective to perform the immunoassay. The components of the assay can also be provided in kit form, and in suitable packaging or a container. The present invention also provides a method for using the immunoassays of the present invention.

The present invention further provides, in part, a method of screening for the presence of autoantibody to thyroid peroxidase in a sample comprising the steps of: (a) providing the sample to be screened; (b) providing a thyroid peroxidase reagent comprising a substantially pure thyroid peroxidase epitopic peptide having an amino acid sequence of from residue 456 to 933 of SEQ ID NO. 1 or an epitopic fragment thereof; (c) providing means for detecting binding of epitopic peptide reagent to autoantibody; (d) contacting the autoantibody with the thyroid peroxidase reagent under conditions favorable for binding; and, (e) employing means for detecting the binding of epitopic peptide to the autoantibody. It is contemplated that the sample may comprise biological fluid or tissue, perferably a sample comprising blood or serum. Specifically, an ELISA assay as set forth in Specific Example I and FIG. 19, to detect human antibodies against TPO epitopes, is also provided by the present invention.

IMMUNOTHERAPEUTIC APPLICATIONS

Overview. The present invention provides new immunotherapeutic approaches to the treatment of patients with thyroid cancers, particularly those which have not responded to conventional therapies. In these patients, thyroid cancer does not respond to treatment with radioactive iodine because the cancer is not sufficiently differentiated to concentrate lethal quantities of radioactivity. While other thyroid specific antigens, such as thyroglobulin and the TSH receptor, may no longer be expressed on these cells, thyroid peroxidase (TPO) appears to be expressed even on poorly differentiated thyroid tumors. Many patients with thyroid cancer have evidence of thyroiditis and specific immunity to TPO. However, the natural level of this immunity in these patients appears inadequate to control the cancer. Because the TPO epitope is thyroid specific and present on thyroid cells as a membrane bound antigen, antibodies against the epitope can specifically bind to and destroy the thyroid cancer cells. Intense and specific cellular immune responses to TPO in Hashimoto's thyroiditis are associated with the type of cytolytic immunity necessary to destroy cancer cells. In contrast to most current tumor immunotherapy, which targets poorly defined antigens, the availability of recombinant TPO peptides enables the induction of a cellular immune response to this molecule leading to cytotoxicity. Since patients with autoimmune thyroid disease who develop antibodies against this epitope destroy their thyroid cells and become hypothyroid, autoimmune thyroid disease serves as an in vivo model of the use of TPO epitope in active immunotherapy of thyroid cancer.

For example, as detailed in Specific Example III, defined recombinant purified fragments of human TPO of the invention were immunologically recognized by patients with follicular and papillary thyroid cancer. The immunologic recognition of TPO protein fragments in the cancer patients involved both serologic and cellular elements and was specific for the TPO portions of the fusion proteins. TPO fusion proteins also induce the antigen-specific secretion of TNF by thyroid cancer infiltrating lymphocytes, the induction of at least one type of cytotoxic activity. The TPO epitopic fragments have also been shown to induce de novo specific serologic immune response to native TPO when used to immunize animals.

As a thyroid-specific antigen TPO can play several roles in immunotherapy. Active immunization with TPO epitope is particularly attractive if a patient demonstrates prior sensitization. Immunization has advantages over conventional chemotherapy or radiation therapy in that it would cause specific destruction of the thyroid tumor without otherwise adversely affecting the patient's health or well-being. By coupling the TPO epitopes of the present invention to highly immunogenic carrier proteins, such as maltose binding protein, the immune response to thyroid peroxidase can be induced. A TPO epitope vaccine can also be useful as adjuvant therapy to prevent metastasis in patients who have a primary thyroid cancer resected. Several epitopes (each about 20 to 40 amino acids) can be coupled to a known adjuvant, such as tetanus toxoid, liposomes or vaccinia virus, and administrated as a vaccine. Because thyroidectomy is performed on almost all patients with thyroid cancer, the local immune cells responding to the tumor can also be harvested and used for adoptive immunotherapy. TPO epitope can be used in this strategy to stimulate antigen-specific cytotoxic cells in vitro, which can then be re-infused into the patient.

Other methods of using the TPO epitope involve passive immunotherapy against the epitope using monoclonal antibodies raised against the epitope. Adapting techniques known to those skilled in the art for producing monoclonal antibodies, monoclonal antibodies to TPO epitope can be isolated and infused into individuals with thyroid cancer, where they will bind and kill the thyroid cancer cells. This technique would be particularly useful in patients who are too ill to make an adequate immune response to the vaccine. In addition, monoclonal antibodies against TPO epitope can be coupled with toxins or drugs to target and deliver the toxins or chemicals directly to the thyroid cells. Putative clones producing such monoclonal antibodies have been isolated using the techniques described in Baker, J. R. Jr. et al., *J. Immunol.* 140:2593–2599 (1988).

These epitopes can also be used to develop TPO-specific LAK cells in vivo for the therapy of thyroid cancer. The thyroid cancer infiltrating lymphocytes can be harvested from tissue obtained at thyroidectomy. These lymphocytes contain a high percentage of thyroid-reactive cells, and by culturing these cells with the recombinant thyroid peroxidase epitopes, one can stimulate the growth of T cells specific for TPO. These cells can be expanded by repeated cycles of antigen and interleukin 2, and re-infused into the patient where they will migrate to the sites of tumor cells and mediate tumor cell lysis.

Identification of the specific epitopic regions of TPO also provides new avenues for treatment of autoimmune thyroiditis such as Hashimoto's disease. For example, the patient can be treated with TPO epitope or regions to bind and competitively inhibit autoantibody from binding to native TPO epitope. An alternate treatment scheme involves the blocking of native TPO epitope, e.g., with an autoantibody binding mimic, which prevents autoantibody binding to the native TPO epitope, but does not have undue adverse effects on any necessary TPO function.

In practicing the present invention, the amount of TPO epitope to be used or administered, alone or in combination with other agents, will vary with the test and/or the patient being treated and will be monitored on a patient-by-patient basis by the physician. For immunotherapeutic applications, including vaccines, generally a therapeutically effective amount of the epitope will be administered for a therapeutically effective duration. By "therapeutically effective amount" and "therapeutically effective duration" is meant an amount and duration to achieve a selected desired result in accordance with the present invention without undue adverse physiological effects, which can be determined by those skilled in the medical arts. It will also be appreciated that administration of the epitopic regions and reagents and vaccines which include the epitopes of the present invention, will be by procedures well established in the pharmaceutical arts, e.g. intramuscular, subcutaneous, intradermal and oral administration, either alone or in combination.

Thyroid Cancer. Although there are four types of thyroid carcinomas, medullary, anaplastic, papillary and follicular, the latter two cell types which both arise from the thyroid follicular cells, account for 85% of all thyroid cancers. Papillary cancer accounts for approximately 70% of all thyroid cancers and 85% of radiation-induced cancers. Mazzaferri, E. L., "Thyroid Cancer," Ch. 43:319–331 (Becker, K. L. ed.) *Principles and Practice of Endocrinology and Metabolism,* J. B. Lippencott (Philadelphia, Pa. 1990); Cooper, D. S. et al., *Endocrinol. Metab. Clin. North Am.* 19(3):577–591 (1990). Follicular cancer accounts for 15% of all thyroid cancers, and is seen more commonly in the elderly and in patients with goiter from iodine deficient areas. Block, B. L. et al., *Otolaryngol. Clin. North Am.* 23(3):403–411 (1990). Follicular cancer can manifest an aggressive nature despite a benign pathologic appearance, and is more likely than papillary cancer to be metastatic when first diagnosed. Block, B. L. et al., *Otolaryngol. Clin. North Am.* 23(3):403–411 (1990); Watne, A. L. et al., *Semin. Surg. Oncol.* 7(2):87–91 (1991). The overall 10-year mortality of 15 to 50% in patients diagnosed with follicular cancer reflects both the more aggressive nature of this tumor and the poor course seen in elderly individuals with this tumor. Watne, A. L. et al., *Semin. Surg. Oncol.* 7(2):87–91 (1991). In either papillary and follicular carcinomas, larger tumors (>3–5 cm) are associated with poorer outcomes. Watne, A. L. et al., *Semin. Surg. Oncol.* 7(2):87–91 (1991). Smaller lesions can follow a benign and protracted course, but are also found in association with distant metastasis. Mazzaferri, E. L., "Thyroid Cancer," Ch. 43:319–331 (Becker, K. L. ed.) *Principles and Practice of Endocrinology and Metabolism,* J. B. Lippencott (Philadelphia, Pa. 1990); Cooper, D. S. et al., *Endocrinol. Metab. Clin, North, Am.* 19(3):577–591 (1990). Thyroid cancers are present in situ in approximately 10% of all autopsy specimens, indicating that a benign pre-clinical form of the disease is very common. Bisi, H. et al., *Cancer* 64(9):1888–1893 (1989); Clark, O. H. et al., *Eur. J. Cancer Clin. Oncol.* 24(2):305–313 (1988).

It is important to note that papillary and follicular thyroid carcinoma maintain many of the characteristics of follicular thyroid cells. They display specific proteins associated with thyroid cells, such as the TSH receptor, thyroglobulin and TPO. Mazzaferri, E. L., *J. Clin. Endocrinol. Metab.* 70(4):826–829 (1990); Paul, S. J. et al., *Endocrinol. Metab. Clin. North Am.* 19(3):593–612 (1990). They also function in a manner consistent with thyroid cells, responding to TSH stimulation, concentrating iodine and producing thyroglobulin and thyroid hormone. These features have important implications for treatment and also aid in diagnosis. Tumors that concentrate iodine can be identified and located with $^{123}I$ or $^{131}I$ scans, and recurrences of tumors after resection or treatment can be detected by monitoring serum levels of thyroglobulin or by radioactive scanning. Krenning, E. P. et al., *Eur. J. Cancer Clin. Oncol.* 24(2):299–304 (1988); Sisson, J. C., *Endocrinol. Metab. Clin. North Am.* 18(2):359–387 (1989).

Current Therapy for Thyroid Cancer. Papillary carcinoma is often cured by partial or complete thyroidectomy with thyroid hormone replacement therapy to suppress endogenous TSH stimulation of the cancer when the lesion is small (less than 1.5 cm) and well circumscribed. Mazzaferri, E. L., *Semin. Oncol.* 14(3):315–332 (1987). However, in patients over 40 years of age, patients with a history of radiation exposure, patients with multifocal tumors and patients with local lymphatic metastasis, thyroidectomy alone is associated with up to a 40 to 60% recurrence rate in patients with a primary tumor greater than 2.5–3.0 cm. Khan, A. et al., *Throat J.* 68(1):31–32, 34, 39–40 (1989). In these cases and in patients initially presenting with distant metastasis, surgery is followed by adjunctive therapy with radioiodine. Mazzaferri, E. L., "Thyroid Cancer," Ch. 43:319–331 (Becker K. L., ed.) *Principles and Practice of Endocrinology and Metabolism,* J. B. Lippencott (Philadelphia Pa. 1990); Cooper, D. S. et al., *Endocrinol. Metab. Clin. North Am.* 19(3):577–591 (1990). While retrospective studies suggest this decreases recurrence rates in many patients, especially in the absence of metastatic disease, some patients have only partial responses to radioiodine and receive a maximal cumulative dose of 800–1000 mCi of $^{131}I$ without achieving a complete remission. In addition, many metastasis do not concentrate iodine and show no response to $^{131}I$ administration. This results in a substantial portion of patients (10 to 20%) with papillary cancer who can not be cured by traditional therapy. The overall outlook for these patients is bleak, as no chemotherapeutic regiment or other treatment modality has been shown to be effective. Kvols, L. K. et al., *Semin. Oncol.* 14(3):343–353 (1987). This results in a 10–20% cancer-related mortality for papillary cancer patients in the 20 years following diagnosis. Mazzaferri, E. L., "Thyroid Cancer," Ch. 43:319–331 (Becker, K. L. ed.) *Principles and Practice of Endocrinology and Metabolism,* J. B. Lippencott (Philadelphia, Pa. 1990); Cooper, D. S. et al. *Endocrinol. Metab. Clin. North Am.* 19(3):577–591 (1990).

Follicular thyroid cancer shares many of the same treatment concerns as papillary cancer, however it is even more lethal. Watne, A. L. et al., *Semin. Surg. Oncol.* 7(2):87–91 (1991). Total thyroidectomy for follicular carcinoma without radioiodine therapy does not commonly yield a cure because of the cancer's propensity to widely metastasize. Cooper, D. S. et al., *Endocrinol. Metab. Clin. North Am.*

19(3):577–591 (1990). Patients with metastases that do not concentrate iodine tend to have particularly unfavorable outcomes because this tumor is usually more aggressive than its papillary counterpart. Chemotherapy for follicular cancer is also ineffective, and patients often require additional surgery or local radiation for palliation. In older patients with invasive disease, follicular cancer results in mortality rates of 50% in the ten years following diagnosis. Watne, A. L. et al., *Semin. Surg. Oncol.* 7(2):87–91 (1991).

Thus, while current therapy for thyroid cancer may be effective, a substantial proportion of patients do not respond to these measures. In these patients, there are currently no alternative therapeutic modalities to relieve their substantial morbidity and mortality. The many patients with thyroid cancer who respond well to conventional treatment obscure the serious nature of this disorder in those patients with progressive disease.

Immune Aspects of Thyroid Cancer. Several findings suggest the immune system attempts to regulate neoplastic thyroid cells. For example, the presence of thyroid cancers in situ in 10% of autopsies suggests that neoplastic transformation of thyroid cells is relatively common. Bisi, H. et al., *Cancer* 64(9):1888–1893 (1989); Clark, O. H. et al., *Eur. J. Cancer Clin. Oncol.* 24(2):305–313 (1988). It is possible that a secondary neoplastic event or possibly the breakdown of immune surveillance results in a clinically recognizable thyroid cancer. There is often a lymphocytic infiltrate surrounding papillary thyroid cancer, and this infiltrate can become so intense it must be differentiated from autoimmune thyroiditis. Mazzaferri, E. L., "Thyroid Cancer," Ch. 43:319–331 (Becker K. L., ed.) *Principles and Practice of Endocrinology and Metabolism*, J. B. Lippencott (Philadelphia Pa. 1990); Cooper, D. S. et al., *Endocrinol. Metab. Clin. North Am.* 19(3):577–591 (1990). In contrast to papillary cancer, follicular cancer does not commonly induce a local immune response (Watne, A. L. et al., *Semin. Surg. Oncol.* 7(2):87–91 (1991)) which may relate to the propensity for this cancer to metastasize. The fact that thyroid cancer is also more progressive and more likely to metastasize in elderly patients (Mazzaferri, E. L., "Thyroid Cancer," Ch. 43:319–331 (Becker, K. L. ed.) *Principles and Practice of Endocrinology and Metabolism*, J. B. Lippencott (Philadelphia Pa. 1990)) may also be a reflection of decreased immune function in this population.

In addition to the local histologic changes, patients with thyroid cancer often have antithyroid antibodies, including serum antibodies against thyroglobulin and thyroid peroxidase. Mazzaferri, E. L., Thyroid Cancer, Ch. 43:319–331 (Becker K. L., ed.) *Principles and Practice of Endocrinology and Metabolism*, J. B. Lippencott (Philadelphia Pa. 1990); Cooper, D. S. et al., *Endocrinol. Metab. Clin. North Am.* 19(3):577–591 (1990). Antibodies against these antigens do not seem to alter the prognosis or progression of the cancer and patients with antibodies against the either TPO or thyroglobulin are just as likely as patients without antibodies to die from their tumor. Pacini, F. et al., *Acta. Endocrinol.* (Copenh.) 119(3):373–80 (1988). Antibodies against the TSH receptor are also reported to occur in patients with thyroid cancer. Filetti, S. et al., *N. Engl. J. Med.* 318(12) :753–759 (1988). This type of immune response may be detrimental, as anti-TSH receptor antibodies have been reported to cause tumor stimulation in some thyroid cancer patients. Belfiore, A. et al., *J. Clin. Endocrinol. Metab.* 70(4):830–835 (1990). However, the demonstration of antithyroid antibodies in thyroid cancer patients suggests that these patients are able to mount immune responses to a variety of thyroid-associated antigens.

Because serologic immunity is ineffective in many neoplasms and has not appeared helpful in controlling thyroid cancer, cellular immunity might be necessary to suppress thyroid neoplasms. In these patients the induction of antithyroid antibodies require a cellular immune response, and cellular cytotoxic immune responses are reported in tumor infiltrating lymphocytes (TIL) isolated from thyroid cancer. Bagnasco, M. et al., *J. Clin. Endocrinol. Metab.* 69(4) :832–836 (1989). However, the cellular cytotoxic activity of these TIL is not increased compared to the levels seen in peripheral blood and the predominant cytotoxic activity in the thyroid is due to NK cells not directed specifically towards thyroid cells. Bagnasco, M. et al., *J. Clin. Endocrinol. Metab.* 69(4):832–836 (1989). Importantly, papillary cancer TIL express lower levels of activation markers than intrathyroidal lymphocytes from patients with thyroiditis. Bagnasco, M. et al., *J. Clin. Endocrinol. Metab.* 69(4) :832–836 (1989); Bagnasco, M. et al., *Clin. Exp. Immunol.* 83(2):309–313 (1991). The thyroid cancer cells themselves do not express ICAM1 and have decreased expression of Class I HLA antigens, indicating a local absence of cytokines (such as γ interferon and TNFα) produced by activated mononuclear cells. Bagnasco, M. et al., *Clin. Exp. Immunol.* 83(2):309–313 (1991); Liaw, K. Y. et al., *Cancer* 46(2) :285–288 (1980). Several defects in cytotoxic immune responses have also been documented in the peripheral blood mononuclear cells from patients with papillary cancer, including decreased blastogenic responses to mitogens and additional work has shown a specific defect in peripheral blood NK lysis of thyroid cancer cells. Aoki, N. et al., *Clin. Exp. Immunol.* 38(3):523–530 (1987); Boros, P. et al., *Haematologia* (Budap.) 20(3):189–193 (1987); and Sack, J. et al., *Cancer* 59(11):1914–1917 (1987). Proliferative responses to thyroid antigens are also not as intense in cancer patients as in patients with thyroiditis and are seen in a much smaller percentage of cancer patients. Bagnasco, M. et al., *J. Clin. Endocrinol. Metab.* 69(4):832–836 (1989). Additionally, non-specific immune stimulation at the time of thyroidectomy has been shown to decrease papillary cancer recurrence rates. Durie, B. G. et al., *Cancer Clin. Trials* 4(1):67–73 (1981). Particular HLA alleles and IgG allotypes (Gm) are associated with the development of thyroid cancer, reinforcing the concept of an immune defect in these patients. (Juhasz, F. et al., *Cancer* 63(7):1318–1326 (1989); Juhasz, F. et al., *Clin. Endocrinol.* (Oxf.) 25(1):17–21 (1986). Thus, while there is evidence of a primary cytotoxic immune response to thyroid cells in thyroid cancer patients, it appears inadequate to control the neoplastic cells.

Chronic Thyroiditis: Cellular Immunotherapy of Thyroid Cancer. The augmentation of cellular immune responses to control thyroid cancer is supported by Hashimoto's (autoimmune) thyroiditis. As discussed previously, this disorder is caused by a specific immune response to thyroid antigens that results in an intense lymphocytic thyroiditis. Weetman, A. P. et al., *Endocrinol. Rev.* 5(2):309–355 (1984). While Hashimoto's is associated with thyroid-specific B cell immune responses, as demonstrated by antibodies to TPO and thyroglobulin (Weetman, A. P. et al., *Endocrinol. Rev.* 5(2):309–355 (1984)), a predominance of thyrocyte-specific T cell responses are observed. Weetman, A. P. et al., *Endocrinol. Rev.* 5(2):309–355 (1984). Importantly, the majority of T cell clones isolated from intrathyroidal cells are CD8$^+$ phenotype and demonstrate cytotoxic activity against thyroid cells, with the end result usually being hypothyroidism from the complete destruction of the thyroid gland. Bagnasco, M. et al., *J. Clin. Endocrinol. Metab.* 69(4) :832–836 (1989); MacKenzie, W. A. et al., *J. Clin. Endo-* crinol. Metab. 64(4):818–824 (1987). The histologic appearance of thyroid glands from patients with end stage thyroiditis demonstrates mainly lymphocytic immune elements and fibrosis. Few, if any, thyroid cells are present and there is total disruption of the normal thyroid architecture. Weetman, A. P. et al., *Endocrinol. Rev.* 5(2):309–355 (1984).

Animal models of thyroiditis reinforce the central role of cellular immunity in the pathogenesis of this disorder. Thyroiditis can be passively transferred between animals by T lymphocytes, T lymphoblasts and thyroid antigen-specific L3T4$^+$ T cell clones, but not with antithyroid antibodies. Okayasu, I., *Clin. Immunol. Immunopathol.* 36(1):101–109 (1985); Charreire, J. et al., *Eur. J. Immunol.* 12(5):421–425 (1982); Romball, C. G. et al., *J. Immunol.* 138(4) :1092–1098 (1987); Maron, R. et al., *J. Immunol.* 131(5) :2316–2322 (1983). In addition, thymectomy has been shown to prevent the development of the disease. Okayasu, I., *Clin. Immunol. Immunopathol.* 36(1):101–109 (1985). T cells from animals with lymphocytic thyroiditis have been shown to have cytotoxic activity for cultured thyrocytes in vitro and CD8$^+$ cells have been demonstrated to proliferate in response to thyroglobulin. Creemers, P. et al., *J. Exp. Med.* 157(2):559–571 (1983); Canonica, G. W. et al., *Clin. Immunol. Immunopathol* 36(1):40–48 (1985).

Based on the above discussion, by eliciting a cellular immune response to the thyroid which parallels Hashimoto's disease, cytolysis of thyroid cancer cells can be effected. Inducing a "Hashimoto-like" thyroiditis in thyroid cancer patients is desirable for several reasons. The inflammation would be thyrocyte-specific, and thus be unlikely to affect other organs. The immune response would be directed towards micrometastasis which is not detectable by any current assay procedure and would be missed during thyroidectomy. This would provide a means of clearing these cells potentially more effective than $^{131}$I and a greater likelihood of cure from thyroidectomy. This approach could also be effective against cancers that did not concentrate iodine, for which there is no present therapy. In addition, while normal thyroid cells would also be destroyed, the effects of hypothyroidism can be easily and completely resolved by treatment and are trivial compared to the effects of progressive thyroid cancer. In any case, all current therapies for thyroid cancer result in hypothyroidism, and immunotherapy offers fewer additional risks than radiation or surgery. Thus, immunotherapy of thyroid cancer has several advantages when compared to conventional therapy for thyroid cancer.

Several lines of investigation support the efficacy of inducing thyroiditis-like cellular immunity to treat thyroid cancer. While thyroid cancer is reported to occur in patients with Hashimoto's thyroiditis, there are several reasons why augmented antithyroid immune responses would be effective in preventing the development of thyroid cancer. Several studies have reported that thyroid cancer is seen solely in patients with localized thyroiditis surrounding a solitary intrathyroidal mass that was a focus of papillary cancer. Mauras, N. et al., *J. Pediatr.* 106(6):895–898 (1985); Maceri, D. R. et al., *Laryngoscope* 96(1):82–86 (1986). This subgroup of patients may not have had Hashimoto's disease, but in fact had tissue inflammation mimicking thyroiditis as a response to their malignancy. Mazzaferri, E. L., "Thyroid Cancer," Ch. 43:319–331 (Becker, K. L. ed.) *Principles and Practice of Endocrinology and Metabolism*, J. B. Lippencott (Philadelphia Pa. 1990); Cooper, D. S. et al., *Endocrinol. Metab. Clin. North Am.* 19(3):577–591 (1990). This mislabelling may have arisen from many investigators' identifying thyroid cancer patients with serum antithyroid antibodies as having thyroiditis, a problem with several studies on this subject. Mauras, N. et al., *J. Pediatr.* 106(6):895–898 (1985); Maceri, D. R. et al., *Laryngoscope* 96(1):82–86 (1986). When patients with diffuse goiter or hypothyroidism are considered separately, they have a much lower rate of malignancy than that found in normal patients on autopsy studies. Maceri, D. R. et al., *Laryngoscope* 96(1):82–86 (1986). The few cancers described in patients with generalized lymphocytic thyroiditis are localized and have no regional or distant metastasis. Mauras, N. et al., *J. Pediatr.* 106(6):895–898 (1985); Maceri, D. R. et al., *Laryngoscope* 96(1):82–86 (1986); Hoie, J. et al., *J. Surg. Oncol.* 37(3) :147–151 (1988). Given the fact that chronic inflammation is often thought to predispose to the development of cancer, the finding that cancer is seen less often in patients with chronic, diffuse thyroiditis indicates that the specific antithyroid immune response could control neoplastic thyroid cells.

Two groups have previously tried to induce thyroiditis as a treatment for thyroid cancer with limited success. One group used a crude extract of homogenated autologous thyroid cancer to immunize three patients with widely-metastatic thyroid cancer. Amino, N. et al., *Cancer* 36(3) :963–973 (1975). Two of the patients were anergic at the time of immunization, and showed no response to either the thyroid cancer or control antigens. The one patient who was not anergic did demonstrate a response to the vaccine and had a 33% decrease in tumor mass that persisted for over a year. In contrast, more recent studies which used acid-modified thyroglobulin to immunize eight patients with either papillary or follicular cancer were able to induce antithyroglobulin antibodies in five of the patients. Lo Gerfo, P. L. et al., *Surgery* 94(6):959–965 (1983). Two of the patients with thyroglobulin antibodies also developed thyroiditis, with one of the two having a 30% regression of tumor mass. Another patient without documented thyroiditis also had stabilization of the lung lesions (lung metastases were not biopsied) after immunization. Despite this success, antithyroglobulin antibody titers were not high in these patients, and it was difficult to evaluate the degree of immune response to immunization due to interference by circulating thyroglobulin. In addition, considering the present understanding of the pathogenesis of thyroiditis, thyroglobulin may not be the proper target antigen to induce thyroiditis. While neither of these studies demonstrated complete success, they indicate that thyroiditis can be induced in humans through immunization and suggest that the induction of thyroiditis may have an anti-tumor effect on thyroid cancer.

Evaluation of Antigens Potentially Useful in Induction of Thyroid-Specific Immunity in Thyroid Cancer Patients. Given that thyroid cancer regressions have been associated with induced immunity to thyroid cells, and that progressive thyroid cancer is associated with defects in cellular immunity, several methods of inducing and augmenting antithyroid cellular immunity are herein considered. While there are no documented thyroid cancer-specific antigens, it is fortunate that these cancers have been demonstrated to express thyroid-specific antigens. Because these thyroid antigens are human autoantigens, they are known to be immunogenic in man and are associated with human T cell cytotoxicity for thyrocytes. Thus, human thyroid autoantigens would present favorable targets of thyroid cancer-specific immunotherapy, particularly since the normal tissue is essentially expendable.

There are several identified thyroid autoantigens: thyroglobulin, thyroid peroxidase (TPO), the TSH receptor, and more recently, a 64 kDa antigen. Charreire, J., *Adv. Immunol.* 46:263–334 (1989); Weetman, A. P., *Clin. Exp. Immunol.* 80:1–3 (1990); Bech, K. et al., *Clin. Endocrinol.* (Oxf.) 11(1):47–58 (1979); Dong, Q. et al., *J. Clin. Endocrinol. Metab.* 72(6)A:1375–1381 (1991). Each have unique features which may offer advantages if used to induce thyroid-specific immunity. The 64 kDa antigen was recently identified through screening of a thyroid cDNA library and has been shown to be recognized by half the patients with Graves' disease. Dong, Q. et al., *J. Clin. Endocrinol. Metab.* 72(6)A:1375–1381 (1991). It may be a membrane antigen, however there is no evidence that it is associated with destructive immunity to thyroid cells. In addition, its presence on thyroid cancer cells is unknown, but is reported to be present on other tissues, including muscle cells. Dong, Q. et al., *J. Clin. Endocrinol. Metab.* 72(6)A:1375–1381 (1991). The 64 kDa antigen thus appears to be currently the least viable candidate antigen for immunotherapy.

The TSH receptor is also a membrane antigen specific to thyroid cells. It has recently been cloned and identified as an analogue of the rhodopsin receptor family. Parmentier, M. et al., *Science* 246(4937):1620–1622 (1989). It has a large extracellular N-terminal domain that has unique, potentially antigenic sequences. Wadsworth, H. L. et al., *Science* 249 (4975):1423–1425 (1990). However, there may be several problems in using this antigen for immunotherapy. The antigen is not commonly associated with immune responses that lead to destruction of thyroid cells (Burman, K. D. et al., *Endocrinol. Rev.* 6(2):183–232 (1985)) and no evidence of cytotoxic T cell responses is seen in Graves' disease. Antibodies against the TSH receptor may be helpful in that they could block the receptor and prevent stimulation of the cancer by TSH. However, immunizing with this antigen may result in thyroid stimulating antibodies which could stimulate tumor growth. Bagnasco, M. et al., *J. Clin. Endocrinol. Metab.* 69(4):832–836 (1989). Thus, immunotherapy involving the induction of immunity to the TSH receptor above does not appear feasible.

The two thyroid autoantigens with the greatest potential as immunogens for thyroid cancer are thyroglobulin and thyroid peroxidase (TPO), both associated with destructive thyroiditis. Thyroglobulin was the first recognized thyroid autoantigen and the first to be purified. Weetman, A. P. et al, *Endocrinol. Rev.* 5(2):309–355 (1984). It has been closely associated with thyroiditis, and is the major antigen in some animal models of thyroiditis. Okayasu, I., *Clin. Immunol. Immunopathol.* 36(1):101–109 (1985); Charreire, J. et al., *Eur. J. Immunol.* 12(5):421–425 (1982); Romball, C. G. et al., *J. Immunol.* 138(4):1092–1098 (1987); Maron, R. et al., *J. Immunol.* 131(5):2316–2322 (1983); Creemers, P. et al.,*J. Exp. Med.* 157(2):559–571 (1983); Canonica, G. W. et al., *Clin. Immunol. Immunopathol.* 36(1):40–48 (1985). However, these animal models of thyroiditis may not closely mimic the disease in man.

The thyroiditis induced by immunization with thyroglobulin is almost uniformly self-limited and does not result in the total destruction of the thyroid gland. Wick, G. et al., *Adv. Immunol.* 47:433–500 (1989); Krco, C. J. et al., *J. Immunogenet.* 17(6):361–370 (1990). In addition, immunization with thyroglobulin does not induce the formation of anti-TPO antibodies, which are seen in both animals with spontaneous thyroiditis and humans with Hashimoto's disease. Antithyroglobulin antibodies do correlate with disease activity in Hashimoto's patients, but to a lesser extent than anti-microsomal antigen (TPO) antibodies. Weetman, A. P., *Clin. Exp. Immunol.* 80:1–3 (1990). The induction of thyroiditis in animals is also highly dependent on the method of immunization, and only particular strains of animals develop the disease on immunization. Wick, G. et al., *Adv. Immunol.* 47:433–500 (1989). The antigenicity of thyroglobulin is also variable, a phenomenon that in humans and experimental animals seems to be related to the iodine content of the thyroglobulin. This is supported by the observation that thyroiditis is more common in geographic areas where there is dietary replacement of iodine. Sundick, R. S., *Immunol. Ser.* 52:213–228 (1990). Recent work in animals has shown that a T cell epitope in thyroglobulin requires an iodination site. MacKenzie, W. A. et al., *J. Clin. Endocrinol. Metab.* 64(4):818–824 (1987). It therefore may be very difficult to standardize the antigenicity of thyroglobulin. Importantly, thyroglobulin is not a membrane protein, and since it is released from the cells it may act as a blocking antigen that could blunt the induction of immunity or deflect the immune response away from thyroid cells. Thus, although thyroglobulin is associated with destructive thyroiditis in both man and animals, there are several drawbacks in employing this antigen to induce cellular immunity in patients with thyroid cancer.

There are several advantages to the use of TPO as an antigen. In contrast to animal models of thyroiditis induced by immunization with thyroglobulin, spontaneous thyroiditis in both humans and experimental animals is most closely associated with evidence of immunity to TPO. Weetman, A. P. et al., *Endocrinol. Rev.* 5(2):309–355 (1984); Wick, G. et al., *Adv. Immunol.* 47:433–500 (1989). This type of thyroiditis closely mimics the type of immune reaction required to destroy a thyroid cancer cell, since it results in thyrocyte cytolysis and the total destruction of the thyroid. Antibodies to TPO closely reflect the degree of inflammation in the thyroid gland in thyroiditis, and there is T cell sensitization to TPO in most patients. TPO is also a membrane antigen, and therefore presents a better target for immunotherapy than thyroglobulin.

The presence of TPO on most follicular cancers and about one half of papillary cancers has also been documented. Fragu, P. et al., *J. Clin. Endocrinol. Metab.* 45:1089–1096 (1977). It may in fact be present on a higher percentage of thyroid cancers, since many of the older studies measured TPO expression in thyroid cancer by examining tumors for functional peroxidase activity, while more recent immunohistologic studies have identified non-functional TPO in many cancers.

De Micco, C. et al., *Cancer* 67:3036–3041 (1991). Although TPO resides primarily on the apical membrane and microvillar surfaces in normal thyroid follicular cells, it can be observed on the plasma membrane in inflamed thyrocytes and thyroid cancer cells. Christor, K. et al.,*Acta. Histochem.* 58:275–289 (1977). Its expression appears to be induced by local inflammation serving to reinforce the autoimmune responses. Roman, S. H. et al., *Autoimmunity* 2(3):253–263 (1989). These findings indicate that TPO exhibits two important characteristics: it is an antigen associated with cytolytic immunity to thyroid cells and is a membrane antigen associated with a large proportion of thyroid tumors.

Patients with thyroid cancer often show evidence of sensitization to TPO, indicating at least a primary immune response to this antigen. Twenty-five to 50% of patients (depending on the technique) with papillary or follicular cancer have antibodies to TPO, and there have been scattered reports of the documentation of cellular immunity to "microsomal antigen". Pacini, F. et al., *Acta, Endocrinol.* (Copenh.) 119(3):373–380 (1988); Juhasz, F. et al., *Cancer* 63(7):1318–1326 (1989). Unfortunately, until recently many of the studies concerning the immune reactivity to TPO suffered because the identity of the microsomal antigen as TPO was not known, and as a result both the serologic and cellular immune assays were less sensitive than those for thyroglobulin. However, even the results of these older studies support the premise that TPO stimulation of anti-thyroid immunity in patients with thyroid cancer, is advantageous in inducing a secondary immune response rather than a primary one.

Despite the many advantages in using thyroid peroxidase, there are some potential disadvantages. Only one study has shown the effectiveness of affinity purified porcine TPO in the induction of thyroiditis. Kotani, T. et al., *Clin. Exp. Immunol.* 80(1):11–18 (1990). There is also extensive homology between TPO and myeloperoxidase (Kimura, S. et al., *Proteins: Structure, Function & Genetics* 3:113–120 (1988)), and immunization with the whole molecule might induce a cross-reacting immune response leading to the immune destruction of leukocytes, although this is not seen in patients with thyroiditis. Also, TPO may not be present on all thyroid cancers, which may somewhat limit its usefulness.

SPECIFIC EXAMPLE I—TPO EPITOPE IDENTIFICATION AND IMMUNOASSAY

Materials and Methods

Patients. Twenty-five patients with Hashimoto's disease were studied. They were diagnosed because of goiter or hypothyroidism and evidence of anti-microsomal antibodies in a titer greater than 1:1600 as detected with an agglutination assay (Ames Diagnostics, Ames Iowa). Study serum was obtained from all patients at the time of their enrollment and was frozen at −70° C. until use. Patients with non-autoimmune thyroid disease (multinodular goiters) who had no evidence of anti-microsomal antibodies by agglutination immunoassay were used as controls.

TPO Complementary DNA (cDNA). A Bluescript SK plasmid with the full length (3.1 kb) cDNA for human TPO inserted into the NotI/XbaI (5'–3') restriction sites was a gift of Dr. Basil Rapoport, VA Medical Center, San Francisco Calif. This plasmid contained the (longest) complete, full length coding sequence and therefore did not include the alternative splicing segments with the internal deletion that had been previously reported in Kimura, S. et al., *PNAS (USA)* 84:5555–5559 (1987); Nagayama, Y. et al., *J. Clin. Endocrinol. Metab.* 71:384–390 (1990) and Zanelli, E. et al., *Biochem. Biophys. Res. Commun.* 170:735–741 (1990).

Immunoprecipitations. Immunoprecipitations of in vitro translated TPO were carried out as follows. The Bluescript plasmid containing the cDNA for human TPO was digested separately with XbaI, ClaI, BamH1 and BglII to produce C-terminal truncations yielding translation products of 933 (full length), 631, 455 and 120 amino acids, respectively (designated TPO(1–933), TPO(1–631), TPO(1–455) and TPO(1–120) (SEQ ID NO:1)). The TPO plasmid was also digested with Eco47 III and BamHI. The ends of this linearized plasmid were then filled in with Klenow and the plasmid was subsequently ligated to itself. This plasmid was then digested with XbaI to yield a translation product with an internal deletion from amino acids 4 to 455 (TPO (Δ4–455) (SEQ ID NO:1)). After agarose gel electrophoresis confirmed digestion of the plasmids, these templates were incubated with T3 RNA polymerase and nucleotide triphosphates for 45 minutes at 37° C. to produce sense RNA. Translation was then performed by incubating the RNA with rabbit reticulocyte lysate (Promega, Madison Wis.) and $^{35}$S-methionine according to the vendor's protocol. Translation products were analyzed by SDS-PAGE and autoradiography and were found to have the expected molecular weight before being used in the immunoprecipitations (data not shown). Immunoprecipitation was then performed by mixing 100 μl of a 1:2 dilution of either Hashimoto's or normal sera, or 10 μg of a monoclonal antibody to TPO, with 7500 CPM of in vitro translated product for one hour at 37° C. This was followed by the addition 50 μl of Protein A agarose. The agarose was mixed thoroughly for approximately 1 hour at 37° C., and then allowed to settle from the mixture. The supernatant fluid was removed and the agarose was subsequently washed with PBS. The washed agarose was then treated with sample buffer containing beta mercaptoethanol and SDS to solubilize the bound proteins for subsequent analysis by SDS-PAGE and autoradiography.

Production of Recombinant TPO. The full length coding sequence for TPO was inserted into the NcoI restriction site of the *E. coli* expression vector pET 3d using appropriate adapters. See Studier, F. W. et al., *Meth. Enzymol.* 185:60–89 (1990). This construct was grown in *E. coli* HMS174(DE3) pLysS to an $OD_{600nm}$ of 0.4–0.5. A small sample was removed for later analysis and IPTG (isopropyl-β-D-thiogalactopyranoside) was added to the rest of the culture at a final concentration of 0.4 mM. This culture was grown for three hours at 37° C. and the bacteria were harvested by centrifugation (4000 g for 20 minutes) and resuspended in 25 ml of lysis buffer (10 mM phosphate, 30 mM NaCI, 0.25% Tween, 10 mM beta mercaptoethanol, 10 mM EDTA, 10 mM EGTA, containing 1 mM PMSF, 0.5 mg/ml leupeptin and 0.7 μg/ml pepstatin A). The treated bacteria preparation was then incubated with 1 mg/ml lysozyme for 30 minutes in an ice bath and sonicated with four, 30 second pulses at the end of the incubation. NaCI was added to bring the salt concentration to 500 mM and the suspension was then spun at 10,000 g for 30 minutes. The supernatant (henceforth called lysate) was saved and brought to a final protein concentration of 2.5 mg/ml using column buffer (10 mM phosphate, 0.5 M NaCI, 1 mM azide, 10 mM beta mercaptoethanol and 1 mM EGTA with PMSF, leupeptin and pepstatin A).

Protein from the bacterial lysate was then analyzed by SDS-PAGE with Coomassie staining, or electro-transferred onto nitrocellulose paper. This transfer was then immunoblotted with the mouse monoclonal antibody against TPO (1 μg/ml) and several high titer anti-TPO sera from Hashimoto's patients (1:100 dilution in phosphate buffered saline (PBS) with 1% BSA) at room temperature, with shaking, overnight. These strips were washed and then incubated with alkaline phosphatase labelled anti-human IgG or anti-mouse IgG, as appropriate for the primary antibody. After a final wash, the blots were developed using BCIP/NBT substrate solution.

A fragment of TPO cDNA was also placed into the *E. coli* expression vector pMaIcRI (New England BioLabs, Beverly, Mass.) in the following manner. The TPO cDNA was digested with BamHI and ligated to an adapter having an EcoRI 5' end. The ligation product was then digested with XbaI and ligated into pMaIcRI that had been digested with EcoRI and XbaI (5'–3'). This construct encoded a fusion protein in which the amino terminal portion is maltose binding protein (MBP) minus its leader sequence followed first by the sequence IEGRISEF (SEQ ID NO:10) (one letter amino acid code) and then amino acids 456–933 of human TPO (SEQ ID NO:1). This construct was transformed into *E. coli* XL-I and grown at 37° C. with shaking until $OD_{600nm}$ readings reached approximately 0.3. IPTG was added at a final concentration of 0.3 mM and the bacteria were cultured for two more hours. The cells were harvested by centrifugation and lysate was produced as described above.

The lysate was run over an amylose affinity column to isolate the MBP fusion proteins according to the vendor's protocol (New England BioLabs), after which the column was washed with 10 volumes of column buffer with 0.05% Tween 20. The fusion protein was eluted using a column buffer containing 10 mM maltose. One ml fractions were collected and assayed for protein by dye binding technique (BioRad, Richmond Calif.). Fractions containing protein were pooled and analyzed using SDS-PAGE. The proteins were then transferred to nitrocellulose membranes using standard techniques. Western blots of the electrophoresis were performed with 1:100 dilutions of normal sera, sera from TPO antibody positive Hashimoto's patients, and a 1:10,000 dilution of a rabbit antisera to MBP. Binding inhibitions were performed by preincubating the sera with 50 µg of native human thyroid microsomal antigen (prepared as described in Portmann, L. et al., *J. Clin. Endocrinol. Metab.* 61:1001–1003 (1985)) for four hours at room temperature before incubation with the nitrocellulose strip.

ELISA Studies. Ninety-six well microtiter plates were coated with 1 µg/ml anti-TPO monoclonal antibody, 100 µl/well, in bicarbonate buffer, pH 9.6, overnight at 4° C. The plates were washed, and blocked with 200 µl of 1% BSA in PBS for at least two hours. The plates were again washed with PBS, 0.05% Tween 20 (PBST), and incubated with 6 µg/ml human thyroid microsomes (prepared as described in Portmann, L et al., *J. Clin. Endocrinol. Metab.* 61:1001–1003 (1985)) for two hours at room temperature. The plates were then washed and either used immediately or filled with blocking buffer and stored at 4° C.

Hashimoto's patient sera were diluted 1:500 in PBS with 1% BSA, then diluted 1:2 with either the MBP-TPO fusion protein or an equimolar amount of a control fusion protein, maltose binding protein-LacZα. These dilutions were then incubated overnight at room temperature with gentle shaking, before being added to the microtiter plates. The sera were then incubated for four hours at room temperature, after which the plates were aspirated and washed. A 1:1000 dilution of alkaline phosphatase conjugated, anti-human IgG (Sigma, St. Louis Mo.) was then added and the plates were incubated for two hours at room temperature. The plates were then washed, p-nitrophenyl phosphate substrate was added and the $A_{405nm}$ was read after 45 minutes.

Results

Figure 1B:
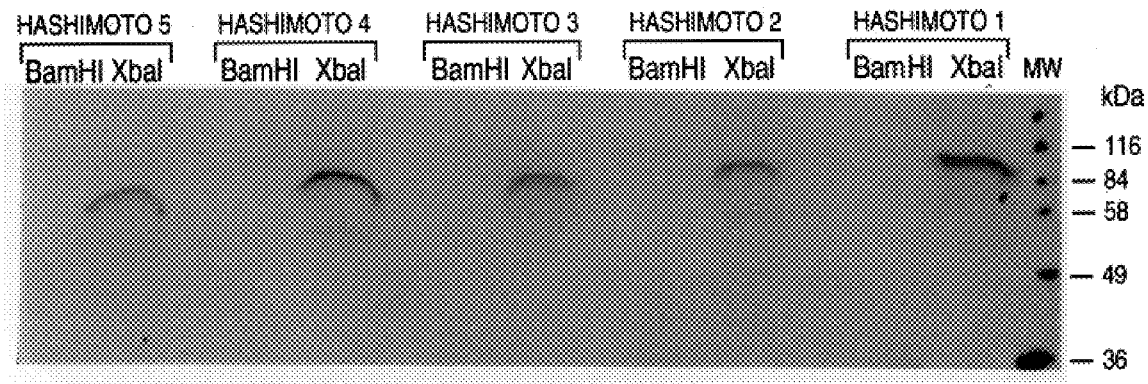

Immunoprecipitation Studies. $^{35}$S-labelled TPO fragments and the full length (933 amino acid) TPO protein (SEQ ID NO:1) were produced by in vitro translation and subjected to immunoprecipitation. As shown in FIGS. 1A–1B, six Hashimoto's patients' sera immunoprecipitated the full-length TPO produced from a cDNA linearized with XbaI (lanes labeled XbaI), but did not precipitate a fragment corresponding to the first 455 amino acids (labeled BamHI for the enzyme used to cut the cDNA). A mouse monoclonal antibody against TPO amino acids 266 to 281 (SEQ ID NO:1) as discussed in Finke, R. et al., *J. Clin. Endocrinol. Metab.* 71:53–59 (1990), was used as a positive control and precipitated both the full-length protein TPO (1–933) (SEQ ID NO:1) and TPO (1–455) (SEQ ID NO:1), but not the smaller fragment TPO ((1–120) (SEQ ID NO:1), labeled BglII) (SEQ ID NO:1). This confirms that the TPO (1–455) fragment was present and could have been precipitated if the Hashimoto's patients' sera antibodies bound to it. This suggested the absence of local autoantibody binding epitopes in the first 455 amino acids of the translation product.

Figure 2:
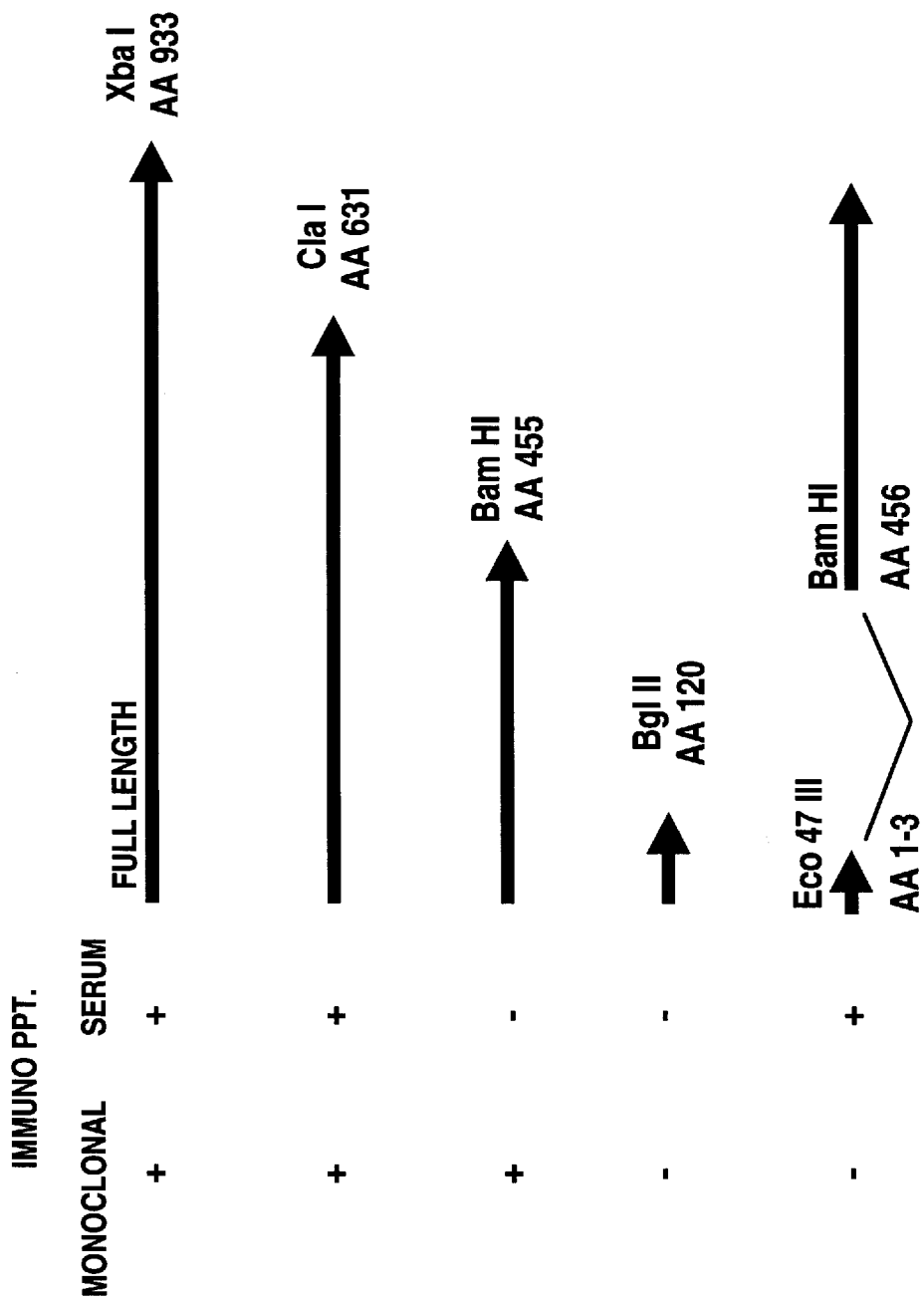
FIG. 2 summarizes immunoprecipitation results from multiple fragments (TPO constructs) of human TPO.

In order to confirm these studies and further localize putative autoantibody epitopes in the TPO molecule, two additional TPO fragments were produced by in vitro translation and immunoprecipitations were preformed. FIG. 2 summarizes the results from the monoclonal antibody binding to an epitope from amino acid 266 to 281 (SEQ ID NO:1) (presented in the left column) compared to those from Hashimoto's patients' sera (presented in the right column). The patient sera consistently bound only fragments containing the amino acid sequences after 455. All six Hashimoto's patients immunoprecipitated TPO (1–631) (SEQ ID NO:1) and TPO (Δ4–455) (SEQ ID NO:1). As expected, the mouse monoclonal antibody precipitated TPO (1–631) (SEQ ID NO:1) but not TPO (Δ4–455), the latter having an internal deletion which includes the monoclonal antibody binding site. Taken together, these results suggested the presence of autoantibody epitopes in the carboxyl-half of the TPO molecule, with at least one epitope localized between amino acids 456 and 631 (SEQ ID NO:1).

Figure 3:
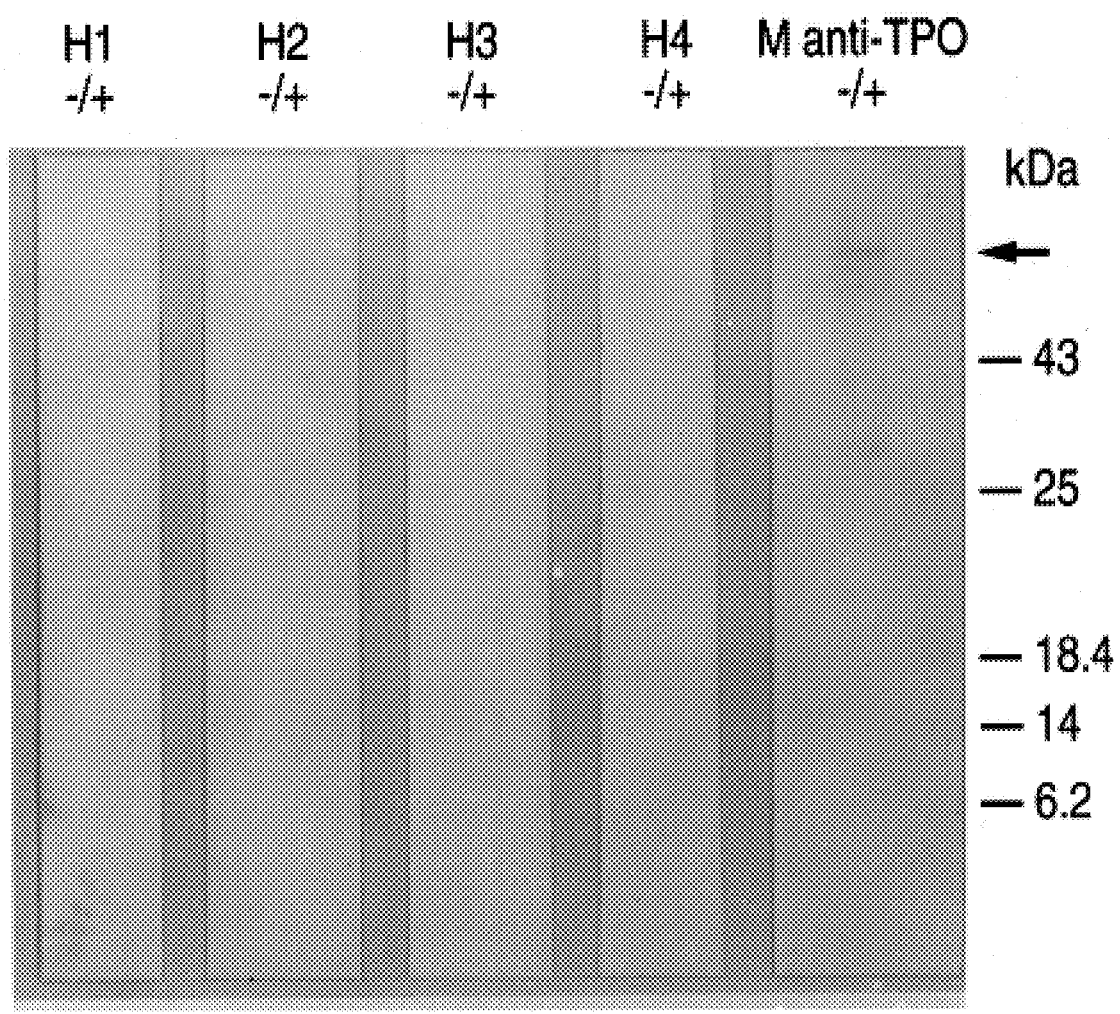
FIG. 3 is a Western blot analysis of the production of immunoreactive recombinant TPO using the pET 3d expression vector.

Studies Using Bacterial Expression Systems. In order to confirm the results of the immunoprecipitation studies using other techniques, *E. coli* were transformed with pET 3d vector expressing the full length cDNA for TPO. The transformed colonies were isolated and grown in culture to an OD of 0.6. The cultures were then split, with half the bacteria being exposed to IPTG (Isopropyl-β-thiogalacotpyranoside). The bacteria were isolated and a crude lysate was produced and subjected to SDS-PAGE (100 µg of protein lane). The gel was then transferred to nitrocellulose paper, and the paper was immunoblotted with four sera from patients with Hashimoto's thyroiditis and high-titer anti-TPO antibodies (depicted as H1 through H4 in FIG. 3) and a monoclonal antibody against TPO (depicted as M anti-TPO). Referring now to FIG. 3, Western blots of lysate from pET 3d (TPO) transfected bacteria induced with IPTG (depicted as+lanes) revealed a product which was identified by the mouse monoclonal antibody (referenced with an arrow), but not by the Hashimoto's patient sera. Since the molecular weight of this material was uniformly less than 48 kDa (approximately half the expected molecular weight of TPO) and the mouse monoclonal antibody identified an epitope early in the coding sequence (from amino acids 266 to 281) (SEQ ID NO:1) in the TPO molecule, it appeared that either only the N terminal of the TPO molecule was being translated or that the molecule was being fully translated and the carboxyl half was undergoing proteolytic digestion. Transfection of this vector into protease-deficient bacteria (not shown) did not alter the type or quantity of TPO protein produced, thus suggesting that the short TPO product was due to translation termination rather than proteolytic digestion.

In an attempt to find a more efficient expression vector, pMaIcRI (New England BioLabs, Boston Mass.) containing the coding sequence for MBP, a bacterial protein that binds and transports maltose, followed by the sequence of the insert cDNA nucleotides coding for TPO amino acids 456–933 (SEQ ID NO:1) was used. This construct has three advantages. The bacterial sequence appears to stabilize the subsequent translation of the eukaryotic RNA sequence. The resulting fusion protein can be affinity purified from whole bacterial lysate on an amylose column. In addition, a Factor Xα cleavage site is inserted in the pMALcRI vector between the MBP coding region and the polylinker insertion site so that the fusion protein can be cleaved from MBP to release the protein of interest.

The resulting plasmid (denoted pMAL-TPO 456–933) (SEQ ID NO:1) was transformed into E. coli XL1, and the transfected colonies were isolated and grown to an OD of 0.6. The bacteria were induced with IPTG, and cultured for 90 minutes. The cells were then harvested and a crude lysate was produced. This lysate was run over the amylose affinity column. The column was washed and the bound proteins were specifically eluted with 10 mM maltose-containing buffer. These proteins were separated by SDS-PAGE, and transferred to nitrocellulose paper.

Figure 4:
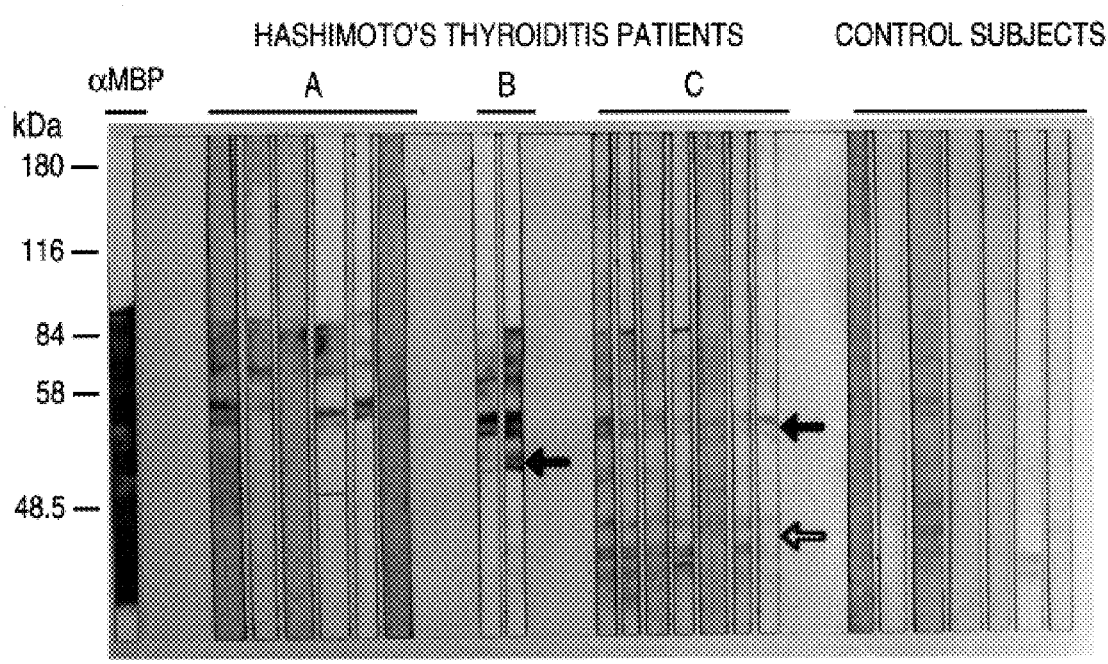
FIG. 4 is a Western blot analysis of MBP-TPO (AA 456–933) (SEQ ID NO:1) fusion proteins isolated from bacterial lysates by amylose affinity chromatography.
Figure 5:
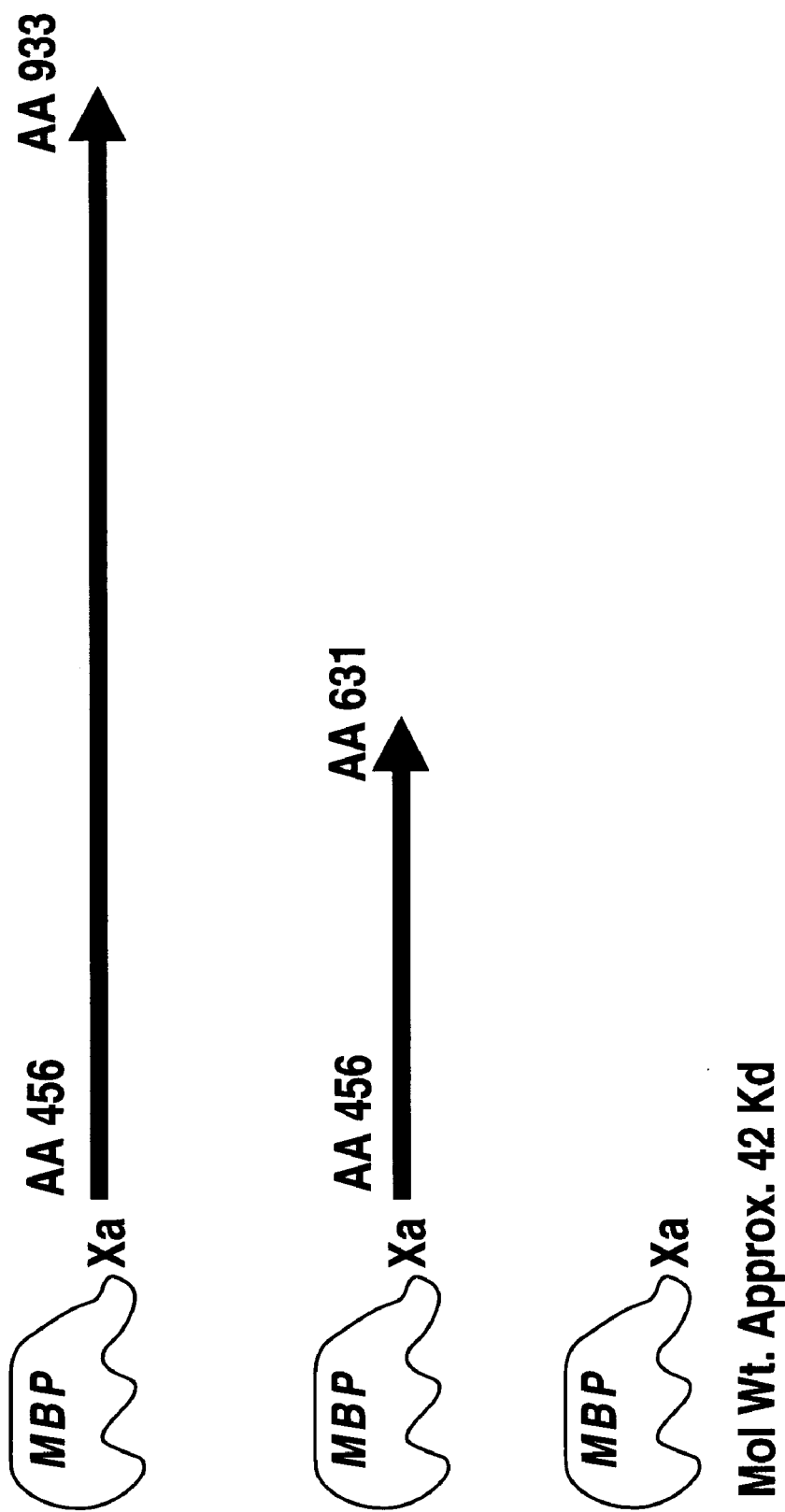
FIG. 5 illustrates TPO-maltose binding protein products.

The fusion proteins were analyzed for reactivity with Hashimoto's sera using Western blots. Referring now to FIG. 4, the lane marked α MBP was probed with a rabbit antisera to MBP. This lane shows all the electrophoresed proteins that were isolated from the amylose affinity column. The Hashimoto's patient sera react with multiple molecular weight fusion proteins in three general patterns of reactivity (A, B and C). A range of fusion products was revealed from 85 kDa (full-length MBP fused with amino acids 456 to 933 (SEQ ID NO:1) of TPO) to approximately a 42 kDa band (the molecular weight of the MBP without a translated fusion product). See FIG. 5. Reactivity with many of the bands above approximately 48 kDa was shown in the Hashimoto's sera, and none of the normal sera showed reactivity. The Hashimoto's patients showed several different patterns of reactivity with the smaller fusion proteins (depicted as dotted and clear arrows in FIG. 4), suggesting the presence of unique epitopes in the smaller transcripts that are recognized by sera from different subgroups of these patients. Overall, 24 of 25 Hashimoto's patients with anti-microsomal (agglutination) titers of greater than 1:1600 had positive reactivity to this fusion protein on the immunoblots, but there was no relationship between anti-microsomal antibody titer and immunoblot intensity (data not shown).

The fragments smaller than 85 kDa most likely represent C-terminal TPO truncations rather than N-terminal MBP truncations for two reasons. First, N-terminal truncations of even 10–20 amino acids would not bind to the amylose affinity matrix and would therefore not be isolated in the fractions analyzed by SDS-PAGE (Personal communication, Paul Riggs, New England Biolabs). Second, if there were N-truncations of the fusion protein, the most likely cause would be proteolysis. This latter possibility was addressed by the use of several protease inhibitors (PMSF, leupeptin, pepstatin A and EDTA) and by expressing the fusion protein in the protease-deficient E. coli strain SW6AA2 (lon, rpoH am165). However, neither of these manipulations significantly decreased the quantity of smaller fusion peptides, suggesting they were not proteolytic fragments.

Figure 6:
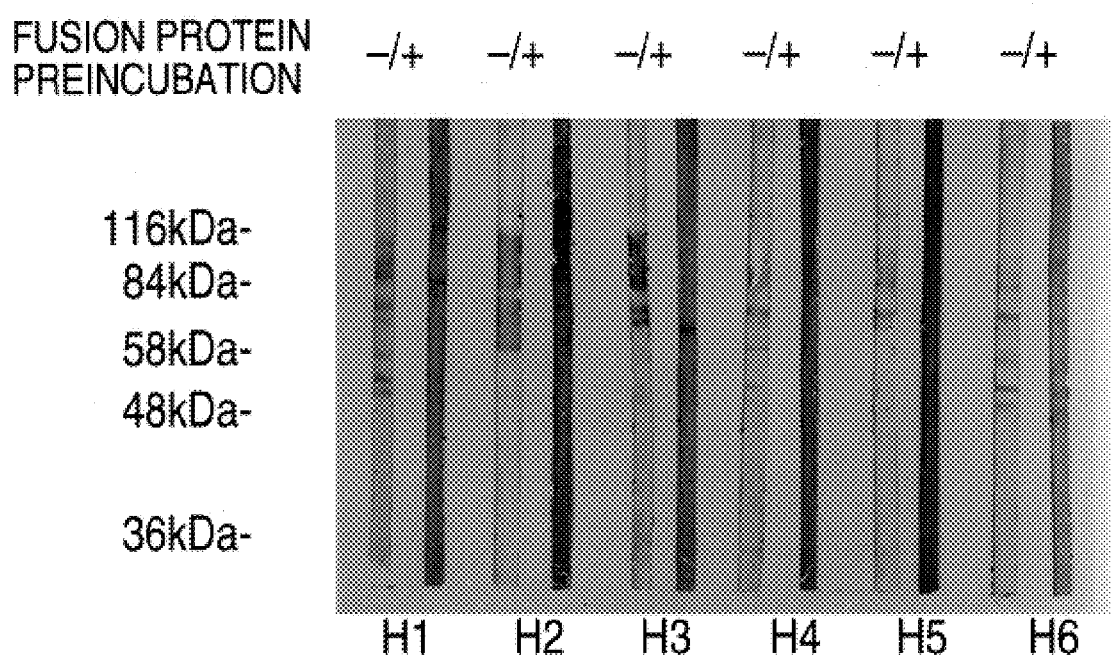
FIG. 6 is a Western blot analysis of the ability of native TPO to inhibit autoantibody binding to recombinant MBP-TPO fusion protein.

Five of the Hashimoto's patients demonstrating the most intense reactivity with the fusion protein on Western blot were analyzed for cross-reactivity between native TPO and the recombinant MBP-TPO fusion protein. Referring now to FIG. 6, plus (+) lanes are blots probed with Hashimoto's sera preincubated with native thyroid microsomes, while minus (−) lanes are the same sera preincubated with a control protein (BSA). In all five sera the antibody binding to the recombinant TPO fusion protein was completely inhibited by preincubation with a ten-fold molar excess of native TPO. This indicated that the epitopes recognized by the patients' sera in the recombinant fusion proteins were present in native TPO.

Figure 7:
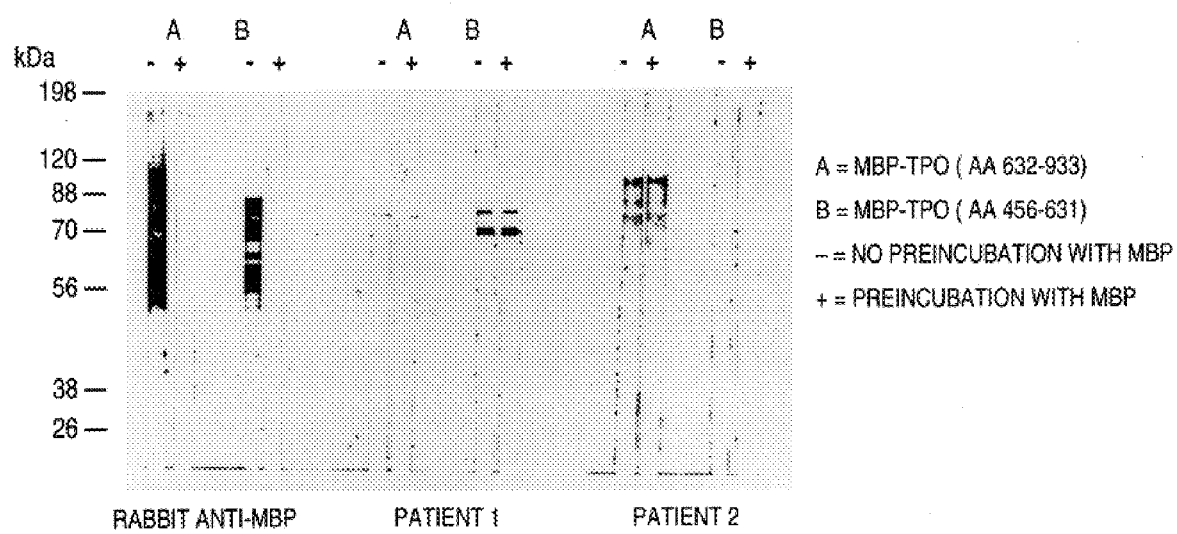
FIG. 7 is a Western blot analysis of thyroiditis patient sera reactivity with two different TPO epitopes.

Because of the possibility that multiple antigenic sites might exist in TPO between amino acids 456 and 933 (SEQ ID NO:1), new pMALcRI constructs were made that expressed smaller portions of the TPO molecule. Specifically, pMALcRI-TPO 456–631 (SEQ ID NO:1) was created, which produced a MBP fusion protein containing TPO amino acids 456–631 (SEQ ID NO:1), and pMAL TPO 632–933 (SEQ ID NO:1) which produces a MBP fusion protein containing TPO amino acids 632–933 (SEQ ID NO:1). The fusion proteins produced by these plasmids were independently recognized by autoantibodies from patients with Hashimoto's disease verifying the presence of multiple autoantibody binding sites in the TPO sequence from AA 456–933 (SEQ ID NO:1). Referring now to FIG. 7, Patient 2 not only reacted with the AA 632–933 (SEQ ID NO:1) fragment, but reacted with a wide variety of bands produced from this fragment. Neither patients' binding was inhibited by MBP, confirming the specificity of the antibodies for the TPO sequences. In total contrast, no autoantibody binding could be identified in the N-terminal half (AA 1–455) (SEQ ID NO:1) of the TPO molecule. Maastricht, J. et al., *J. Clin. Endocrinol. Metab.* (accepted for publication 1992). This may be explained by the fact that the N-terminal half of the TPO molecule demonstrates greater homology with other peroxidase enzymes, such as myeloperoxidase, than does the amino acid sequence beyond amino acid 455. See Kimura, S. et al., *Proteins: Structure, Function, and Genetics* 3:113–120 (1988). This suggests that the specificity of the human immune response for TPO autoimmune thyroiditis relates to recognition of sites not shared with myeloperoxidase.

When screening large numbers of patients for reactivity to recombinant peptides corresponding to TPO amino acid sequences 517–630 (SEQ ID NO:1) and 631–933 (SEQ ID NO:1) (see FIGS. 9A and 9B), vastly different reactivity is seen. While >80% of patients react to AA 631–933, only 20% of patients react to epitopes located between AA 517–630 (SEQ ID NO:1). However, in these latter patients there is marked reactivity to this region. This suggests unique reactivity in patients with thyroiditis, and potential differences in reactivity which may relate to disease pathogenesis.

It also appears that the region between amino acids 633 and 933 (SEQ ID NO:1) contains more than one antibody binding site. This is supported by data indicating that only half of the patients who bind to the amino acid 633 to amino acid 933 (SEQ ID NO:1) fragment also bind to a peptide fragment corresponding to amino acids 633 to 768 (SEQ ID NO:1). This indicates that the patients who do not bind to the 633 to 768 (SEQ ID NO:1) fragment bind to a region involving amino acids 768 to 933 (SEQ ID NO:1).

Figure 19:
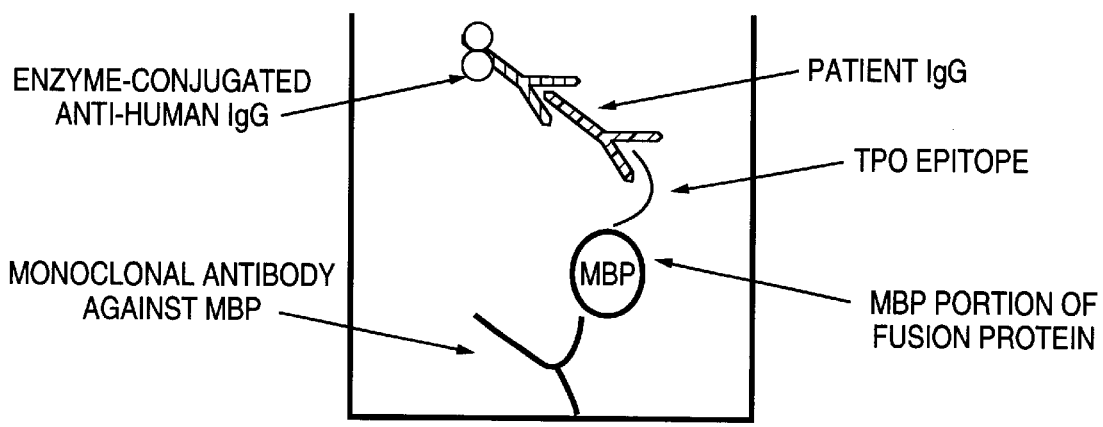
FIG. 19 is a graphical representation of an ELISA immunoassay for TPO autoantibody epitopes.

ELISA Inhibition Assays. FIG. 19 shows a graphical representation of an ELISA for detection of human antibodies against TPO epitopes. Plates are coated with monoclonal antibodies directed against MBP and partially purified MBP-TPO fusion protein is incubated, and bound by the monoclonal antibody. After washing, human sera diluted 1:400 is added to the well and binds to the TPO epitope (to prevent sera binding to bound MBP, the sera is preincubated with soluble MBP). The bound human antibody is then detected with anti-human IgG preabsorbed against mouse IgG. An enzyme substrate is then added to quantitate bound enzyme, which is proportional to the amount of bound human IgG. The assay can be adapted to measure antibody to any TPO epitope (or any other autoantigen) by substituting a different MBP-containing fusion protein).

Figure 8:
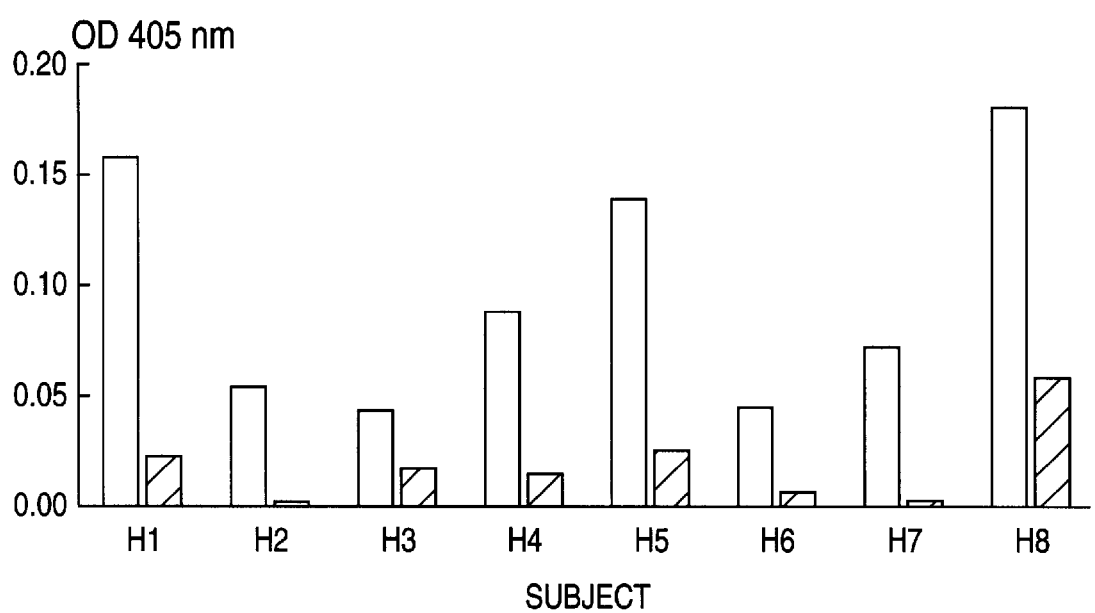
FIG. 8 is a block graph illustrating inhibition of Hashimoto's patient sera binding to native TPO in an ELISA by preincubation with different MBP fusion proteins.

ELISA inhibitions were carried out with seven patients having anti-TPO activity. The solid phase antigen used in the assay, of which the results are set forth in FIG. 8, is native human TPO bound to the ELISA plate wells using the mouse monoclonal anti-TPO antibody. As shown in FIG. 8, preincubation with the MBP-TPO (AA 456–933) (SEQ ID NO:1) fusion protein (depicted as striped bars) was compared to inhibitory binding to native TPO as compared with preincubation with a control fusion protein (MBP-LacZα, depicted as solid bars). Preincubation with the MBP-TPO fusion protein inhibited binding to the native TPO 70–100% as compared to the control fusion protein which caused only 10–15% inhibition. In four of the eight patients, the inhibition with MBP-TPO was to the background levels of the assay. These results suggest that the majority of the autoantigen epitopes in native TPO are located in the area of the region of the molecule distal to amino acid 455 (SEQ ID NO:1).

SPECIFIC EXAMPLE II—IMMUNOTHERAPY

Figure 10:
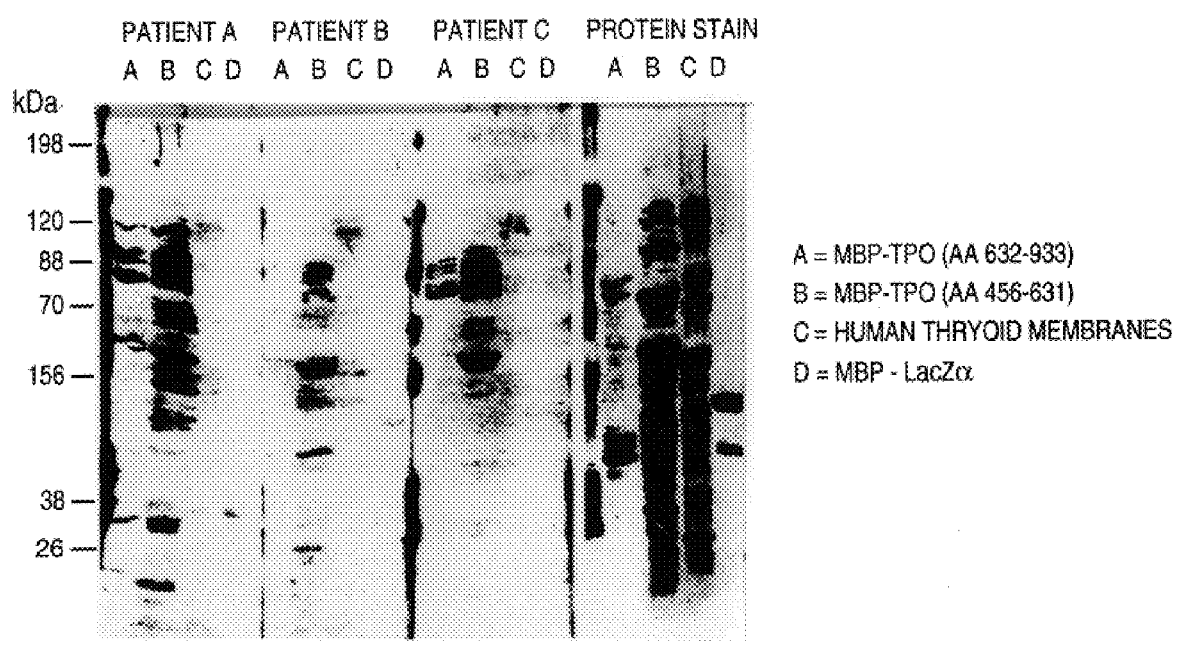
FIG. 10 is a Western blot analysis of sera from patients with thyroid cancer and thyroiditis.

It is important to evaluate autoantibody reactivity to the newly identified localized epitopes of TPO because of the prevalence of antibodies to the thyroid microsomal antigen in several diverse patient populations. Elderly patients without evidence of overt thyroid disease, where up to 20% of individuals (primarily females) demonstrate autoantibodies as described in Spaulding, S. W., *Endocrinol. Metab. Clin. North Am.* 16(4):1013–1025 (1987), were the first individuals evaluated to determine if some of these patients had antibodies against the localized TPO determinants as a marker of true autoimmune disease. During the course of these studies sera from three patients with thyroid cancer were evaluated. The Western blots of FIG. 10 depict studies of a patient with papillary thyroid cancer (Patient A), follicular thyroid cancer (Patient B) and Hashimoto's thyroiditis (Patient C). Reactivity with both types of fusion proteins and human TPO (lanes A, B, and C), as well as the lack of reactivity with MBP (lane D), is shown. While these patients were not actually "normal" elderly individuals, all three demonstrated autoantibodies to the recombinant TPO epitopes. It appeared that these patients' antibodies were in lower titer than those found in most Hashimoto's patients. However their reactivity to the localized TPO epitopes was as great or greater than that seen to the whole, native TPO molecule. The fact that cancer patients would have antibodies to TPO despite clinically significant and locally progressive thyroid cancer appears paradoxical. However, none of these three patients, one with follicular cancer and two with papillary carcinoma, exhibited distant metastasis. Both of the patients with papillary cancer had a mononuclear cell infiltrate surrounding their cancers but still had evidence of local progression. Thus, there was no clear relationship between the presence of anti-TPO antibody and either the type of thyroid cancer or evidence of a local immune reaction. This suggested that patients with thyroid cancer had pre-existing immune responses to TPO and that antibody to TPO alone might not be sufficient to control thyroid cancer.

Purification of MBP-TPO Fusion Proteins. Because of the evidence of serologic responses to TPO in thyroid cancer patients, an evaluation of cellular immune responses to TPO in these patients was performed. It was postulated that some form of cellular immune response was necessary to generate the anti-TPO antibodies, and in autoimmune thyroiditis immune reactivity to TPO is associated with cellular cytotoxic responses to thyroid cells. Since cellular immunity to thyroid cells was likely to be a crucial factor in the immune response to cancer, it seemed an important factor to evaluate in cancer patients. Unfortunately, the immunoreactive TPO fusion proteins isolated from the amylose affinity column demonstrated a broad range of molecular weight fusion proteins, as shown in FIG. 10, and were not of a purity suitable for use in cellular studies. This made defining the precise location of T cell epitopes difficult, and the problem was further compounded because the material appeared to contain a predominance of maltose binding protein sequence. In an attempt to resolve this problem, the pMAL-cRI plasmid was transfected into in lon and rpoH am165 deficient *E. coli* strain (data not shown) and fusion proteins were produced in these bacteria. This procedure still yielded fusion proteins with molecular weights below the expected size for the full-length fusion translation product. This again suggested that these smaller products were not the result of protease digestion. It appeared that since the shorter-length translation fragments bound and were affinity purified on the amylose column, these smaller fusion proteins must be C-terminal truncations since all but 10 amino acids of the N-terminal of MBP are necessary for binding to maltose (Personal communication, New England Biolabs). Thus, the largest fusion proteins having a molecular weight equal to the combination of the full TPO sequence and MBP should contain the whole TPO sequence.

Figure 11:
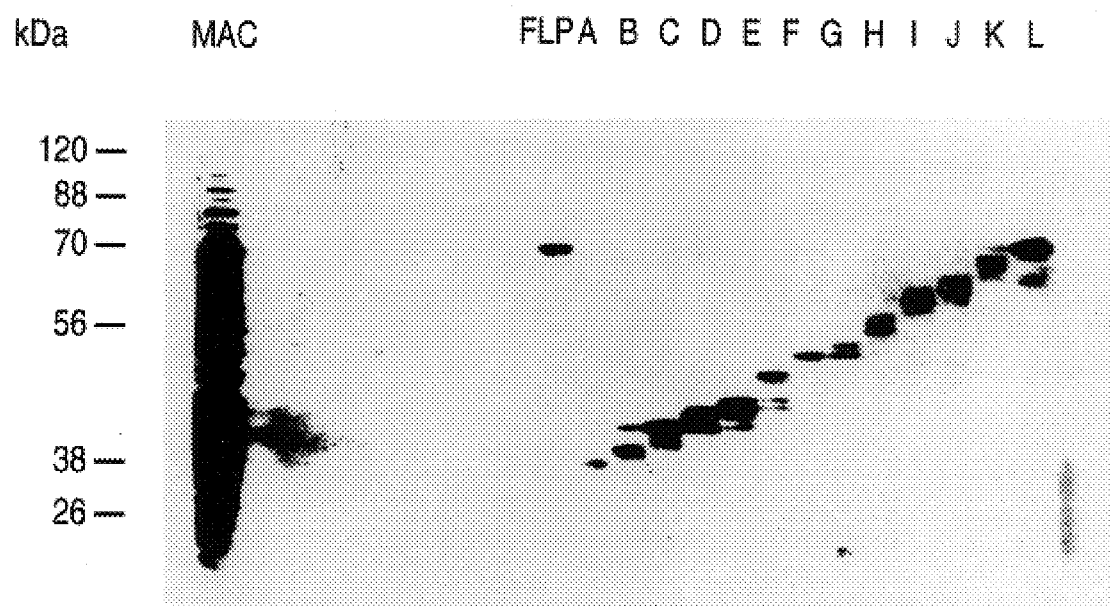
FIG. 11 is an immunoblot analysis of the separation of MBP-TPO fusion proteins by preparative SDS-PAGE.

An attempt was made to isolate the full-length translation products by molecular weight separation. A number of techniques were evaluated for this, with HPLC proving to be the only technique that provided adequate separation of the different molecular weight MBP-TPO fragments. Unfortunately, the amount of material isolated by this method was minimal and insufficient for immunologic studies. A technique that employs preparative SDS-PAGE (Prep Cell, BioRad, Richmond Calif.) to isolate the different molecular weight MBP-TPO (AA 633–933) (SEQ ID NO:1) fusion proteins within ±2% of molecular weight was employed. As shown in FIG. 11, the large number of different molecular weight fusion proteins isolated using amylose affinity columns (MAC-labelled lane) were subsequently separated by molecular weight using preparative SDS-PAGE. The full length translation product (FLP labelled lane) was isolated using this technique and is shown next to a number of other fractions isolated from the mixture (lanes A–L). This technique proved highly effective, yielding hundreds of micrograms of purified material that was strongly recognized by sera from patients with Hashimoto's disease, and it allowed the purification of a full-length fusion protein from whole bacterial lysate in twosteps. The final material was found to be free of other proteins and was also negative for endotoxin on limulus assay. This purified material was appropriate for use in T cell studies.

Figure 12:
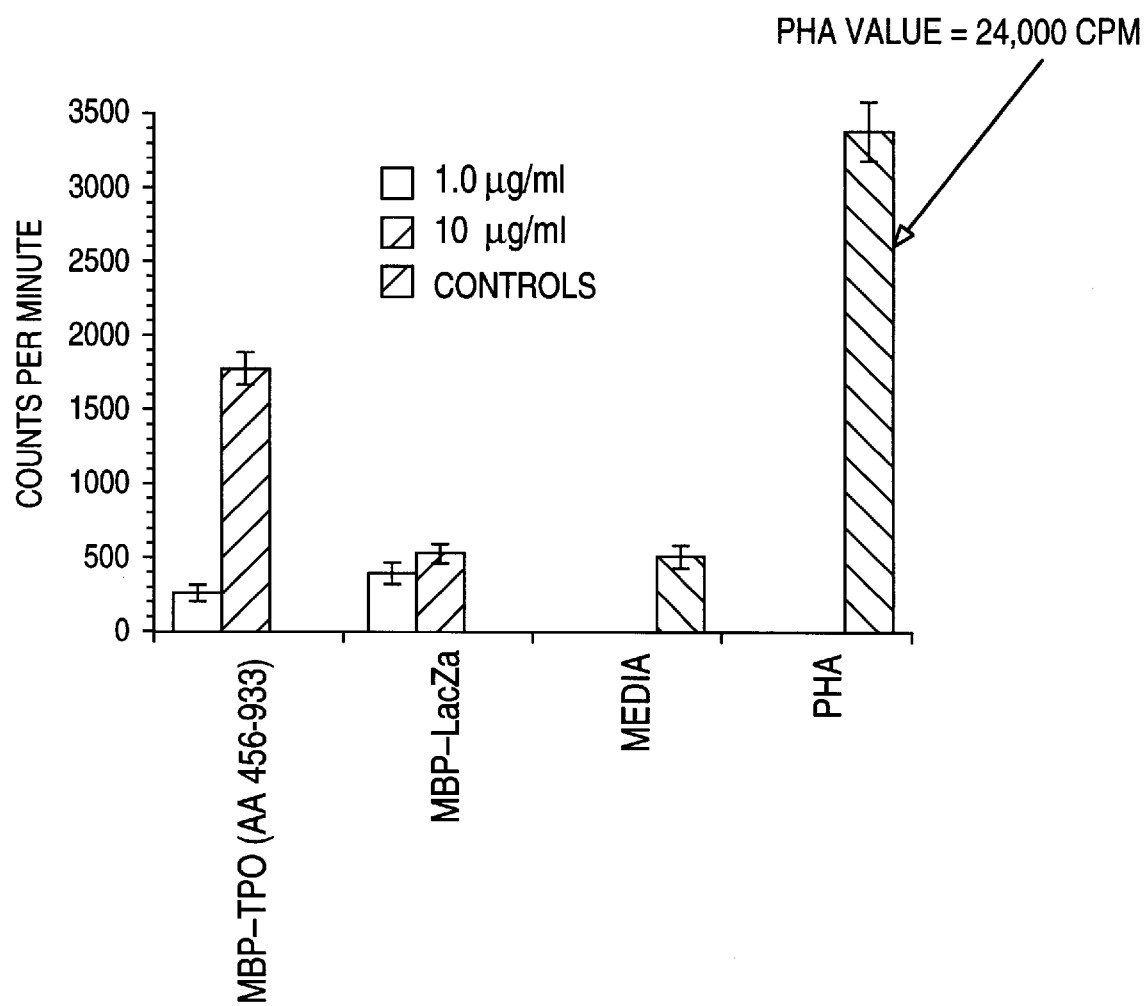
FIG. 12 is a bar graph depicting autoimmune thyroiditis patient T cell proliferation in response to recombinant TPO fragments.

Cellular Immunity to MBP-TPO Fusion Proteins. The response of peripheral blood mononuclear cells to stimulation with TPO fusion protein (MBP-TPO AA 456–933) (SEQ ID NO:1), control fusion protein (MBP-LacZα), media and PHA controls is shown in FIG. 12. Cells were incubated with the antigens for 96 hours, then pulsed with tritated thymidine and harvested 24 hours later. Specific proliferation was observed only to the 10 μg/ml concentration of the MBP-TPO fusion. Lower concentrations of antigen showed no effect. MBP-TPO (AA 456–933) (SEQ ID NO:1) fusion proteins isolate from the Prep Cell were specifically recognized by peripheral blood mononuclear cells from patients with Hashimoto's thyroiditis, suggesting the presence of epitopes recognized by human T cells in the TPO sequence. The demonstration of this reactivity in thyroiditis patients prompted further examination of cellular responses in thyroid cancer patients.

Figure 13A:
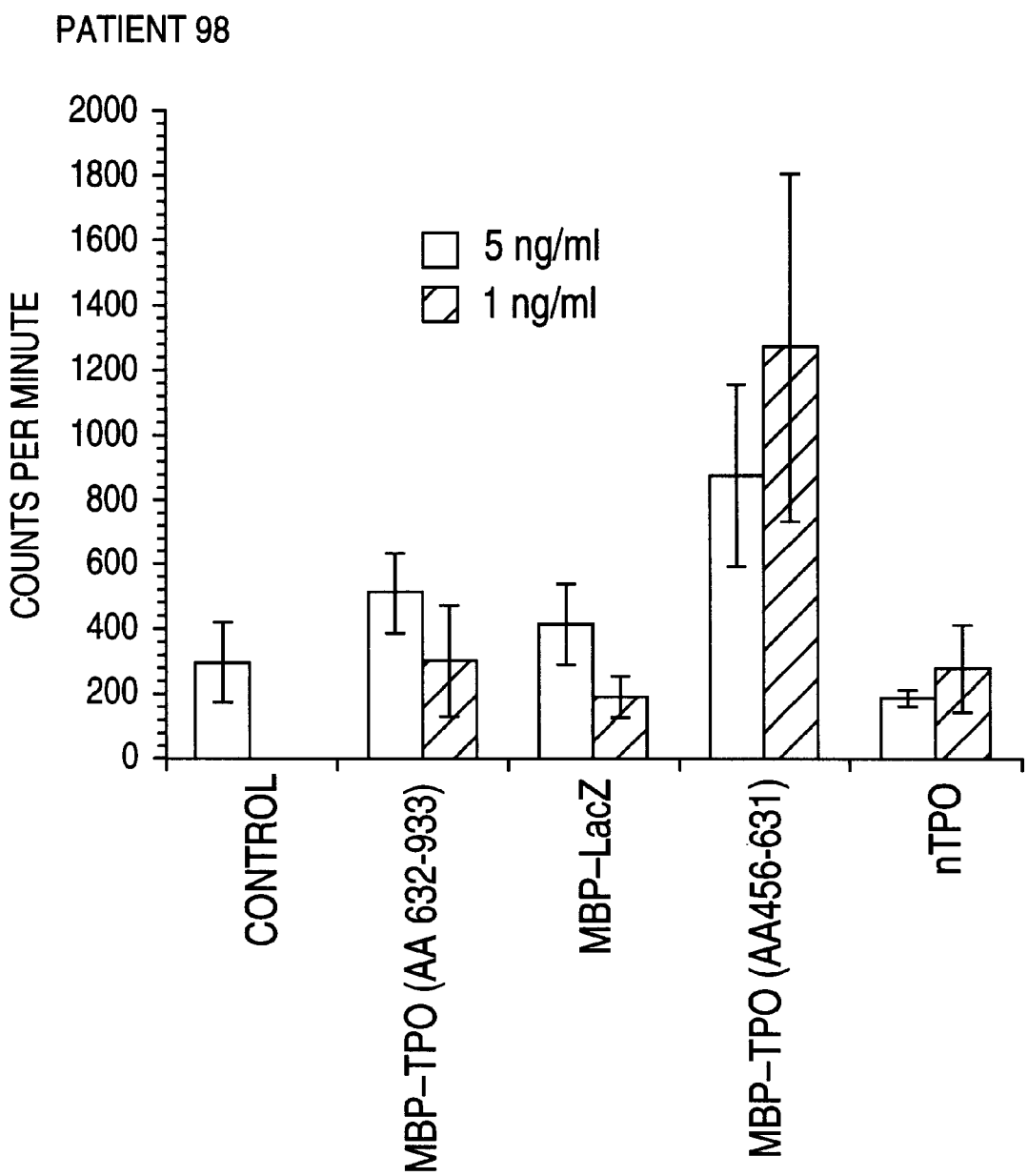
FIGS. 13A and 13B are bar graphs depicting proliferation of thyroid cancer patient peripheral blood lymphocytes (PBL) to thyroid antigens.
Figure 13B:
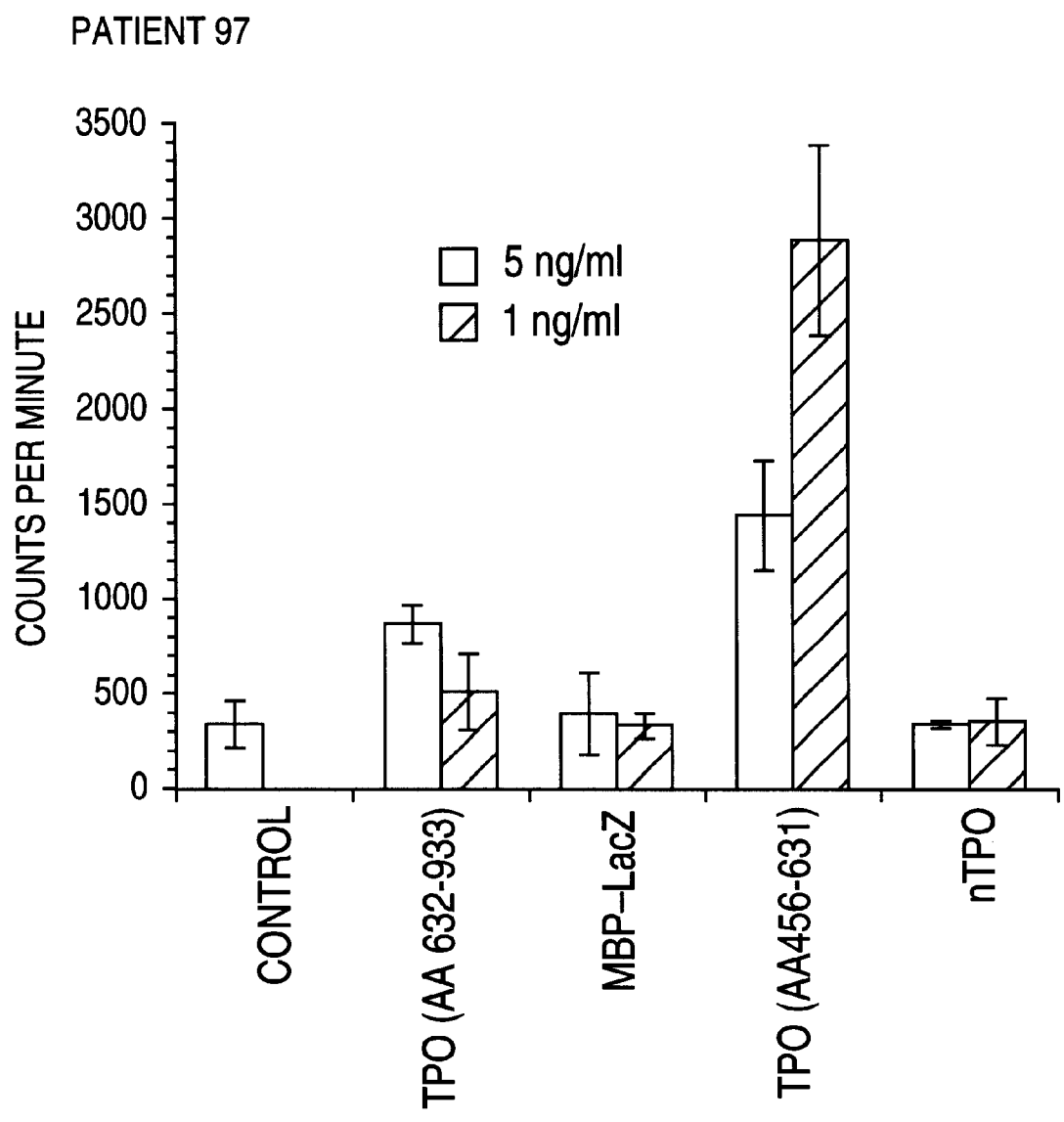

In an attempt to evaluate cellular reactivity to the TPO fusion proteins, Prep Cell purified MBP fusion proteins representing the TPO fragments AA 456–633 (SEQ ID NO:1) and AA 633–933 (SEQ ID NO:1) were used to stimulate peripheral blood mononuclear cells from cancer patients. Prep Cell purified maltose binding protein-LacZα fusion proteins and native human TPO (isolated from thyroid microsomes using the Prep Cell) were used as controls. The cells were incubated for 96 hours with different concentrations of purified thyroid antigens, and were then pulsed with thymidine and harvested 24 hours later. As shown in FIGS. 13A and 13B, specific proliferation was seen in response to one of the TPO fragments (AA 456–633) (SEQ ID NO:1), but not to the other fragment (AA 633–933) (SEQ ID NO:1), control MBP fusion proteins (LacZα) or native TPO. A third patient with follicular thyroid cancer was also evaluated, and showed a similar pattern although the total counts ranged from 200–600 total CPM. In two of the patients evaluated, specific proliferation in response to the AA 456–633 (SEQ ID NO:1) fragment was clearly demonstrated. This proliferation was not only greater than the MBP control, but also greater than that seen to native TPO. The reason for this is not clear, as the gravimetric concentrations of the proteins were equivalent and the molar concentrations of the different proteins were only 1.5 fold different. It is possible that the native TPO, which is heavily glycosylated, requires more processing by antigen-presenting cells, thus making it less effective than the recombinant protein in stimulating antigen-specific T cell proliferation. However, the stimulation seen with the TPO fusion protein was greater than that observed with the MBP-LacZα fusion protein, indicating that the stimulation was not due to MBP amino acid sequences. These results indicated that there was pre-existing cellular immunity to TPO in the cancer patients and this immunity could be stimulated by recombinant protein fragments of TPO.

Figure 14:
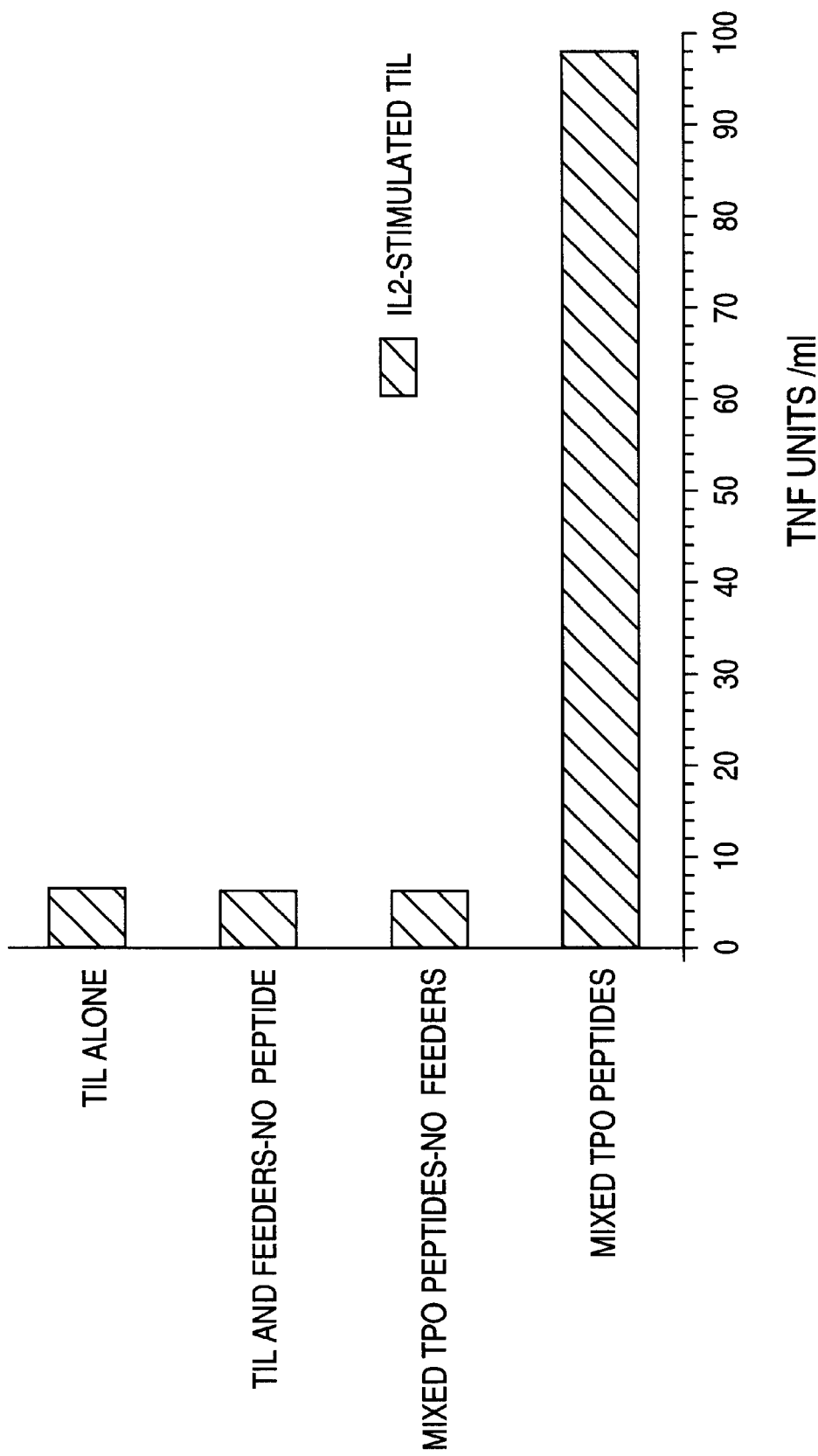
FIG. 14 is a bar graph depicting stimulation of papillary thyroid cancer-infiltrating lymphocytes (CIL) with TPO fusion proteins.

With the lymphocyte proliferation studies providing evidence of cellular immunity to the TPO proteins in cancer patients, studies were performed to determine if there was also evidence of cytotoxic activity related to this cellular immunity against TPO. The most likely source of T cells with this activity would be the lymphocytes infiltrating the thyroid cancer. The thyroidectomy specimen from one of the patients demonstrating proliferative activity to the synthetic TPO fragment in his peripheral blood lymphocytes was obtained. The patient underwent a thyroidectomy and was found to have papillary cancer with a localized mononuclear cell infiltrate surrounding his cancer. The lymphocytes from this thyroid gland were isolated, and the T cells were expanded by two different techniques: culture of the cells for two weeks with either supernatant fluid of lymphokine activated killer (LAK) cells or with IL2 alone. These expanded lymphocytes were then incubated with antigen alone or in combination with irradiated syngeneic antigen presenting cells (feeder cells) for 12 hours, and TNF production was measured 18 hours after the addition of antigen using a bioassay described in Flick, D. A. et al., *J. Immunol. Meth.* 68:167–175 (1984). As the LAK supernatant expanded, T cells produced TNF in a non-specific manner, primarily in response to the syngeneic antigen presenting cells. In contrast, the IL2 stimulated cells showed TNF production only in response to the TPO fragments in the presence of antigen presenting cells and were not reactive with autologous mononuclear cells or other non-TPO fusion proteins as shown in FIG. 14. This result indicated that there were lymphocytes infiltrating the thyroid that could specifically recognize TPO fragments in the presence of antigen presenting cells and respond by secreting TNF. In addition, the specificity of this response could be maintained while expanding the cells under appropriate culture conditions.

Figure 15:
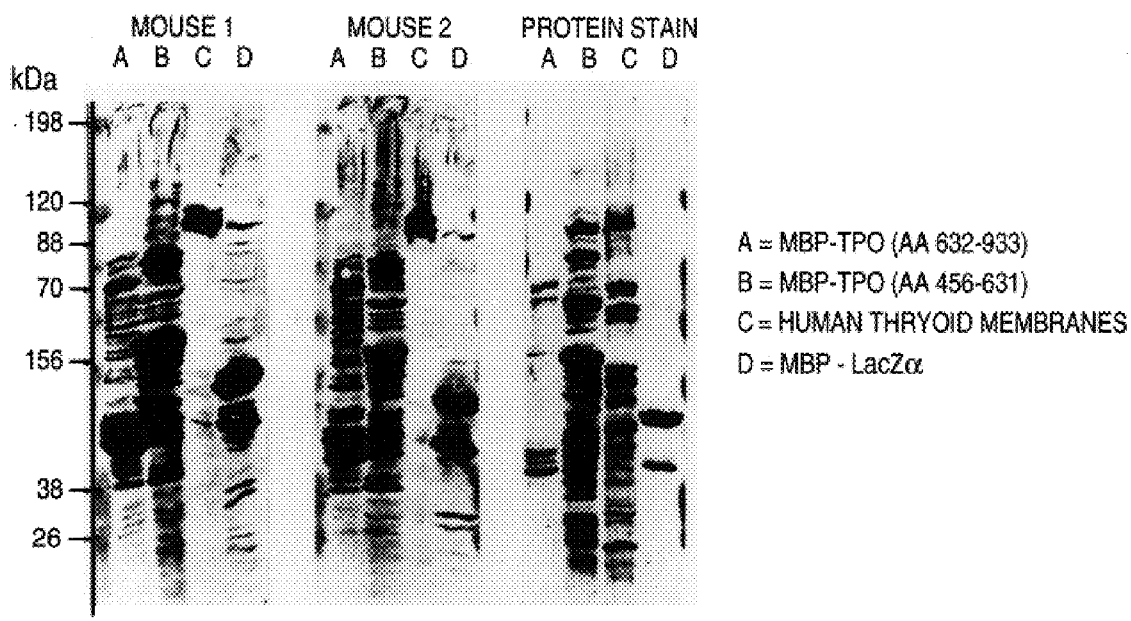
FIG. 15 is a Western blot analysis of sera from mice immunized with MBP-TPO (AA 632–933) (SEQ ID NO:1).

Induction of de novo Immune Response to Native TPO by TPO Fusion Proteins. With the finding that the fusion protein TPO fragments were immunologically recognized by the thyroid cancer patients, the characterization of the antigenicity of these constructs was expanded to determine whether the recombinant TPO fusion proteins could elicit an immunologic response to the native TPO molecule. This attribute would be essential if these constructs were to be used as immunizing agents in cancer immunotherapy. To examine the immunogenicity of the TPO constructs in animal models, three Balb-C mice received intraperitoneal immunizations with 2 mg/ml of Prep Cell purified MBP-TPO (AA 633–933) (SEQ ID NO:1) in Freund's adjuvant in an effort to produce antibodies against TPO. Serologic immune responses to the fusion protein and native TPO were evaluated in these animals. In the Western blots of FIG. 15, specific reactivity with all of the fusion proteins (lanes A and B), as well as the MBP (lane D) was shown. Most importantly, specific reactivity with TPO (lane C, 100–105 kDa band) was seen. The protein stain of the gel is shown at the right of the blot for comparison. As shown in FIG. 15, all three mice developed high titer, specific antibody to native TPO, clearly indicating the development of a serologic immune response to the fusion protein that cross-reacted with native TPO. This indicated that the TPO sequences in the fusion proteins induce antibodies reactive with the native TPO.

Figure 16:
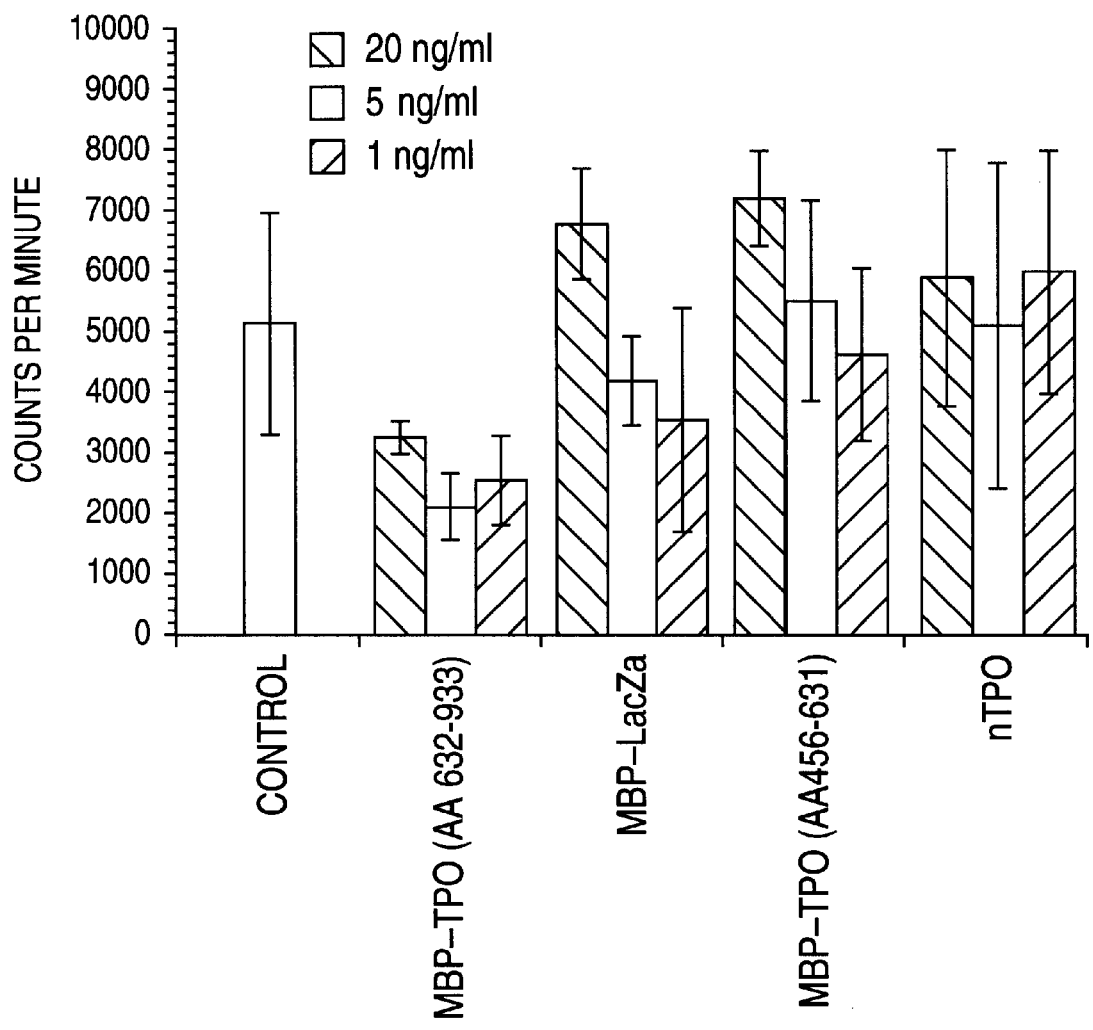
FIG. 16 is a bar graph showing the proliferation of splenocytes from a mouse immunized with MBP-TPO (AA 632–933) (SEQ ID NO:1).

The finding that these mice developed strong serologic reactivity to native TPO led to evaluation of potential cellular responses to TPO in these animals. The spleen of one of the immunized mice was harvested for a hybridoma fusion and a portion of the spleen preparation was used for cellular studies. The mouse splenocytes were immunized with Prep Cell purified MBP-TPO (AA 633–933) (SEQ ID NO:1) in complete Freund's adjuvant. This animal was documented to have developed specific antibody to native TPO through this immunization. See FIG. 15, Mouse 2. Proliferation assays were conducted using the purified fusion proteins, MBP and native TPO, as shown in FIG. 16. As might be expected in an animal recently immunized with Freund's adjuvant, there was high background (spontaneous) proliferation of the cells. This made appraisal of the proliferation to the antigens difficult. However, the results suggest that the mouse lymphocytes proliferated in response to native TPO, although not significantly when compared to background. Further studies are currently being performed with several technical modifications: the animals are immunized with the fusion proteins in the absence of Freund's adjuvant and the assays are being performed in serum free media. The cellular immune response to native TPO is then measured.

SPECIFIC EXAMPLE III—IMMUNE RESPONSE TO TPO

Further evaluation of anti-TPO responses in cancer patients provides a more definitive understanding of which immune characteristics determine the extent of a patient's response to immune stimulation with TPO and assists in screening potential recipients for TPO-based cancer vaccine.

Immunoassay Techniques for the Determination of Antibody Responses to TPO in Cancer Patients. Serologic immunity to TPO is quantified by a number of different antibody assays in order to obtain a clear understanding of degree and specificity of this response. Traditional anti-microsomal antibodies are determined by commercial agglutination assay (Ames Diagnostics). Antibodies to human TPO are determined by ELISA using Prep-Cell-purified antigen with techniques described in Weetman, A. P. et al., *Clin. Chim. Acta.* 138(3):237–244 (1984). Antibody to the localized epitopes described in Specific Example I is assayed through Western blots of MBP fusion proteins containing specific TPO amino acid sequences (see Maastricht, J. et al., *J. Clin. Endocrinol. Metab.*, accepted for publication 1992) or through ELISA using Prep Cell-purified MBP-TPO fusion proteins. The latter assay involves coating 96-well plates with 1 µg/ml of fusion protein, then blocking the plates with BSA. The patient sera is run in quadruplicate, 1:2 serial dilutions (from 1:20) in phosphate buffered saline containing an excess of purified MBP, and the end-point titer determined. A control positive and negative sera is run on each plate to standardize the inter-plate variability. Antibodies to thyroglobulin are determined using a commercial agglutination assay (Ames Diagnostics) as a measure of overall serologic immune activity to thyroid antigens.

Examination of Cellular Immune Responses to TPO in Thyroid Cancer Patients. In order to determine if cellular immune responses to TPO are present in the cancer patients being evaluated, several techniques are utilized. Proliferation in response to specific antigen is performed as previously described in Fisfalen, M. E. et al., *J. Clin. Endocrinol. Metab.* 66(4):776–784 (1988) using Prep Cell-purified native TPO isolated from thyroid microsomal fractions. See Yokoyama, N. et al., *J. Clin. Endocrinol. Metab.* 70:758–765 (1990). In addition, because of the divergent results between native and recombinant TPO in preliminary studies, at least three different MBP-TPO fusion proteins, MBP-TPO (AA 1–400) (SEQ ID NO:1), MBP-TPO (AA 376–631) (SEQ ID NO:1) and MBP-TPO (AA 456–933) (SEQ ID NO:1) are produced that will cover the entire amino acid sequence of TPO (with amino acid overlap to ensure all potential epitopes are identified). These fusion proteins are purified using the prep cell and used to stimulate peripheral blood mononuclear cells (PBMC) from the patients in a manner identical to the native TPO. Control stimulations are performed with MBP-LacZα fusion proteins. If proliferation with MBP is identified, the patients are assayed using recombinant TPO fragments separated from MBP after cleavage with Factor Xa.

Cytotoxic immunity for thyroid cells is measured with a chromium release assay using autologous thyroid cells as targets. These normal cells are isolated from normal, peri-tumor tissue in thyroidectomy specimens and grown in primary culture before labelling as described in Sack, J. et al., *Cancer* 59(11):1914–1917 (1987). TPO-specific cytotoxicity is determined using several assays. Specific production of TNF in response to antigen is performed as outlined in Flick, D. A. et al., *J. Immunol Meth.* 68:167–175 (1984), with TNF production measured at several time points after the addition of antigen. Specific cytotoxicity for TPO-targets cannot be measured using thyroid cells because of the presence of other thyroid antigens. An alternate method uses autologous EB-lymphoblastoid cells transfected with the TPO gene and selected for TPO expression. The production of these targets and the cytotoxicity assay is described under the section of this Specific Example entitled Induction and Characterization of $CD8^+$ T Cells Specific for TPO.

Determination of TPO Expression on Thyroid Cancer. TPO expression is evaluated using immunohistochemical staining techniques discussed in DeMicco, C. et al., *Cancer* 67:3036–3041 (1991). Antibodies used for this detection involve monoclonal antibodies against several portions of the TPO molecule (see DeMicco, C. et al., *Cancer* 67:3036–3041 (1991); Finke, R. et al., *J. Clin. Endocrinol. Metab.* 71:53–59 (1990); and Hamada, N. et al., *J. Clin. Endocrinol. Metab.* 61(1):120–128 (1985)) as well as hetero-antisera raised against recombinant portions of the TPO molecule (see FIG. 15). The tumor is also cultured, the cells harvested and whole cell lysate prepared and subjected to SDS-PAGE, when possible. See Baker, J. R. Jr. et al., *J. Immunol.* 140(8):2593–2599 (1988). Western blots of these lysates are performed to determine if protein is produced in vitro by these cells. If immunoreactive TPO is not detected in the tumor, the thyroid cancer cells are cultured and harvested as described in Rapoport, B. et al., *J. Clin. Endocrinol. Metab.* 58(2):332–338(1984), and RNA is isolated as described in Ledent, C. et al., *Endocrinol.* 129(3):1391–1401(1991). Northern blots of this RNA probed with labelled TPO cDNA (see Ozaki, S. et al., *Cell Immunol.* 105:301–316 (1987)) are used to detect evidence of transcription of the TPO gene, and to determine if the lack of expression is due to a defect in transcription or translation. This may indicate why the tumors have recently lost the capability to produce TPO or if tumors may be producing minimal amounts of TPO protein or protein fragments not detected through the immunohistochemical staining techniques employed.

Induction of CD4/Helper Type Cellular Immunity to TPO. Techniques to induce and amplify cellular immunity to TPO in patients with thyroid cancer should emphasize the induction of TPO-specific immunity in both CD4 and CD8 cellular subsets, as several animal tumor models have shown that the combined activity of both types of immune cells is most effective in mediating regression of established tumors. However, the methods of generating and characterizing TPO-specific immunity in CD4 and CD8 cells is markedly different, as is the interaction of each subset with antigen. Therefore, the two T cell subsets are examined separately.

$CD4^+$ T cells are thought to function by T cell antigen receptor (TCR) recognition of antigenic peptides presented in conjunction with Class II HLA molecules. This triggers the cells to produce lymphokines, such as IL2, IL4, TNF, INFγ and GM-CSF, which stimulate a number of immune functions. These lymphokines normally have minimal inherent cytotoxicity, however they induce and activate direct cytotoxicity by $CD8^+$ T cells, LAK cells and macrophages. In addition, it is possible that released lymphokines may cause autologous stimulation that results in $CD4^+$ T cells evolving into active $CD8^+$ cytotoxic T lymphocytes (CTL). Thus, $CD4^+$ cell cytotoxicity may occur through both direct and indirect means.

Induction and Expansion of TPO-specific $CD4^+$ T Cells. The induction of $CD4^+$ T cells specific for TPO is conducted on PBMC from patients with thyroid cancer. One of the advantages of studies involving $CD4^+$ T cells is the relative ease (compared to $CD8^+$ T cells) that these cells can be grown in culture. Because antigen-presenting cells will take up exogenous antigen, process and present it in conjunction with Class II MHC, soluble antigen and peripheral blood mononuclear cells are essentially the only requirements to induce growth and stimulation of $CD4^+$ T cells. However, there are many variations in this process, especially in the composition of the antigen and the type of antigen-presenting cell, that can markedly influence not only the state of activation but the type of lymphokine produced. These variables are fully evaluated in the following studies.

TPO-specific $CD4^+$ T cells are developed from PBMC which are purified from the peripheral blood of patients using Ficoll-Hypaque gradients. To produce the antigen-specific cells, approximately $1 \times 10^6$ cells/ml are incubated with purified forms of TPO antigen. These antigens include purified human TPO isolated from thyroid microsomes by the Prep Cell and recombinant TPO fragments coupled to MBP. It has previously been determined with cloning studies in autoimmune thyroiditis, that between 0.1 to 100 ng/ml of antigen should be incubated with the mononuclear cells as an optimal concentration for stimulation. See MacKenzie, W. A. et al., *J. Clin. Encrinol. Metab.* 64(4):818–824 (1987). Antigen stimulation is done for five days in RPMI media supplemented with 10% pooled normal human serum, or in serum-free media (ABC media, Pan Data Systems, Gaithersberg Md.). After the five days of stimulation, the reactive lymphoblasts are cultured for an additional seven days in media containing ten units/ml of recombinant IL2 (Genzyme, Boston Mass.) or 10% PHA supernatant of peripheral blood cells prepared as described in Higgs, J. B. et. al., *J. Immunol.* 140(11):3758–3765 (1988). After approximately seven days in IL2, the lymphoblasts are collected, washed and again stimulated with antigen for three days in the presence of irradiated, autologous peripheral blood mononuclear cells in IL2 free media. These alternating antigen/IL2 cycles are repeated approximately four to six times, with antigen stimulation always followed by IL2 stimulation.

Proliferative Response of TPO-specific T Cells. After these cycles, the cells are evaluated for antigen specificity through proliferation assays using purified antigen and irradiated antigen-presenting cells. Proliferative responses are determined using thymidine incorporation as described previously in Holoshitz, J. et al., *J. Clin. Invest.* 73(1):211–215 (1984). Approximately $15 \times 10^4$ cultured T cells and approximately $7.5 \times 10^4$ irradiated autologous PBMC are incubated together per well, with or without the antigen for approximately 72 hours. Cultures are then pulsed with $^3(H)$ thymidine and harvested as described in Holoshitz, supra. Proliferated responses are assessed by comparing CPM obtained with the antigen to CPM obtained without the antigen, and with PHA-stimulated cells serving as a positive control. A stimulation index of approximately three times background is usually considered positive. Stimulation indices of TPO antigen versus control antigen (such as tetanus toxoid) is compared to determine the enhancement of specific TPO responses achieved through the sequential stimulation cycles.

Production of TPO-specific CD4$^+$ T Cell Clones. TPO responsive cells are also cloned using previously described limiting dilution techniques. See MacKenzie, W. A. et al., *J. Clin. Endocrinol. Metab.* 64(4):818–824 (1987) and Goronzy, J. et al., *Meth. Enzmol.* 150:333–341 (1987). This technique involves Percoll density gradient purification of the viable lymphoblasts which are then re-suspended to a concentration of approximately 5 cells per 100/ml. These cells are then plated onto flat bottom 96-well microtiter plates (Costar) at approximately 100 $\mu$l per well, over feeder cells consisting of autologous, irradiated EB transformed B cells or PBMC. The autoantigen are reintroduced at a concentration ranging from approximately 1 ng/ml to 1 $\mu$g/ml. The cloned cells are then examined for proliferating cells under phase-contrast microscopy. Those cells which appear to be responding are expanded through weekly repeated stimulations with feeder cells and antigen, and are then expanded to large populations with IL2.

Phenotyping of T Cells and T Cell Clones. The surface phenotype of the successfully propagated, TPO-specific cells and clones is determined using cytofluorographic analysis as described in Lanier, L. L. et al., *Nature* 324 (6094):268–270 (1986). Antibodies include: anti-CD5 (Becton-Dickinson), OKT11 (anti-CD2, Ortho-Diagnostics), anti-leu4 (anti-CD3, Becton-Dickinson), anti-leu3α (anti-CD4, Becton-Dickinson), anti-leu2α (anti-CD8, Becton-Dickinson), WT31 (anti-α β T cell receptor, Becton-Dickinson) anti-DR (Becton-Dickinson), anti-IL2 receptor (Becton-Dickinson), TCR δ 1 (anti-TCR δ chain, T Cell Sciences) and W6-32 (anti-HLA A, B & C, Accurate Scientific). Two color staining is performed and the clones are judged positive only if greater than 90% of the cells express an antigen as compared to isotope control monoclonal antibodies labeled with the same fluorescent dye.

Localizing CD4$^+$ T Cell Epitopes in TPO. It may be important to identify the precise epitopes involved in the induction of CD4$^+$ T cell immunity to TPO. These small peptide fragments are then coupled to a number of adjuvants in order to increase their immunogenicity and augment the immune response to native TPO. The localization of these epitopes involves the production of recombinant TPO fragments. This work is conducted in a manner similar to that described in Specific Example I and Maastricht, J. et al., *J. Clin. Endocrinol. Metab.* 75:121–126 (1992). Essentially, fragments of the cDNA for TPO are produced through digestion with specific endonucleases and Polymerase Chain Reaction (PCR). These fragments are ligated, in correct frame for translation, into pMALcRI. The plasmids created are used to transform XL-1 *E. coli*, and lysates of these cells are prepared. The MBP-TPO fusion proteins are isolated from lysate by amylose affinity chromatography and preparative SDS-PAGE. These fragments are used in proliferation assays to identify which TPO fragments contain the amino acid sequences recognized by the CD4$^+$ T cells.

Once the epitope has been localized to approximately 20 amino acids using the TPO fragment fusion proteins, synthetic peptides are used to map the exact T cell recognition sequence. Because T cells normally recognize peptides of 6–12 amino acids in length, 12 amino acid peptides which overlap by 6 amino acids are constructed which correspond to suspected epitopes. The synthetic peptides are tested to determine if they induce proliferation in the TPO-specific T cell and clones. Those peptides with activity are subdivided into smaller peptides, each containing a fraction of the 12 amino acid sequence, to indicate the exact recognition site.

Alternative Studies. It is possible that despite favorable preliminary data, the recombinant proteins may not be entirely effective in inducing a TPO-specific CD4 immune response, or may only produce a response in a minority of patients. Several techniques are utilized to overcome this problem. The synthetic TPO fragments are cleaved from MBP and coupled to more potent adjuvants, such as KLH. See Bruderer, U. et al., *Immunol.* 64(3):385–390 (1988). The concentrations of these fragments may need to be varied, or several different fragments of the TPO molecule may need to be mixed together to provide adequate stimulation of many different anti-TPO T cell clones all recognizing different epitopes. Different types of antigen presenting cells may also be important in the induction of CD4 responses. Dendritic cells are more effective in presenting antigen than normal macrophages and are isolated from peripheral blood using monoclonal antibodies and flow cytometry, or preferably with monoclonal antibody-coated magnetic beads (Dynal). Normal, autologous thyroid cells may be useful in this context, especially if Class II antigens are induced with γ-interferon. In addition, it is possible that EB-transformed lymphoblastoid cells are a superior method for stimulating CD4 cells. These options are exercised if initial attempts to induce TPO-specific CD4 cells are not successful.

A major factor guiding the in vitro production of CD4 immunity may be the natural development of anti-TPO immunity in cancer patients in vivo. In this regard, studies previously discussed in this Specific Example, should serve as an indication of the degree of CD4+ T cell sensitization and its relation to tumor TPO expression. Once the prevalence of this immunity is established, through the evaluation of large numbers of patients, subsequent studies focus on the specific conditions which affect the development of TPO-specific CD4+ T cell responses in vivo. In relation to this, several clinical factors are closely examined: tumor histology, stage, evidence of metastasis, nutritional status and prior treatments. It is possible that the anti-TPO response is maximal early in the course of the disease, and becomes attenuated by the presence of increased tumor burden, metastasis and chemotherapy. To maximize the yield of TPO-specific precursor CD4+ T cells for in vitro manipulation or expansion, it is important to understand the relationship between the tumor and anti-TPO responses and address whether endogenous TPO-specific CD4+ T cells immune responses modulate the biology of autologous tumors in vivo.

Induction and Characterization of CD8+ T Cells Specific for TPO. Cytotoxicity of tumor cells by Class I MHC-restricted CD8+ cells has been demonstrated in a number of tumor models. See Mitsuya, H. et al., *J. Exp. Med.* 158:(3):994–999 (1983) and Anichini, A. et al., *J. Immunol.* 142 (10):3692–3701 (1989). While technical problems are encountered in generating these cells, they offer the possibility of direct tumor lysis using restriction elements (Class I MHC antigens) and target antigens already present in the tumor cells. Because Class I antigens preferentially express endogenously-derived peptides to the exclusion of exogenous ones as discussed in Germain, R. N., *Nature* 322 (6081):687–689 (1986); Berzofsky, J. A. et al., *Immunol. Rev.* 106:5–31 (1988); and Grey, H. M. et al., *Sci. Am.* 261(5):56–64 (1989), they will tightly restrict the response to the desired target cells. Because this process is so markedly different from CD4+ T cell recognition of antigen, this experiment is devoted exclusively to an examination of CD8+ T cell recognition of TPO-bearing cells and the function of these cells in mediating tumor lysis.

Preliminary studies have demonstrated peripheral blood and intrathyroidal lymphocytes from cancer patients to be sensitized to TPO in vivo. However, to detect antigen-specific CTL, it is usually necessary to re-stimulate cells in vitro to induce functional CTL. In general, these studies involve the isolation of CD8+ T cells from thyroid cancer patients, their stimulation with various types of cells bearing different forms of TPO and a determination of the CTL activity induced by these stimulations. A major consideration is the supplementation of the growth of the CD8 cells in culture with exogenous cytokines. This is essential because CD8+ T cells do not produce adequate quantities of autocrine factors to support their own growth. In this regard, different combinations of supernatant fluid from activated lymphocytes, irradiated feeder cells and specific lymphokines (such as low dose, $\leq 10\,\mu$lU, recombinant IL2) is added to support the growth of these cells. Techniques for inducing large numbers of TPO antigen-specific cytotoxic T lymphocytes, either in vitro or in vivo are thus developed.

Induction of TPO-specific CD8+ CTL in vitro by TPO-bearing Thyroid Cancer Cells. A major hypothesis of this study is that thyroid cancer cells expressing TPO protein can be lysed by CTL-specific for tumor-associated TPO. The ability of these same cells to elicit this type of response prompts the investigation of the induction of a TPO-specific CTL response. Tumor cells are isolated from thyroidectomy specimens through mechanical isolation of the tumor followed by enzymatic digestion as described in Rapoport, B. et al., *Metabolism* 31:1159–1167 (1982). These cells are cultured for at least 6–8 passages in vitro, and the tumor cells bearing TPO are isolated with FACS or magnetic beads and anti-TPO. Approximately $1\times 10^5$ tumor cells are co-cultured for 4–6 days with $4\times 10^5$ CD8+ cells in the presence of various concentrations of IL2 and feeder cells. The CD8+ cells are isolated from PBMC using magnetic beads (Dynal) with either anti-CD8 (for positive selection) or anti-CD4 (for negative selection). The growth of these cells is monitored and surface markers, such as LFA-1, CD2, and other molecules involved in adhesion for cytolysis are identified through FACS. Other combinations of cytokines may include IL4 in place of IL2 to prevent the potential induction of non-specific LAK cells (see Kawakami, Y. et al., *Exp. Med.* 168(6):2183–2191 (1988)), or the addition of such factors as INFγ, IL-1, TNFα or supernatant fluid from mitogen (PHA) stimulated lymphocytes, if the initial conditions are not adequate to induce TPO-specific CTL activity.

Induction of TPO-specific CTL by Autologous Non-tumor Cells Incubated with Synthetic TPO Peptides. Although thyroid cancer cells may be very effectively lysed by CD8+ CTL, the tumor cells may not be appropriate cells to use to stimulate the generation of these cells. Various cytokines elaborated by tumors, such as TGFβ, can inhibit the differentiation of CTL. See Wrann, M. et al., *EMBO J.* 6:1633–1636 (1987) and Ranges, G. E. et al., *J. Exp. Med.* 166(4):991–998 (1987). The presence of extraneous, non-tumor specific antigens presented aberrantly by the tumor cells may obscure the detection of an anti-TPO response. Some of the determinants from these antigens may preferentially bind to Class I antigens and block binding of TPO peptides, thereby preventing the generation of an anti-TPO response. If specific, synthetic TPO fragments are not generated, the difficulties with using tumor cells are overcome by using normal cells that do not endogenously express TPO. Under certain circumstances extra-cellular soluble peptides can bind to Class I molecules as discussed in Townsend, A. R. et al., *Cell* 44(6):959–968 (1986). While the Class I molecules are normally occupied by cell peptides (see Bjorkman, P. J. et al., *Nature* 329(6139):506–512 (1987)), some alterations in culture conditions, such as culture at 27° C., results in the expression of Class I antigens without endogenous peptides. See Ljunggren, H. G. et al., *Nature* 346(6283):476–480 (1990) and Shumacher, T. N. et al., *Cell* 62(3):563–567 (1990). The addition of TPO peptides to these cells, especially accompanied by β-2-microglobulin as discussed in Kozlowski, S. et al., *Nature* 349(6304):74–77 (1991), may allow adequate amounts of complexes to form so that these cells can then present TPO peptides to CD8+ T cells. Possible cell lines used for this include autologous fibroblasts, grown from the surgical thyroidectomy specimen, or autologous EB-transformed lymphocytes. Both of these cells express Class I molecules, and since they are autologous, would share the same Class I allotype. These cells are different in that the lymphoblastoid cells can constitutively express Class I MHC while the fibroblasts do not. The effect of the differences in expression of these molecules or other differences in these cells on CTL generation is unknown, and is one parameter that can be monitored in these studies to provide important general insights into the induction of antigen-specific CTL.

The TPO peptides used to coat these cells are produced from the MBP-TPO (AA 456–933) fusion proteins. The TPO-specific areas are isolated by cleavage with Factor Xα, and then are manipulated by heat denaturation, detergent or protease treatment before being added to the culture to yield peptides of TPO that will bind to the Class I MHC antigens. Truncated versions of these peptides, produced from fusion proteins like MBP-TPO 456–631 (SEQ ID NO:1), are also employed to better define the specific CD8+ T cell epitopes, and eventually yield a more specific and intense CTL response. If the specific epitopes are determined in this manner, synthetic peptides are then used to replace the fusion-protein derived TPO sequences.

Induction of TPO-specific CTL Activity by Cells Transformed with Viral Vectors Containing TPO cDNA. One of the advantages of having the full-length cDNA for TPO is that it can be used with a number of eukaryotic vectors to express the TPO protein in cells where this antigen is not normally found. The TPO cDNA may be placed into several vectors as described in Wilson, J. M. et al., Science 248 (4961):1413–1416 (1990) and Shigekawa, K. et al., Biotechniques 6:742–751 (1988), for expression in several types of autologous cells from the patients and produce cells with endogenous expression of TPO. After transformation, these cells are selected with G418, the common name referencing geneticin, as sold by Sigma Chemical, and those cells expressing large quantities are identified and isolated using FACS and monoclonal anti-TPO. This results in non-thyroid cells, such as fibroblasts, over-expressing TPO, and may provide important cells for the induction of CTL. EB-lymphoblastoid cells expressing TPO have both Class I and Class II MHC antigens, and can also be used to induce both CD4+ and CD8+ anti-TPO immune responses. These cells can also provide targets to identify TPO-specific CTL activity, as control cells transformed with vectors expressing irrelevant or no protein can be easily generated. Using these cells to induce CTL activity provides a unique approach resulting from a cloned and expressible tumor antigen.

Determination of Cytotoxicity against TPO Target Cells. Cytotoxicity against in vitro cultured thyroid cells, thyroid cancer cells or TPO gene-transfected target cells is assessed using $^{51}$Cr release assay as described in Sack, J. et al., J. Clin. Endocrinol. Metab. 62(5):1059–1064 (1986). Thus cells are incubated with $^{51}$Cr for labeling. Excess chromium is washed off and these labelled target cells are mixed with cloned CD8+ T cells at various target ratios for 4 hours at 37° C., in a humidified atmosphere of 5% $CO_2$. Supernatant fluids are harvested and counted in a gamma counter, each effector/target ratio determined in triplicate and the data presented as specific $^{51}$Cr release measured as the experimental release minus spontaneous background over the total counts present minus spontaneous background×100, thereby giving the ratio of reactivity. The total counts releasable is determined by mixing the cells in 1% Triton×100. Spontaneous release is determined by measuring the $^{51}$Cr release of the target cells cultured in media alone without cytotoxic cells. To document the MHC Class I restriction of CTL by the CD8+ T cell clones, blocking experiments with monoclonal antibodies against Class I or Class II antigens (as controls) are also conducted. Results are collected and analyzed to determine the specific requirements for Class I antigens necessary for TPO antigen-specific CTL.

Evaluation of Molecular Elements Involved in CD8 Recognition and Binding to Tumor Cells. Determining the exact epitopes in TPO that are recognized by the CD8+ T cells is of primary importance. While it might be possible to generate anti-TPO activity in vitro with synthetic TPO, the CD8 target epitopes must be present on the cancer cells to make cytotoxic immunity effective. Using the recombinant fusion proteins and synthetic peptides described previously will allow the identification of the specific portions of the TPO molecule recognized by the CD8 cells, and allow the determination of whether each tumor express a particular TPO epitope.

It is possible that the CTL lysis may be restricted to certain MHC Class I allotypes, either because of the inability to bind TPO peptides or the inability of the MHC-TPO peptide complex to be recognized by CD8 T cell antigen receptors. If this appears to be the case, cells from patients who appear able to present TPO peptides are tissue typed and the specific allotypes necessary to present these antigens are identified. This allows screening of patients who are most likely to respond to therapy with this antigen.

Effect of TPO on Lymphokine Production by T Cell Clones. Because of the important function lymphokines are believed to play in the induction of cytotoxic immunity to cancer cells, it is important to determine whether the T cells and T cell clones produce lymphokines in response to specific stimulation with antigen. Commercial immunoassays for TSH, IL2, IL4, IL5, IL6, TNF and interferon γ are run on antigen-stimulated T cell clone supernatant fluid to determine whether or not these lymphokines are produced by the clones. Bioassays for lymphokines with more generalized actions that may mediate direct cytotoxic actions, such as TNF discussed in Flick, D. A. et al., J. Immunol. Meth. 68:167–175 (1984), and IL6 discussed in Ida, N. et al., J. Immunol. Methods 133(2):279–284 (1990), are also performed.

In some situations, lymphokines that are membrane bound or are delivered in local interactions between CTL and target cells may play an important role in cytotoxicity but may not be detectable in supernatant fluid. To attempt to identify these factors, the activation of transcription of the genes for IL2, IL3, IL4, IL5, IL6, interferon γ and TNF in the T cell and clones is determined using PCR techniques. The PCR studies involve the cells being isolated and lysed with 100 μl of GITC (guanidine-isothiocyanate) solution with the resulting fluid loaded onto a 100 μl cesium chloride gradient in ultracentrifuged tubes. These tubes are spun at 80,000 RPM for 2 hours at 20° C., after which the supernatant fluid is aspirated and the pellet combined with 100 μl of DEPC (i.e. diethylpyrocarbonate) treated water to resuspend the RNA. Potassium acetate (10 μl) is added to the tubes and the RNA is cold ethanol precipitated. The precipitate is then washed with 80% ethanol and the samples are air-dried. AMv reverse transcriptase will be used to produce first strand DNA from approximately 100 ng of RNA in a 50 μl reaction at 37° for 1 hour as described in Okayama, H. et al., Mol. Cell. Biol. 2(2):161–170 (1982). Ten μl of first strand cDNA is mixed with 80 μl of PCR mix (containing dNTP's mix, 200 mM and Taq polymerase, 2.5 units per assay tube, Perkin Elmer/Cetus). Five μl of primers for each lymphokine is added to each tube to give a final primer concentration of 1 μM. The mixture is then subjected to PCR amplification using the Perkin-Elmer thermocycler. An ethidium bromide stained 2% agarose gel is used to separate the PCR fragments. Inclusion of a sample from a cell line known to transcribe the assayed lymphokine (e.g., Jurkat cells for IL2) is used as a positive control for each experiment. For a negative control, "mock" reverse transcription reactions are performed on RNA by omitting the reverse transcriptase enzyme and subjecting this mixture to PCR. In this way, the activation of lymphokine transcription induced by antigen is determined even in the very slight lymphokine release from the cells (on the order of μM).

Effect of Lymphokines on Thyroid Cancer Cell Function. Assays of thyroid cell function using thyroid cancer cells in primary culture are carried out whenever adequate numbers of cells are obtained from surgical specimens. The cancer cells are cultured with supernatant fluids from CD4+ and CD8+ T cells and T cell clones. Determinations of the effect of the lymphokines include the quantitation of cAMP produced by the cancer cells as discussed in Vitti, P. et al., *J. Clin. Endocrinol. Metab.* 57(4):782–791 (1983), and the ability to suppress thyroid cancer cell growth as measured by the induction of DNA synthesis in the measurement of $^3$H thymidine incorporation as described in Valente, W. A. et al., *N. Engl. J. Med.* 309(17):1028–1034 (1983). In addition, the ability of the T cell supernatant lymphokines to suppress cancer cell production of immune-blocking factors, such as TGFβ (see Lucas, C. et al., *Methods Enzymol.* 198:303–316 (1991)) and thyroglobulin (see Feldman, A. et al., *Clin. Endocrinol.* (Oxf.) 25(1):45–53 (1986)), is also assessed. Several lymphokines and cytokines have been reported to have effects on thyroid cells that may either potentiate or suppress cytotoxic actions. IL6 has been reported to suppress TPO expression in normal thyroid cells in Tominaga, Y. et al., *Acta Endocrinol.* (Copenh.) 124(3):290–294 (1991), and this would be detrimental in TPO-directed cytotoxic therapy if true in cancer cells. Thus, the effects of these cytokines on thyroid cancer cells is important.

Induction of TPO Antigen-Specific TIL Cells from Thyroid Cancer. The induction of TPO-specific immune cells from TIL offers unique potentials and problems. The TIL cells have great potential for use in TPO-specific immunotherapy, as a proportion of the cells were drawn to the tumor site and their numbers expanded due to their reactivity with TPO and other tumor antigens. In addition, there is likely to be preformed CTL cells or other cells capable of mediating tumor lysis. This is supported by the findings in Specific Example II, where these cells produced TNF in response to stimulation with TPO. Because of this, many of the studies outlined in this Specific Example are performed on the tumor infiltrating lymphocytes harvested from the patients thyroidectomy specimens. However, while the problems outlined in these sections certainly apply to the TIL cells, there are other considerations that make the generation of CTL from the TIL cells unique. Because this is an inflamed area, non-specific LAK and CTL activity are likely the major response, and are separated from the anti-TPO activity. This likely requires the use of different lymphokine for stimulation of antigen-specific immunity, and the cloning of all of these cells at an earlier stage of development. Also, the limited number of cells obtained from these tumors may require greater expansion of the cell populations. Thus, although similar studies are performed on the TIL cells, they require different conditions and techniques to be successful.

The differences in culture conditions for the TIL cells revolves around the initial conditions for growth, in vitro. The cells can be cultured as whole, enzymatic digests of thyroid tumors, purposely keeping the cancer cells present as a source of antigen and tissue dendritic cells to present antigen. Alternatively, T cells are isolated from the digested tumor through anti-T cell monoclonal antibody-labelled magnetic beads (Dynal), and cultured either with purified antigen or irradiated tumor cells in the presence of low-dose IL2 (<10 U/ml) and possibly IL4 (to inhibit the LAK activity). The cells expanded by these techniques are then evaluated as outlined above.

In Vivo Models. In addition to Hashimoto patients as human models for TPO immunotherapy, in vivo models of thyroid cancer are used to evaluate its efficacy. Implantation of thyroid cancer (thyroidectomy) specimens into SCID/human mice is employed because in comparison to previous models, this model will more closely replicate human disease. Since the immune cells in these thyroid glands should include a percentage of anti-TPO T cells, the immune system of the mouse provides an in vivo model to study immune system stimulation. Tumor regression can then be monitored as a measure of efficacy.

SPECIFIC EXAMPLE IV

TPO AUTOANTIBODY RESPONSES IN GRAVES' AND HASHIMOTO'S PATIENTS

Two disorders with markedly different clinical presentations, Graves' disease and Hashimoto's thyroiditis, are both associated with autoantibodies to the microsomal antigen, now identified as the enzyme thyroid peroxidase (TPO). Libert, F. et al., *EMBO J.* 6:4193–4196 (1987); Portmann, L. et al., *J. Clin. Endocrinol. Metab.* 61:1001–3 (1985). Characterizing the immune response to this antigen in patients with these two diseases may help clarify differences in the pathogenesis of the autoimmune thyroid diseases (AITD) and facilitate more accurate diagnosis of thyroid disorders.

Recently published studies have suggested that autoantibodies directed against TPO are heterogeneous in nature. Localized autoantibody binding to a region between amino acids 590 and 675 (SEQ ID NO:1), and between amino acids 700 and 933 (SEQ ID NO:1) have been reported [Libert, F. et al., *EMBO J.* 6:4193–4196 (1987); Libert, F. et al., *J. Clin. Endocrinol. Metab.* 73:857–60 (1991); Nakajima, Y. et al., *Mol. Cell Endocrinol.* 53:15–23 (1987)] and the sizes of the TPO peptide fragments examined in these studies were small enough to suggest that these epitopes were not conformational. Several other reports using purified native TPO have suggested that there may be multiple autoantibody epitopes, some of which are conformational. Doble, N. D. et al., *Immunology* 64:23–29 (1988); Yokoyama, N. et al, *J. Clin. Endocrinol. Metab.* 70:758–65 (1990); Finke, R. et al, *J. Clin. Endocrinol. Metab.* 73:919–21 (1991). Previous work has demonstrated localized autoantibody epitopes in the portion of the human TPO molecule from amino acids 456 to 933, and suggested the presence of multiple binding sites. See Maastricht, J. et al, *J. Clin. Endocrinol. Metab.* 75:121–26 (1992).

In the present invention, the serologic immune response to native thyroid microsomal antigen, denatured and reduced microsomal antigen, and several recombinant peptide fragments of human TPO in patients with Graves' disease and Hashimoto's thyroiditis was characterized. The results were then correlated to measures of clinical disease activity in order to determine if clinical subgroups or associations related to specific types of anti-TPO activity.

Overview. In order to examine the specificity of the autoantibody response to thyroid peroxidase in autoimmune thyroid disease, the reactivity of sera from 45 Hashimoto's and 48 Graves' patients to native thyroid microsome, denatured and reduced human TPO and several recombinant fragments of human TPO corresponding to amino acids 457–933 of the native protein were examined. Both Graves' and Hashimoto's sera bound native, denatured and reduced TPO at significantly greater rates than normal controls, and no differences were noted between the two disorders in binding to these forms of the autoantigen. Binding was also noted to two recombinant fragments of TPO, corresponding to amino acids 513–633 and 633–933 in TPO. The frequency of autoantibodies to the TPO(633–933)region was not significantly different in Hashimoto's vs. Graves' disease patients (58% vs. 65% respectively), and appeared to relate to evidence of glandular inflammation in the Graves' patients (goiter, presence of anti-thyroglobulin antibodies and elevated FT3 levels). In contrast, antibodies to the TPO(AA 513–633) (SEQ ID NO:1) fragment were significantly more common in Hashimoto's vs. Graves' disease patients (53% vs. 23% respectively), and did not correlate with any measure of glandular inflammation. These results identify two specific regions of TPO autoantibody binding and indicate that there are differences in the autoantibody response to TPO in Hashimoto's and Graves' diseases.

Materials and Methods

Patient Sera. Forty-five patients with Hashimoto's disease, forty-eight patients with Graves' disease and twenty-five age and gender-matched normal controls were enrolled in the study. The Hashimoto's patients were diagnosed on the basis of anti-microsomal antibody titers of greater than or equal to 1:400 by agglutination assay in the presence of either goiter or hypothyroidism. The age of the patients ranged from 12 to 77 years. The Graves' patients were diagnosed on the basis of clinical and biochemical evidence of hyperthyroidism (suppressed TSH with elevated T4), diffuse goiter and an increased 24 hour radioiodine uptake. None of the controls had clinical evidence or a past history of thyroid disease. Sera were obtained at the time of enrollment, and frozen at −70° until use.

Construction Of TPO Expression Plasmids. The plasmid pMaITPO(457–933) (SEQ ID NO:1) was developed from pMaIcRI (New England Biolabs) and contains (in-frame) the cDNA coding for TPO AA 457–933 (SEQ ID NO:1), as has been previously reported. Maastricht, J. et al, *J. Clin. Endocrinol. Metab.* 75:121–26 (1992). This construct encodes a fusion protein in which the amino terminal portion is maltose binding protein minus its leader sequence, followed first by the sequence IEGRISEF (SEQ ID NO:10) (one letter amino acid code), then the fragment of human TPO. This vector was used to make several new constructs containing fragments of the coding region of the human TPO cDNA from amino acids 457–933 (SEQ ID NO:1). The plasmid pMaITPO(457–633) (SEQ ID NO:1) was developed by digestion of pMaITPO(457–933) (SEQ ID NO:1) with ClaI and XbaI. The linearized plasmid was separated from the excised fragment by agarose gel electrophoresis and the plasmid was ligated to the adapter 5'-CGATTAGGTAGGTAGT (SEQ ID NO:11) (top strand), which recreates the ClaI and XbaI sites and inserts a stop codon after amino acid 633. The plasmid pMaITPO (633–933) (SEQ ID NO:1) was developed by digestion of pMaITPO(AA 457–933) (SEQ ID NO:1) with EcoRI and ClaI with the deletion of the excised fragment followed by Klenow fill-in and religation. The plasmid pMaITPO(AA 513–633) (SEQ ID NO:1) was created by digestion of pMaITPO(AA 457–633) (SEQ ID NO:1) with EcoRI and Smal followed by ligation to the adapter 5'-AATTCGACCTGCCC (SEQ ID NO:12) (top strand). The plasmid pMaITPO(AA 457–517) (SEQ ID NO:1) was created by digestion of pMaITPO(AA 457–633) (SEQ ID NO:12) with SmaI and XbaI, isolation of the linearized plasmid and ligation to the oligonucleotide adapter 5'-GGGCTGTAGT (SEQ ID NO:13) (top strand). Each construct was confirmed by restriction digestion and DNA sequencing of the 5' ligation junction.

Expression and Purification of Fusion Proteins. The plasmid constructs were used to transform *E. coli* HB 101, grown, harvested, lysed, and sonicated as previously described in the art. Maastricht, J. et al.,*J. Clin. Endocrinol. Metab.* 75:121–26 (1992). The lysate was run over an amylose affinity column to isolate the MBP fusion proteins in accordance with the vendor's protocol, and the fusion proteins were then eluted using column buffer with 10 mM Maltose.

Preparation of Thyroid Microsomal Antigen. Human microsomal antigen was isolated from normal human thyroid tissue obtained under informed consent from thyroidectomy samples as previously reported in the art. Finke, R. et al., *J. Clin. Endocrinol. Metab.* 73:919–21 (1991).

SDS-PAGE and Western Blots. Thyroid microsomal antigen or MBP-TPO fusion proteins were diluted with buffer consisting of 0.125 M Tris pH 6.8 with 4% SDS and 20% glycerol to a concentration of approximately 3 mg/ml. Approximately 500 μl of this solution was loaded into a single preparative well and electrophoresed through an 8% SDS Polyacrylamide gel. For the reducing gels and in all of the MBP-TPO samples, 10% β-mercaptoethanol was added to the sample buffer, and the samples were boiled for 5 minutes before electrophoresis. After electrophoresis, proteins were electro-transferred to nitrocellulose membranes, and these membranes were then blocked with 3% BSA in PBS for two hours at 27° C. Western blots were then performed using a 1:400 dilution of patient sera in PBS with 1% BSA and 0.01% sodium azide. Maastricht, J. et al, *J. Clin. Endocrinol. Metab.* 75:121–26 (1992). For the blots using the fusion protein, the sera were pre-incubated for 3 hours with maltose binding protein-LacZ fusion proteins (0.1 mg/ml) to block any potential reactivity to the maltose binding protein portion of the TPO fusion proteins. Controls included a monoclonal antibodies to thyroid peroxidase and MBP to identify the TPO-specific and MBP-specific bands. Ten patients with high titer anti-nuclear antibodies (ANA>1:6400) randomly selected from the clinical laboratory were also evaluated in the Western blot assays to determine the disease specificity of TPO autoantibodies.

Clinical Measurements. Thyroid function tests (including FT4, FT3, TSH) and thyroglobulin and thyroid microsomal antibody titers were performed on either identical serum samples used for Western blots or repeat samples drawn within 2 months of the original sample. The thyroid functions were performed in a routine clinical laboratory, while the TSH levels were determined by a sensitive, second generation fluorescence immunoassay. Thyroglobulin and microsomal antibody titers were determined by agglutination assay (Ames Diagnostics, Ames, Iowa). Goiter size and degree of opthalmopathy were determined by an individual who was unaware of the TPO reactivity of the subjects.

Statistical Analyses. The rates of reactivity to different areas of TPO in the Graves' and Hashimoto's disease patients, and the normal subjects were compared by Fisher's exact test. The continuous variables were compared by using ANOVA.

Results

Reactivity to Denatured and Reduced TPO. As previously reported (Hamada, N. et al, *J. Clin. Invest.* 79:819–25 (1987)), a band of approximately 220 kDa in immunoblots was identified as the non-reduced form of TPO. Under reducing conditions, antibodies against TPO identified three bands ranging from 100–105 kDa. Similar patterns of reactivity to these bands was noted in both the Hashimoto's and Graves' patients. As shown in Table 1, the frequency of reactivity of the Hashimoto's and Graves' sera were statistically identical to each other, but markedly greater than that of the control sera.

TABLE 1

| TPO Form | Normal Controls | Graves' Disease | Hashimoto's Disease |
| --- | --- | --- | --- |
| Denatured TPO | 3/21 (14%) | 40/48 (83%) * | 34/45 (76%) * |
| Reduced TPO | 1/21 (5%) | 23/48 (48%) * | 27/45 (60%) * |
| TPO (513–633) | 1/25 (4%) | 11/48 (23%) * | 24/45 (53%) *‡ |
| TPO (633–933) | 2/25 (8%) | 31/48 (64%) * | 26/45 (58%) * |
| Both Fragments | 0/25 (0%) | 9/48 (19%) * | 12/45 (27%) * |
| Either Fragment | 2/25 (8%) | 33/48 (69%) * | 38/45 (84%) * |

*P < 0.05 vs. Normals
*P < 0.01 vs. Graves'

Autoantibodies against the TPO Fragments. Initial studies failed to demonstrate serologic reactivity with the fragment TPO(AA 457–517) (SEQ ID NO:1) in any of the patient sera, while immunoblots done with either TPO(AA 457–633) (SEQ ID NO:1) or (AA 513–633) (SEQ ID NO:1) showed identical patterns of reactivity. Therefore, the TPO (AA 513–633) (SEQ ID NO:1) region was presumed to contain the autoantibody binding site between amino acids 457–633 (SEQ ID NO:1). Of the 45 Hashimoto's patients studied, 24 (53%) showed reactivity to TPO(AA 513–633) (SEQ ID NO:1), while in the Graves' group, only 11 of the 48 patients (23%) reacted to this region.

Figure 17A:
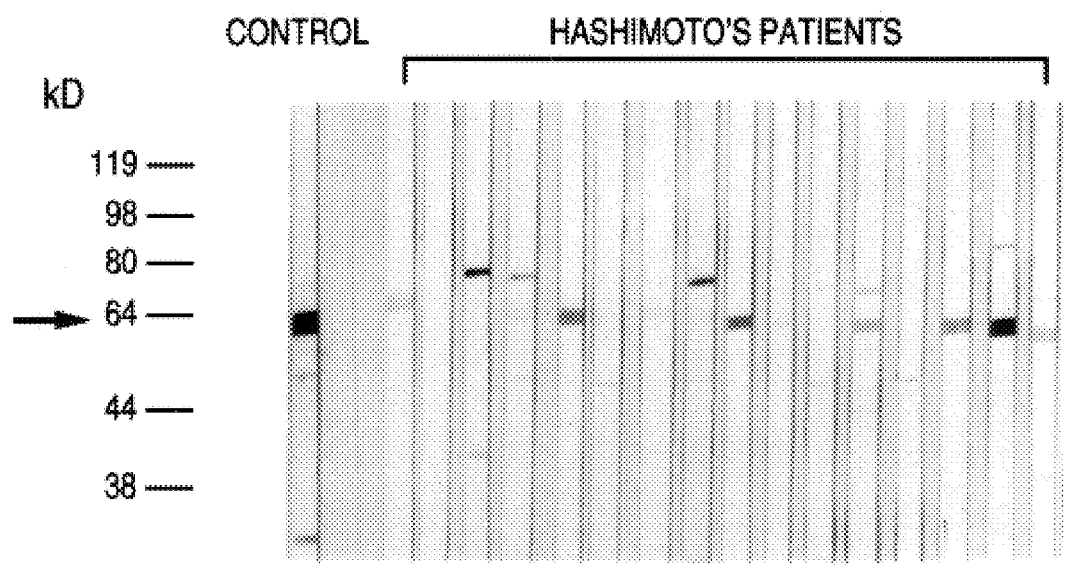
FIGS. 17A and 17B are representative Western blots demonstrating autoantibody reactivity to recombinant TPO (AA 513–633) (SEQ ID NO:1).
Figure 17B:
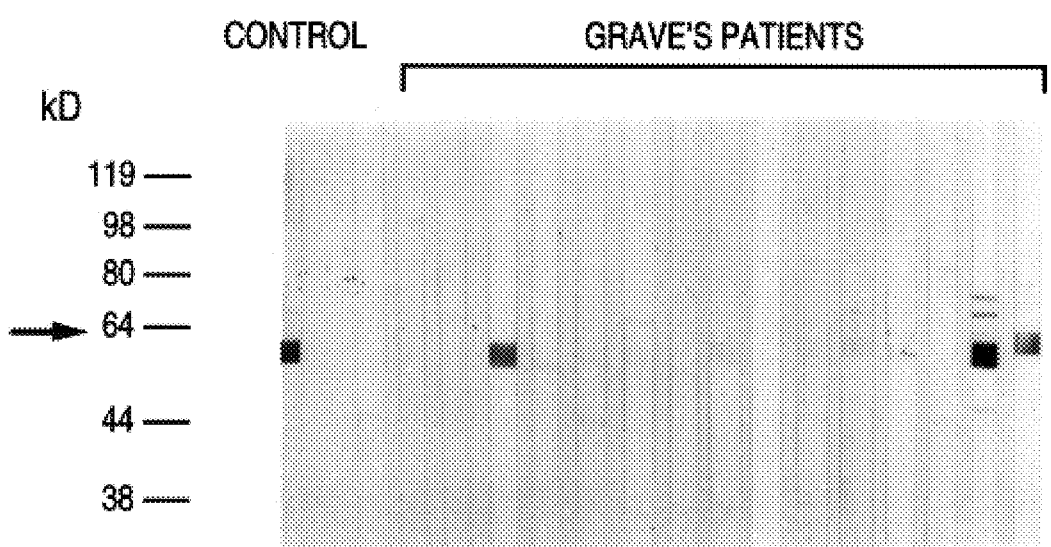

FIGS. 17A and 17B are representative Western blots demonstrating autoantibody reactivity to recombinant TPO (AA 513–633) (SEQ ID NO:1). Sera from Hashimoto's patients (Panel A) and from Graves' patients (Panel B) showed intense reactivity with the fusion protein at 56 kDa (arrow). Control (+) is an anti-MBP antiserum used to identify the location of the fusion protein (arrow). Blots using a control MBP fusion protein indicated no patient binding (data not shown). As shown in Table 1, this difference was highly significant. Only one of the normal controls reacted to TPO(AA 513–633) (SEQ ID NO:1), and the blot showed minimal intensity. In contrast, the frequency of autoantibody reactivity to TPO(AA 633–933) (SEQ ID NO:1) was similar in both the Hashimoto's and Graves' patients. Also, there was no significant difference in reactivity to TPO(AA 513–633) (SEQ ID NO:1) based on whether the patient recognized denatured and reduced TPO, while the TPO(AA 633–933) (SEQ ID NO:1) fragment was recognized at significantly higher rates in patients reactive to denatured/reduced TPO (p<0.05). This suggests an association between autoantibody binding to denatured and reduced TPO and antibodies to the TPO(AA 633–933) (SEQ ID NO:1) region which is not seen with antibodies to the TPO(513–633) (SEQ ID NO:1) region. Of interest, the microsomal antibody titer (as determined by the agglutination assay) did not correlate with binding to either region of TPO or reduced TPO by Western blot in either patient group. Also, none of the 10 control patients with SLE bound to either fragment, suggesting these autoantibodies were disease-specific.

Clinical Correlation with TPO Reactivity. For the Hashimoto's patients, there was no significant correlation between any of the clinical parameters (age, goiter size, anti-microsomal antibody titers and anti-thyroglobulin antibody titers (by agglutination assay) or hypothyroidism) and reactivity to either the recombinant fragments, or the reduced or non-reduced forms of TPO. In the Graves' patients, no statistically significant correlation was seen between age, FT4, $^{131}$I uptake, or antimicrosomal antibodies and reactivity to the two regions of TPO or to the reduced and denatured forms of TPO. Correlations were noted between reactivity to reduced TPO and the following parameters in Graves' patients; the presence of anti-thyroglobulin antibody titers (P=0.04), with higher levels of FT3 (P=0.001) and larger goiters (P=0.04). There was no correlation between the presence of ophthalmopathy and reactivity to any portion of TPO. The cDNA for human TPO used for the initial MBP construct was a gracious gift of Dr. Basil Rapoport and has been accorded GenBank Accession Number J02969.

Discussion

These results indicate that the autoantibody response to TPO is truly heterogeneous and that there are at least two localized areas in TPO that are recognized by autoantibodies from a majority of patients with AITD. The recognition of one of the areas, corresponding to amino acids 513–633 (SEQ ID NO:1), was more frequently seen in Hashimoto's disease than Graves' disease. Sera from patients with Hashimoto's disease were equally likely to be reactive to TPO (AA 513–633) (SEQ ID NO:1) and TPO(AA 633–933) (SEQ ID NO:1) while, amongst the Graves' patients, the frequency of reactivity to TPO(AA 633–933) (SEQ ID NO:1) was 3 times higher than to TPO(AA 513–633) (SEQ ID NO:1). This difference did not appear to be the result of differences in the overall serologic response to TPO, as there was no difference between the two disorders in the titer of antibodies to anti-microsomal antigen (by agglutination assay) or reduced and denatured TPO (by Western blot). Thus, the present invention shows that autoantibodies against TPO amino acids 513–633 are observed more often in Hashimoto's thyroiditis patients as compared to Graves' disease patients.

Specific Example IV of the present invention is thus in direct contrast to the findings of Zanelli, which shows autoantibody binding to all portions of TPO with no difference between Graves' and Hashimoto's patients. (Zanelli, E. et al., *Clin. Exp. Immunol.*87:80–86 (1992)) Note, that the Western blots in Zanelli's studies used sera at a high concentration (1:25 dilution) and did not compare patient binding to normal controls. Therefore, it is difficult to determine if Zanelli (and colleagues) identified autoantibodies specific for autoimmune thyroid disease.

The reason for the association of autoantibodies to the TPO(AA 513–633) (SEQ ID NO:1) with Hashimoto's disease is not clear. It has been speculated that antibodies to localized or sequential autoantigen epitopes are a consequence of denaturation and unfolding of autoantigens. Laver, W. G. et al., *Cell* 61:553–56 (1990). Inflammation of the thyroid gland unique to Hashimoto's disease might result in the denaturation of TPO, which would then result in antibodies to TPO(AA 513–633) (SEQ ID NO:1). However, the reactivity to TPO(AA 633–933) (SEQ ID NO:1) region and to reduced and denatured TPO was not different between Graves' and Hashimoto's patients. In addition, unlike autoantibodies to TPO(AA 633–933) (SEQ ID NO:1), antibodies to the TPO(AA 513–633) (SEQ ID NO:1) fragment did not correlate with serologic reactivity to denatured TPO in the Hashimoto's patients. Therefore, the differences in the rates of reactivity to TPO(AA 513–633) (SEQ ID NO:1) cannot be explained solely as the consequence of an inflammatory process that yields autoantibodies to denatured TPO.

In arguing a pathogenic role for TPO autoantibodies, several studies have shown that anti-microsomal antibodies from patients with Hashimoto's disease have been shown to inhibit the activity of TPO. Okamoto, Y. et al., *J. Clin. Endocrinol Metab.* 68:730–34 (1989). The TPO(AA 513–633) (SEQ ID NO:1) fragment overlaps with a region, amino acids 510 to 567, previously reported to show homology to the heme binding site of the Cytochrome C oxidase enzyme (Libert, F. et al., *EMBO J.* 6:4193–4196 (1987)) and therefore may constitute a functional part of the enzyme. The different reactivity to TPO(AA 513–633) (SEQ ID NO:1) suggests a possible pathophysiologic role for TPO antibodies in Hashimoto's disease and could also explain the variability in the studies examining the effect of autoantibodies on TPO function. However, there appeared to be no significant correlation between reactivity to any form or region of TPO and any clinical characteristic of the Hashimoto's patients. While this could be due to variations in the clinical presentation of Hashimoto's disease and the fact that serum samples were obtained from the patients at variable times during the course of the disease, it might indicate that TPO autoantibodies do not play a prominent role in the producing clinical signs of AITD (e.g., hypothyroidism or goiter size). To resolve this question, reactivity to this region might be evaluated in a prospective manner in relatives of Hashimoto's patients to see if these autoantibodies presage the development of thyroiditis. In the Graves' patients, a significant correlation was noted between the goiter, anti-thyroglobulin antibody titers and reactivity to both TPO(AA 633–933) (SEQ ID NO:1) and the reduced form of TPO. This may indicate that antibodies to this area of TPO are a marker for glandular inflammation in Graves' disease.

Since Western blot assays are not as sensitive as other immunoassays, and may underestimate the number of reactive patients, there may be more than one epitope in the TPO(AA 513–633) (SEQ ID NO:1) region, only one of which is specific for Hashimoto's disease. In addition, while some of the Graves' patients did react to this area, it is possible that these patients may have concomitant Hashimoto's disease. The coexistence of these diseases is well-documented (Hirota, Y. et al., *J. Clin. Endocrinol. Metab.*62:165–69 (1986)), and the identification of this patient subgroup may be of value because these individuals might develop long-term remissions of their hyperthyroidism due to the presence of the thyroiditis. However, since all of the Graves' patients in this study were treated with thyroid ablation, this hypothesis was not tested.

SPECIFIC EXAMPLE V

EPITOPE MAPPING OF THE TPO 592–613 AUTOANTIBODY BINDING SITE

In order to further localize and understand the specificity of autoantibodies binding to thyroid peroxidase, efforts were undertaken to determine the exact epitopes of TPO autoantibodies directed to the fragment of TPO contained within amino acids. Initially, the AA 517–633 (SEQ ID NO:1) fragment was digested with an additional restriction enzyme to yield a AA 573–633 (SEQ ID NO:1) fragment. This portion of TPO retained the binding activity present in the whole AA 517–633 (SEQ ID NO:1) fragment. However, it became apparent that there were no appropriate restriction enzyme sites to further cut the cDNA. Thus, for fine mapping of this autoantibody binding site, the polymerase chain reaction (PCR) was used.

Figure 18:
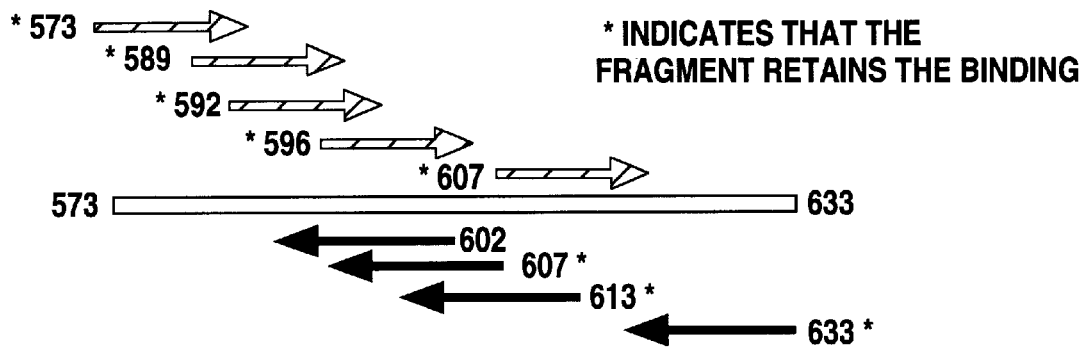
FIG. 18 (SEQ ID NO:3 through SEQ ID NO:9) is a schematic of fine mapping of a TPO epitope using PCR.

FIG. 18 is a schematic of the fine mapping of the TPO epitope using PCR. Primers were constructed to amplify cDNA segments of approximately 60 nucleotides (20 amino acids) in length. The initial (smallest fragment) was between amino acids 592–613 (SEQ ID NO:1) (20 amino acids from the ends of the 573–633 (SEQ ID NO:1) fragment). The primers were also prepared with the appropriate restriction enzyme sites at either end for insertion into the pMalc expression plasmid. The fragment of the cDNA corresponding to the intervening segment between these primers was amplified, ethanol precipitated and digested with the appropriate restriction enzyme. The cDNA products were then subjected to PAGE, isolated from the gel and used to ligate appropriately digested pMalc vector. This vector was then used to transform bacteria, and protein production was induced with IPTG. A fusion protein corresponding to the area of TPO encompassed by the primers was then isolated through amylose affinity chromatography. The work was conducted in a manner similar to that described in Specific Example I and Maastricht, J. et al. *J. Clin. Endocrinol. Metab.* 75:121–126 (1992).

Western blots of the 596–611 (SEQ ID NO:1) fusion protein (performed by the protocol set forth above in Specific Example IV), showed that this fusion protein did not contain the epitope, and new primers were used which added four amino acids at either end to produce the region 590–615 (SEQ ID NO:1). Western blots with the resulting fusion protein showed that the AA 590–615 (SEQ ID NO:1) region was recognized by autoantibodies, and could inhibit binding to the whole AA 517–633 (SEQ ID NO:1) fragment. In cross-amplification experiments, it was shown that the 592–615 (SEQ ID NO:1) fragment maintained the epitope whereas the 590–611 (SEQ ID NO:1) fragment did not, thereby documenting that the carboxyl limit of the binding site was located between amino acids 611 and 615 (SEQ ID NO:1). Subsequent amplification showed that if the peptide C-terminus was at an amino acid less than 613, the binding was lost. Together, this localized the epitope binding site between amino acids 592 and 613.

Discussion

The localized binding site between AA 592 and 613 (SEQ ID NO:1) is unique in that it shows strong immunology between the other peroxidase enzymes (meyloperoxidase and lactoperoxidase) with divergent sequences primarily between amino acids 602 and 615 (SEQ ID NO:1). In addition, it is almost entirely homologous between human, porcine and rat TPO with only two non-conserved substitutions within the whole coding region. Thus, it appears that this segment is unique for thyroid peroxidase and does not share sufficient immunology with any of the other peroxidase enzymes to account for cross reactivity. Binding studies with meyloperoxidase and lactoperoxidase also fail to show binding activity in antibodies affinity purified using AA 590–615 (SEQ ID NO:1) peptides. Previously, antibodies against thyroid peroxidase have been shown to cross-react with these two other enzymes, thereby confusing diagnosis. The present invention, however, specifies a region containing an autoantibody epitope that is unique and specific for thyroid peroxidase. Having now defined this epitope to 22 amino acids, it can be manufactured synthetically and provide specificity in the diagnosis of autoantibodies to thyroid peroxidase and Hashimoto's disease and for use in immunotherapy.

Those skilled in the art can appreciate from the foregoing description that the broad teachings of the present invention can be implemented in a variety of forms. Therefore, while this invention has been described in connection with particular examples thereof, the true scope of the invention should not be so limited since other modifications will become apparent upon a study of the drawings, specification and following claims. All applications and publications cited herein are incorporated by reference. It will be appreciated that the publications cited herein merely reflect the current state of the art and the skills and methodology attendant to those skilled in the art.

We claim:

1. A method of screening for presence of autoantibody to thyroid peroxidase in a sample from a patient comprising the steps of:

(a) providing the sample to be screened from a patient;

(b) providing a thyroid peroxidase reagent comprising a substantially pure thyroid peroxidase epitopic peptide which consists of amino acid residue sequence SEQ ID NO:3 (residues 592 to 613 of SEQ ID NO:1);

(c) contacting the sample with the thyroid peroxidase reagent under conditions favorable for specific binding of the autoantibody present in the sample to the epitopic peptide; and (d) detecting specific binding of the autoantibody in the sample to the epitopic peptide as indicative of the presence of the autoantibody to thyroid peroxidase in the sample from the patient.

2. The method of claim 1, wherein the sample comprises biological fluid or tissue potentially containing the autoantibody.

3. The method of claim 2, wherein the sample comprises serum.

4. A method of screening for autoimmune thyroiditis in a patient comprising the steps of:

(a) providing a biological tissue or fluid sample, potentially containing autoantibody to thyroid peroxidase, from the patient;

(b) providing a thyroid peroxidase epitopic reagent comprising a substantially pure thyroid peroxidase epitopic peptide which consists of amino acid residue sequence SEQ ID NO:3 (residues 592 to 613 of SEQ ID NO:1);

(c) contacting the sample with the thyroid peroxidase epitopic reagent under conditions favorable for specific binding of the autoantibody present in the sample to the epitopic peptide; and (d) detecting specific binding of the autoantibody in the sample to the epitopic peptide as indicative of autoimmune thyroiditis in the patient.

5. A substantially pure thyroid peroxidase epitopic peptide consisting of amino acid residue sequence SEQ ID NO:3 (residues 592 to 613 of SEQ ID NO:1).

6. A kit for assaying for autoimmune thyroiditis comprising:

(a) a substantially pure thyroid peroxidase epitopic peptide consisting of amino acid residue sequence SEQ ID NO:3 (residues 592 to 613 of SEQ ID NO:1) which binds specifically with thyroid peroxidase autoantibody, in an amount sufficient for performing at least one assay; and (b) a reagent for detecting binding of the autoantibody to the epitopic peptide, in an amount sufficient for performing at least one assay.

* * * * *

UNITED STATES PATENT AND TRADEMARK OFFICE
CERTIFICATE OF CORRECTION

PATENT NO. : 5,998,153  Page 1 of 2
DATED : December 7, 1999
INVENTOR(S) : Baker, Jr. et al.

It is certified that error appears in the above-identified patent and that said Letters Patent is hereby corrected as shown below:

Title page,
Item [56], "Hasimoto" should be -- Hashimoto --
Item [56], "directd" should be -- directed --

Column 1,
Line 9, insert:

-- STATEMENT OF RIGHTS TO INVENTIONS MADE UNDER FEDERALLY SPONSORED RESEARCH
This invention was made in part with support from the United States government under Grant No. AI30501 from the National Institutes of Health. Accordingly, the United States government has certain rights in this invention. --;

Column 2,
Line 4, "73:857-560" should be -- 73:557-560 --

Column 16,
Line 50, "Christor" should be -- Christov --

Column 17,
Line 53, "BgIll" should be -- BglII --

Column 18,
Lines 35 and 40, "NaCI" should -- NaCl --

Column 19,
Line 66, after "(1-455)" should be added -- (SEQ ID NO:1) --

Column 20,
Line 8, "preformed" should be -- performed --
Line 18, after "(Δ4-455)" should be added -- (SEQ ID NO:1) --;
Line 57, "pMaIcRI" should be -- pMALcRI --

UNITED STATES PATENT AND TRADEMARK OFFICE
CERTIFICATE OF CORRECTION

PATENT NO. : 5,998,153
DATED : December 7, 1999
INVENTOR(S) : Baker, Jr. et al.

Figure 9A:
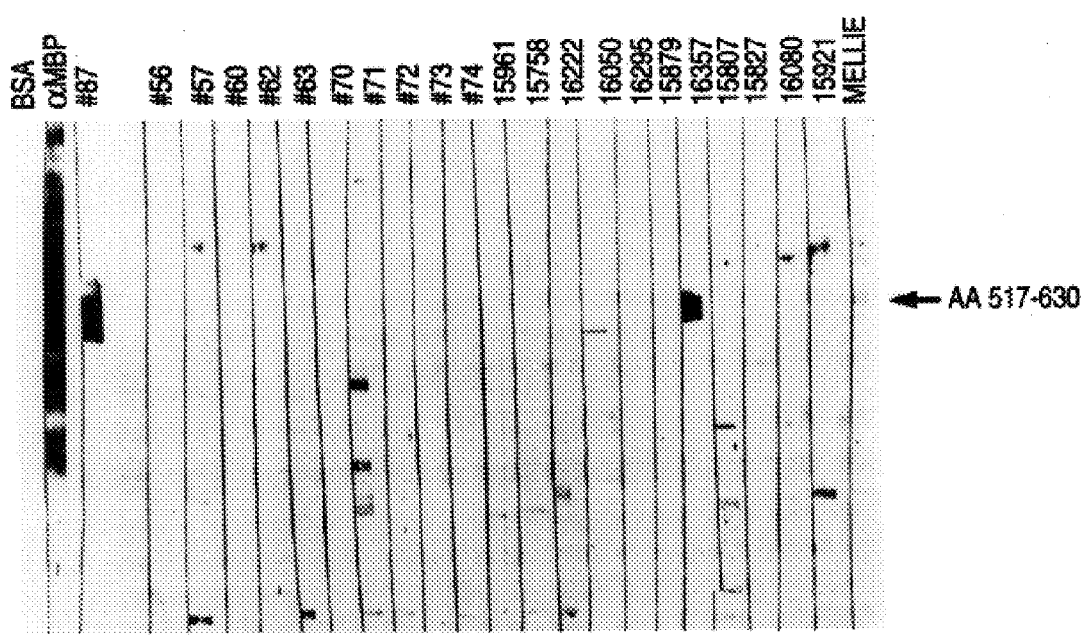
FIGS. 9A and 9B are Western blot analyses of sera from patients with thyroiditis.
Figure 9B:
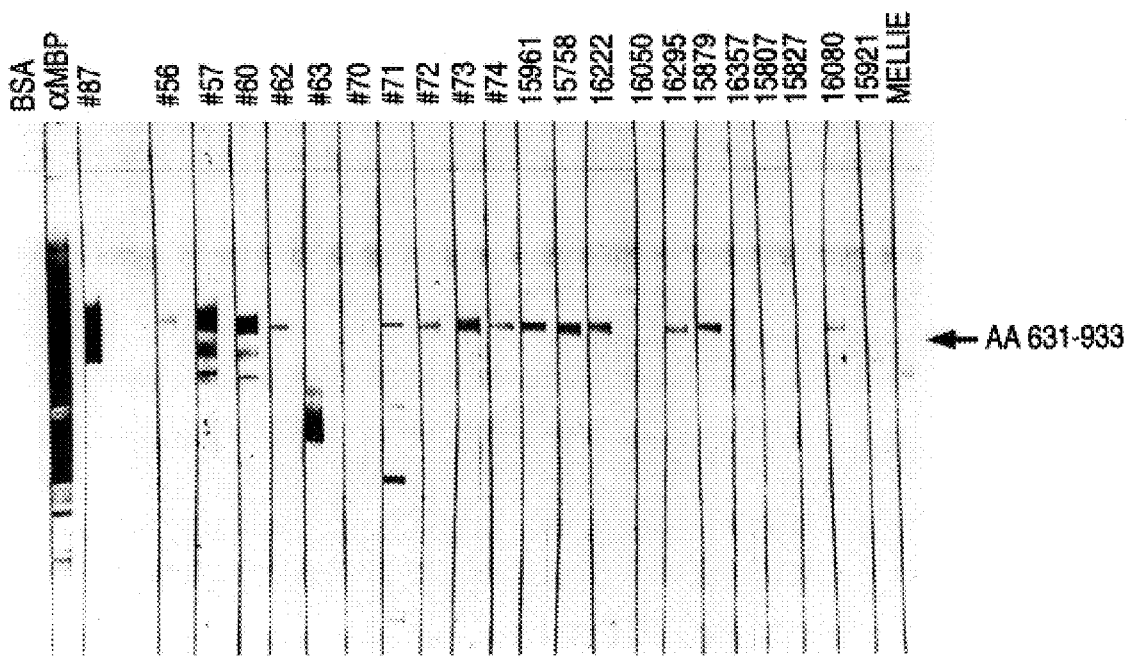

It is certified that error appears in the above-identified patent and that said Letters Patent is hereby corrected as shown below:

Column 22,
Line 34, after "seen." should be added -- In Figures 9A and 9B, the lanes form left to right are as follows: BSA - no antibody lane; anti-MBP – anti maltose binding protein; #87 – positive control serum; #56 through #74 are samples from different patients diagnosed with Hashimoto's thyroiditis; 15961 through 16295 are smpoles from Hashimoto patients with hypothyroidism; 15879 is a patient with Euthyroid (normal thyroid) goiter with Hashimoto thyriodits; 16357 is a patient with post partum subacute thyroiditis (PPSAT); 15807 is a patient with painless subactue thyroiditis; 15827 is a patient with granulomatous subacute thyroiditis; 16080 is a patient with no disease but positive for thyroglobulin antibody; 15921 is a patient with no disease and antibody-negative; and MELLIE is a normal control. --

Column 24,
Line 45, "twosteps" should be -- two steps --

Column 27,
Line 2, "(1984)" should be -- (1983) --

Signed and Sealed this

Thirtieth Day of July, 2002

Attest:

Attesting Officer

JAMES E. ROGAN
Director of the United States Patent and Trademark Office

```
                        SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
          (A) LENGTH: 933 amino acids
          (B) TYPE: amino acid
          (C) STRANDEDNESS: single
          (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
          (A) ORGANISM: Homo sapiens
          (D) DEVELOPMENTAL STAGE: Mature
          (F) TISSUE TYPE: Thyroid gland(from people with Grave's
              disease)

(vii) IMMEDIATE SOURCE:
          (B) CLONE: phTPO-2.8

(ix) FEATURE:
          (A) NAME/KEY: Peptide
          (B) LOCATION: join(1..3, 456..631)
          (D) OTHER INFORMATION: /note= "TPO region within fusion
              plasmid: TPO(delta4-455)"

(ix) FEATURE:
          (A) NAME/KEY: Peptide
          (B) LOCATION: 1..120
          (D) OTHER INFORMATION: /note= "C-terminal truncation:
              TPO(1-120)"

(ix) FEATURE:
          (A) NAME/KEY: Region
          (B) LOCATION: 1..400
          (D) OTHER INFORMATION: /note= "TPO epitopic region within
              fusion protein: MBP-TPO (AA 1-400)"

(ix) FEATURE:
          (A) NAME/KEY: Peptide
          (B) LOCATION: 1..455
          (D) OTHER INFORMATION: /note= "C-terminal truncation-
              TPO(1-455) or N-terminal half of TPO"

(ix) FEATURE:
          (A) NAME/KEY: Peptide
          (B) LOCATION: 1..631
          (D) OTHER INFORMATION: /note= "C-terminal truncation:
              TPO(1-631)"

(ix) FEATURE:
          (A) NAME/KEY: Region
          (B) LOCATION: 266..281
          (D) OTHER INFORMATION: /note= "TPO epitopic or binding
              region"

(ix) FEATURE:
          (A) NAME/KEY: Region
          (B) LOCATION: 376..631
          (D) OTHER INFORMATION: /note= "TPO epitopic region within
              fusion protein: MBP-TPO (AA 376-631)"
```

```
(ix) FEATURE:
      (A) NAME/KEY: Region
      (B) LOCATION: join(455..532, 590..933)
      (D) OTHER INFORMATION: /note= "alternatively spliced
          C-terminus of TPO"

(ix) FEATURE:
      (A) NAME/KEY: Region
      (B) LOCATION: 455..933
      (D) OTHER INFORMATION: /note= "TPO C-terminus containing
          binding region"

(ix) FEATURE:
      (A) NAME/KEY: Region
      (B) LOCATION: 456..631
      (D) OTHER INFORMATION: /note= "TPO binding or epitopic
          region"

(ix) FEATURE:
      (A) NAME/KEY: Region
      (B) LOCATION: 456..633
      (D) OTHER INFORMATION: /note= "TPO binding or epitopic
          region"

(ix) FEATURE:
      (A) NAME/KEY: Region
      (B) LOCATION: 456..933
      (D) OTHER INFORMATION: /note= "TPO binding or epitopic
          region"

(ix) FEATURE:
      (A) NAME/KEY: Region
      (B) LOCATION: 456..933
      (D) OTHER INFORMATION: /note= "TPO region within maltose
          binding fusion protein"

(ix) FEATURE:
      (A) NAME/KEY: Region
      (B) LOCATION: 457..517
      (D) OTHER INFORMATION: /note= "non-reactive fragment"

(ix) FEATURE:
      (A) NAME/KEY: Region
      (B) LOCATION: 457..633
      (D) OTHER INFORMATION: /note= "TPO region within fusion
          plasmid pMalTPO"

(ix) FEATURE:
      (A) NAME/KEY: Region
      (B) LOCATION: 457..933
      (D) OTHER INFORMATION: /note= "TPO binding region within
          plasmid pMalTPO"

(ix) FEATURE:
      (A) NAME/KEY: Region
      (B) LOCATION: 465..933
      (D) OTHER INFORMATION: /note= "TPO binding region of
          maltose binding region fusion construct"

(ix) FEATURE:
      (A) NAME/KEY: Region
      (B) LOCATION: 513..633
      (D) OTHER INFORMATION: /note= "recombinant TPO"

(ix) FEATURE:
      (A) NAME/KEY: Region
      (B) LOCATION: 517..630
      (D) OTHER INFORMATION: /note= "TPO binding or epitopic
          region"

(ix) FEATURE:
      (A) NAME/KEY: Region
      (B) LOCATION: 517..633
      (D) OTHER INFORMATION: /note= "TPO binding or epitopic
          region"

(ix) FEATURE:
      (A) NAME/KEY: Region
      (B) LOCATION: 573..633
      (D) OTHER INFORMATION: /note= "TPO binding or epitopic
```

-continued

```
            region"

(ix) FEATURE:
     (A) NAME/KEY: Region
     (B) LOCATION: 590..611
     (D) OTHER INFORMATION: /note= "TPO region within maltose
         binding fusion protein"

(ix) FEATURE:
     (A) NAME/KEY: Region
     (B) LOCATION: 590..615
     (D) OTHER INFORMATION: /note= "TPO binding or epitopic
         region"

(ix) FEATURE:
     (A) NAME/KEY: Binding-site
     (B) LOCATION: 590..675
     (D) OTHER INFORMATION: /note= "TPO binding or epitopic
         region"

(ix) FEATURE:
     (A) NAME/KEY: Region
     (B) LOCATION: 592..613
     (D) OTHER INFORMATION: /note= "TPO binding or epitopic
         region"

(ix) FEATURE:
     (A) NAME/KEY: Region
     (B) LOCATION: 596..611
     (D) OTHER INFORMATION: /note= "Tpo region within fusion
         protein"

(ix) FEATURE:
     (A) NAME/KEY: Region
     (B) LOCATION: 602..615
     (D) OTHER INFORMATION: /note= "TPO region containing
         divergent sequences"

(ix) FEATURE:
     (A) NAME/KEY: Region
     (B) LOCATION: 611..615
     (D) OTHER INFORMATION: /note= "TPO binding or epitopic
         region"

(ix) FEATURE:
     (A) NAME/KEY: Region
     (B) LOCATION: 631..933
     (D) OTHER INFORMATION: /note= "TPO binding or epitopic
         region"

(ix) FEATURE:
     (A) NAME/KEY: Region
     (B) LOCATION: 632..933
     (D) OTHER INFORMATION: /note= "TPO region within maltose
         binding fusion protein"

(ix) FEATURE:
     (A) NAME/KEY: Region
     (B) LOCATION: 633..768
     (D) OTHER INFORMATION: /note= "TPO binding or epitopic
         region"

(ix) FEATURE:
     (A) NAME/KEY: Region
     (B) LOCATION: 633..933
     (D) OTHER INFORMATION: /note= "TPO binding or epitopic
         region"

(ix) FEATURE:
     (A) NAME/KEY: Region
     (B) LOCATION: 700..933
     (D) OTHER INFORMATION: /note= "TPO binding or epitopic
         region"

(ix) FEATURE:
     (A) NAME/KEY: Region
     (B) LOCATION: 768..933
     (D) OTHER INFORMATION: /note= "TPO binding or epitopic
         region"
```

```
    (x) PUBLICATION INFORMATION:
        (A) AUTHORS: Kimura, S.
            Kotani, T.
            McBride, O.W.
            Umeki, K.
            Nakayama, T.
            Ohtaki, S.
            Hirai, K.
        (B) TITLE: Human thyroid peroxidase: Complete cDNA and
            protein sequence, chromosome mapping, and
            identification of two alternately spliced mRNAs
        (C) JOURNAL: Proc. Natl. Acad. Sci. U.S.A.
        (D) VOLUME: 84
        (F) PAGES: 5555-5559
        (G) DATE: 1987
        (K) RELEVANT RESIDUES IN SEQ ID NO:1: FROM 1 TO 933

(xi) SEQUENCE DESCRIPTION: SEQ ID NO:1:

Met Arg Ala Leu Ala Val Leu Ser Val Thr Leu Val Met Ala Cys Thr
1               5                   10                  15

Glu Ala Phe Phe Pro Phe Ile Ser Arg Gly Lys Glu Leu Leu Trp Gly
            20                  25                  30

Lys Pro Glu Glu Ser Arg Val Ser Ser Val Leu Glu Glu Ser Lys Arg
        35                  40                  45

Leu Val Asp Thr Ala Met Tyr Ala Thr Met Gln Arg Asn Leu Lys Lys
50                  55                  60

Arg Gly Ile Leu Ser Pro Ala Gln Leu Leu Ser Phe Ser Lys Leu Pro
65                  70                  75                  80

Glu Pro Thr Ser Gly Val Ile Ala Arg Ala Ala Glu Ile Met Glu Thr
                85                  90                  95

Ser Ile Gln Ala Met Lys Arg Lys Val Asn Leu Lys Thr Gln Gln Ser
            100                 105                 110

Gln His Pro Thr Asp Ala Leu Ser Glu Asp Leu Leu Ser Ile Ile Ala
        115                 120                 125

Asn Met Ser Gly Cys Leu Pro Tyr Met Leu Pro Pro Lys Cys Pro Asn
130                 135                 140

Thr Cys Leu Ala Asn Lys Tyr Arg Pro Ile Thr Gly Ala Cys Asn Asn
145                 150                 155                 160

Arg Asp His Pro Arg Trp Gly Ala Ser Asn Thr Ala Leu Ala Arg Trp
                165                 170                 175

Leu Pro Pro Val Tyr Glu Asp Gly Phe Ser Gln Pro Arg Gly Trp Asn
            180                 185                 190

Pro Gly Phe Leu Tyr Asn Gly Phe Pro Leu Pro Pro Val Arg Glu Val
        195                 200                 205

Thr Arg His Val Ile Gln Val Ser Asn Glu Val Val Thr Asp Asp Asp
210                 215                 220

Arg Tyr Ser Asp Leu Leu Met Ala Trp Gly Gln Tyr Ile Asp His Asp
225                 230                 235                 240

Ile Ala Phe Thr Pro Gln Ser Thr Ser Lys Ala Ala Phe Gly Gly Gly
                245                 250                 255

Ala Asp Cys Gln Met Thr Cys Glu Asn Gln Asn Pro Cys Phe Pro Ile
            260                 265                 270

Gln Leu Pro Glu Glu Ala Arg Pro Ala Ala Gly Thr Ala Cys Leu Pro
        275                 280                 285

Phe Tyr Arg Ser Ser Ala Ala Cys Gly Thr Gly Asp Gln Gly Ala Leu
290                 295                 300

Phe Gly Asn Leu Ser Thr Ala Asn Pro Arg Gln Gln Met Asn Gly Leu
305                 310                 315                 320

Thr Ser Phe Leu Asp Ala Ser Thr Val Tyr Gly Ser Ser Pro Ala Leu
```

-continued

```
            325                 330                 335
Glu Arg Gln Leu Arg Asn Trp Thr Ser Ala Glu Gly Leu Leu Arg Val
            340                 345                 350
His Ala Arg Leu Arg Asp Ser Gly Arg Ala Tyr Leu Pro Phe Val Pro
            355                 360                 365
Pro Arg Arg Pro Ala Ala Cys Ala Pro Glu Pro Gly Ile Pro Gly Glu
            370                 375                 380
Thr Arg Gly Pro Cys Phe Leu Ala Gly Asp Gly Arg Ala Ser Glu Val
385                     390                 395                 400
Pro Ser Leu Thr Ala Leu His Thr Leu Trp Leu Arg Glu His Asn Arg
            405                 410                 415
Leu Ala Ala Ala Leu Lys Ala Leu Asn Ala His Trp Ser Ala Asp Ala
            420                 425                 430
Val Tyr Gln Glu Ala Arg Lys Val Val Gly Ala Leu His Gln Ile Ile
            435                 440                 445
Thr Leu Arg Asp Tyr Ile Pro Arg Ile Leu Gly Pro Glu Ala Phe Gln
            450                 455                 460
Gln Tyr Val Gly Pro Tyr Glu Gly Tyr Asp Ser Thr Ala Asn Pro Thr
465                     470                 475                 480
Val Ser Asn Val Phe Ser Thr Ala Ala Phe Arg Phe Gly His Ala Thr
                        485                 490                 495
Ile His Pro Leu Val Arg Arg Leu Asp Ala Ser Phe Gln Glu His Pro
            500                 505                 510
Asp Leu Pro Gly Leu Trp Leu His Gln Ala Phe Phe Ser Pro Trp Thr
            515                 520                 525
Leu Leu Arg Gly Gly Gly Leu Asp Pro Leu Ile Arg Gly Leu Leu Ala
            530                 535                 540
Arg Pro Ala Lys Leu Gln Val Gln Asp Gln Leu Met Asn Glu Glu Leu
545                     550                 555                 560
Thr Glu Arg Leu Phe Val Leu Ser Asn Ser Ser Thr Leu Asp Leu Ala
                        565                 570                 575
Ser Ile Asn Leu Gln Arg Gly Arg Asp His Gly Leu Pro Gly Tyr Asn
            580                 585                 590
Glu Trp Arg Glu Phe Cys Gly Leu Pro Arg Leu Glu Thr Pro Ala Asp
            595                 600                 605
Leu Ser Thr Ala Ile Ala Ser Arg Ser Val Ala Asp Lys Ile Leu Asp
            610                 615                 620
Leu Tyr Lys His Pro Asp Asn Ile Asp Val Trp Leu Gly Gly Leu Ala
625                     630                 635                 640
Glu Asn Phe Leu Pro Arg Ala Arg Thr Gly Pro Leu Phe Ala Cys Leu
                        645                 650                 655
Ile Gly Lys Gln Met Lys Ala Leu Arg Asp Gly Asp Trp Phe Trp Trp
            660                 665                 670
Glu Asn Ser His Val Phe Thr Asp Ala Gln Arg Arg Glu Leu Glu Lys
            675                 680                 685
His Ser Leu Ser Arg Val Ile Cys Asp Asn Thr Gly Leu Thr Arg Val
            690                 695                 700
Pro Met Asp Ala Phe Gln Val Gly Lys Phe Pro Glu Asp Phe Glu Ser
705                     710                 715                 720
Cys Asp Ser Ile Pro Gly Met Asn Leu Glu Ala Trp Arg Glu Thr Phe
                        725                 730                 735
Pro Gln Asp Asp Lys Cys Gly Phe Pro Glu Ser Val Glu Asn Gly Asp
            740                 745                 750
```

-continued

```
Phe Val His Cys Glu Glu Ser Gly Arg Arg Val Leu Val Tyr Ser Cys
    755                 760                 765
Arg His Gly Tyr Glu Leu Gln Gly Arg Glu Gln Leu Thr Cys Thr Gln
    770                 775                 780
Glu Gly Trp Asp Phe Gln Pro Pro Leu Cys Lys Asp Val Asn Glu Cys
785                 790                 795                 800
Ala Asp Gly Ala His Pro Pro Cys His Ala Ser Ala Arg Cys Arg Asn
            805                 810                 815
Thr Lys Gly Gly Phe Gln Cys Leu Cys Ala Asp Pro Tyr Glu Leu Gly
            820                 825                 830
Asp Asp Gly Arg Thr Cys Val Asp Ser Gly Arg Leu Pro Arg Ala Thr
            835                 840                 845
Trp Ile Ser Met Ser Leu Ala Ala Leu Leu Ile Gly Gly Phe Ala Gly
    850                 855                 860
Leu Thr Ser Thr Val Ile Cys Arg Trp Thr Arg Thr Gly Thr Lys Ser
865                 870                 875                 880
Thr Leu Pro Ile Ser Glu Thr Gly Gly Thr Pro Glu Leu Arg Cys
            885                 890                 895
Gly Lys His Gln Ala Val Gly Thr Ser Pro Gln Arg Ala Ala Ala Gln
            900                 905                 910
Asp Ser Glu Gln Glu Ser Ala Gly Met Glu Gly Arg Asp Thr His Arg
    915                 920                 925
Leu Pro Arg Ala Leu
    930
```

(2) INFORMATION FOR SEQ ID NO:2:

(i) SEQUENCE CHARACTERISTICS:
        (A) LENGTH: 3048 base pairs
        (B) TYPE: nucleic acid
        (C) STRANDEDNESS: double
        (D) TOPOLOGY: linear (ii) MOLECULE TYPE: mRNA (iii) HYPOTHETICAL: NO (iv) ANTI-SENSE: NO (vi) ORIGINAL SOURCE:
        (A) ORGANISM: Homo sapiens
        (D) DEVELOPMENTAL STAGE: Mature
        (F) TISSUE TYPE: Thyroid gland(from patients with Grave's
            disease)

(vii) IMMEDIATE SOURCE:
        (B) CLONE: phTPO-2.8

(viii) POSITION IN GENOME:
        (B) MAP POSITION: 2pter-q11

(ix) FEATURE:
        (A) NAME/KEY: CDS
        (B) LOCATION: 73..2871

(x) PUBLICATION INFORMATION:
        (A) AUTHORS: Kimura, S.
            Kotani, T.
            McBride, O.W.
            Umeki, K.
            Nakayama, T.
            Ohtaki, S.
            Hirai, K.
        (B) TITLE: Human thyroid peroxidase: Complete cDNA and
            protein sequence, chromosome mapping, and
            identification of two alternately spliced mRNAs
        (C) JOURNAL: Proc. Natl. Acad. Sci. U.S.A.
        (D) VOLUME: 84

(F) PAGES: 5555-5559
(G) DATE: 1987
(K) RELEVANT RESIDUES IN SEQ ID NO:2: FROM 1 TO 3048

(xi) SEQUENCE DESCRIPTION: SEQ ID NO:2:

```
CATTTCAGAA GAGTTACAGC CGTGAAAATT ACTCAGCAGT GCAGTTGGCT GAGAAGAGGA          60

AAAAAGGTCA GA ATG AGA GCG CTC GCT GTG CTG TCT GTC ACG CTG GTT            108
              Met Arg Ala Leu Ala Val Leu Ser Val Thr Leu Val
              1               5                   10

ATG GCC TGC ACA GAA GCC TTC TTC CCC TTC ATC TCG AGA GGG AAA GAA          156
Met Ala Cys Thr Glu Ala Phe Phe Pro Phe Ile Ser Arg Gly Lys Glu
            15                  20                  25

CTC CTT TGG GGA AAG CCT GAG GAG TCT CGT GTC TCT AGC GTC TTG GAG          204
Leu Leu Trp Gly Lys Pro Glu Glu Ser Arg Val Ser Ser Val Leu Glu
    30                  35                  40

GAA AGC AAG CGC CTG GTG GAC ACC GCC ATG TAC GCC ACG ATG CAG AGA          252
Glu Ser Lys Arg Leu Val Asp Thr Ala Met Tyr Ala Thr Met Gln Arg
45                  50                  55                  60

AAC CTC AAG AAA AGA GGA ATC CTT TCT CCA GCT CAG CTT CTG TCT TTT          300
Asn Leu Lys Lys Arg Gly Ile Leu Ser Pro Ala Gln Leu Leu Ser Phe
                65                  70                  75

TCC AAA CTT CCT GAG CCA ACA AGC GGA GTG ATT GCC CGA GCA GCA GAG          348
Ser Lys Leu Pro Glu Pro Thr Ser Gly Val Ile Ala Arg Ala Ala Glu
            80                  85                  90

ATA ATG GAA ACA TCA ATA CAA GCG ATG AAA AGA AAA GTC AAC CTG AAA          396
Ile Met Glu Thr Ser Ile Gln Ala Met Lys Arg Lys Val Asn Leu Lys
        95                  100                 105

ACT CAA CAA TCA CAG CAT CCA ACG GAT GCT TTA TCA GAA GAT CTG CTG          444
Thr Gln Gln Ser Gln His Pro Thr Asp Ala Leu Ser Glu Asp Leu Leu
    110                 115                 120

AGC ATC ATT GCA AAC ATG TCT GGA TGT CTC CCT TAC ATG CTG CCC CCA          492
Ser Ile Ile Ala Asn Met Ser Gly Cys Leu Pro Tyr Met Leu Pro Pro
125                 130                 135                 140

AAA TGC CCA AAC ACT TGC CTG GCG AAC AAA TAC AGG CCC ATC ACA GGA          540
Lys Cys Pro Asn Thr Cys Leu Ala Asn Lys Tyr Arg Pro Ile Thr Gly
                145                 150                 155

GCT TGC AAC AAC AGA GAC CAC CCC AGA TGG GGC GCC TCC AAC ACG GCC          588
Ala Cys Asn Asn Arg Asp His Pro Arg Trp Gly Ala Ser Asn Thr Ala
            160                 165                 170

CTG GCA CGA TGG CTC CCT CCA GTC TAT GAG GAC GGC TTC AGT CAG CCC          636
Leu Ala Arg Trp Leu Pro Pro Val Tyr Glu Asp Gly Phe Ser Gln Pro
        175                 180                 185

CGA GGC TGG AAC CCC GGC TTC TTG TAC AAC GGG TTC CCA CTG CCC CCG          684
Arg Gly Trp Asn Pro Gly Phe Leu Tyr Asn Gly Phe Pro Leu Pro Pro
    190                 195                 200

GTC CGG GAG GTG ACA AGA CAT GTC ATT CAA GTT TCA AAT GAG GTT GTC          732
Val Arg Glu Val Thr Arg His Val Ile Gln Val Ser Asn Glu Val Val
205                 210                 215                 220

ACA GAT GAT GAC CGC TAT TCT GAC CTC CTG ATG GCA TGG GGA CAA TAC          780
Thr Asp Asp Asp Arg Tyr Ser Asp Leu Leu Met Ala Trp Gly Gln Tyr
                225                 230                 235

ATC GAC CAC GAC ATC GCG TTC ACA CCA CAG AGC ACC AGC AAA GCT GCC          828
Ile Asp His Asp Ile Ala Phe Thr Pro Gln Ser Thr Ser Lys Ala Ala
            240                 245                 250

TTC GGG GGA GGG GCT GAC TGC CAG ATG ACT TGT GAG AAC CAA AAC CCA          876
Phe Gly Gly Gly Ala Asp Cys Gln Met Thr Cys Glu Asn Gln Asn Pro
        255                 260                 265

TGT TTT CCC ATA CAA CTC CCG GAG GAG GCC CGG CCG GCC GCG GGC ACC          924
Cys Phe Pro Ile Gln Leu Pro Glu Glu Ala Arg Pro Ala Ala Gly Thr
    270                 275                 280
```

-continued

| | | |
|---|---|---|
| GCC TGT CTG CCC TTC TAC CGC TCT TCG GCC GCC TGC GGC ACC GGG GAC<br>Ala Cys Leu Pro Phe Tyr Arg Ser Ser Ala Ala Cys Gly Thr Gly Asp<br>285                    290                    295                    300 | 972 |

| | |
|---|---|
| CAA GGC GCG CTC TTT GGG AAC CTG TCC ACG GCC AAC CCG CGG CAG CAG<br>Gln Gly Ala Leu Phe Gly Asn Leu Ser Thr Ala Asn Pro Arg Gln Gln<br>                    305                    310                    315 | 1020 |
| ATG AAC GGG TTG ACC TCG TTC CTG GAC GCG TCC ACC GTG TAT GGC AGC<br>Met Asn Gly Leu Thr Ser Phe Leu Asp Ala Ser Thr Val Tyr Gly Ser<br>                    320                    325                    330 | 1068 |
| TCC CCG GCC CTA GAG AGG CAG CTG CGG AAC TGG ACC AGT GCC GAA GGG<br>Ser Pro Ala Leu Glu Arg Gln Leu Arg Asn Trp Thr Ser Ala Glu Gly<br>335                    340                    345 | 1116 |
| CTG CTC CGC GTC CAC GCG CGC CTC CGG GAC TCC GGC CGC GCC TAC CTG<br>Leu Leu Arg Val His Ala Arg Leu Arg Asp Ser Gly Arg Ala Tyr Leu<br>     350                    355                    360 | 1164 |
| CCC TTC GTG CCG CCA CGG CGG CCT GCG GCC TGT GCG CCC GAG CCC GGC<br>Pro Phe Val Pro Pro Arg Arg Pro Ala Ala Cys Ala Pro Glu Pro Gly<br>365                    370                    375                    380 | 1212 |
| ATC CCC GGA GAG ACC CGC GGG CCC TGC TTC CTG GCC GGA GAC GGC CGC<br>Ile Pro Gly Glu Thr Arg Gly Pro Cys Phe Leu Ala Gly Asp Gly Arg<br>                    385                    390                    395 | 1260 |
| GCC AGC GAG GTC CCC TCC CTG ACG GCA CTG CAC ACG CTG TGG CTG CGC<br>Ala Ser Glu Val Pro Ser Leu Thr Ala Leu His Thr Leu Trp Leu Arg<br>                    400                    405                    410 | 1308 |
| GAG CAC AAC CGC CTG GCC GCG GCG CTC AAG GCC CTC AAT GCG CAC TGG<br>Glu His Asn Arg Leu Ala Ala Ala Leu Lys Ala Leu Asn Ala His Trp<br>              415                    420                    425 | 1356 |
| AGC GCG GAC GCC GTG TAC CAG GAG GCG CGC AAG GTC GTG GGC GCT CTG<br>Ser Ala Asp Ala Val Tyr Gln Glu Ala Arg Lys Val Val Gly Ala Leu<br>430                    435                    440 | 1404 |
| CAC CAG ATC ATC ACC CTG AGG GAT TAC ATC CCC AGG ATC CTG GGA CCC<br>His Gln Ile Ile Thr Leu Arg Asp Tyr Ile Pro Arg Ile Leu Gly Pro<br>445                    450                    455                    460 | 1452 |
| GAG GCC TTC CAG CAG TAC GTG GGT CCC TAT GAA GGC TAT GAC TCC ACC<br>Glu Ala Phe Gln Gln Tyr Val Gly Pro Tyr Glu Gly Tyr Asp Ser Thr<br>                    465                    470                    475 | 1500 |
| GCC AAC CCC ACT GTG TCC AAC GTG TTC TCC ACA GCC GCC TTC CGC TTC<br>Ala Asn Pro Thr Val Ser Asn Val Phe Ser Thr Ala Ala Phe Arg Phe<br>                    480                    485                    490 | 1548 |
| GGC CAT GCC ACG ATC CAC CCG CTG GTG AGG AGG CTG GAC GCC AGC TTC<br>Gly His Ala Thr Ile His Pro Leu Val Arg Arg Leu Asp Ala Ser Phe<br>              495                    500                    505 | 1596 |
| CAG GAG CAC CCC GAC CTG CCC GGG CTG TGG CTG CAC CAG GCT TTC TTC<br>Gln Glu His Pro Asp Leu Pro Gly Leu Trp Leu His Gln Ala Phe Phe<br>510                    515                    520 | 1644 |
| AGC CCA TGG ACA TTA CTC CGT GGA GGT GGT TTG GAC CCA CTA ATA CGA<br>Ser Pro Trp Thr Leu Leu Arg Gly Gly Gly Leu Asp Pro Leu Ile Arg<br>525                    530                    535                    540 | 1692 |
| GGC CTT CTT GCA AGA CCA GCC AAA CTG CAG GTG CAG GAT CAG CTG ATG<br>Gly Leu Leu Ala Arg Pro Ala Lys Leu Gln Val Gln Asp Gln Leu Met<br>                    545                    550                    555 | 1740 |
| AAC GAG GAG CTG ACG GAA AGG CTC TTT GTG CTG TCC AAT TCC AGC ACC<br>Asn Glu Glu Leu Thr Glu Arg Leu Phe Val Leu Ser Asn Ser Ser Thr<br>                    560                    565                    570 | 1788 |
| TTG GAT CTG GCG TCC ATC AAC CTG CAG AGG GGC CGG GAC CAC GGG CTG<br>Leu Asp Leu Ala Ser Ile Asn Leu Gln Arg Gly Arg Asp His Gly Leu<br>              575                    580                    585 | 1836 |
| CCA GGT TAC AAT GAG TGG AGG GAG TTC TGC GGC CTG CCT CGC CTG GAG<br>Pro Gly Tyr Asn Glu Trp Arg Glu Phe Cys Gly Leu Pro Arg Leu Glu<br>590                    595                    600 | 1884 |

-continued

| | |
|---|---|
| ACC CCC GCT GAC CTG AGC ACA GCC ATC GCC AGC AGG AGC GTG GCC GAC<br>Thr Pro Ala Asp Leu Ser Thr Ala Ile Ala Ser Arg Ser Val Ala Asp<br>605                         610                      615                    620 | 1932 |
| AAG ATC CTG GAC TTG TAC AAG CAT CCT GAC AAC ATC GAT GTC TGG CTG<br>Lys Ile Leu Asp Leu Tyr Lys His Pro Asp Asn Ile Asp Val Trp Leu<br>                      625                      630                    635 | 1980 |
| GGA GGC TTA GCT GAA AAC TTC CTC CCC AGG GCT CGG ACA GGG CCC CTG<br>Gly Gly Leu Ala Glu Asn Phe Leu Pro Arg Ala Arg Thr Gly Pro Leu<br>              640                      645                    650 | 2028 |
| TTT GCC TGT CTC ATT GGG AAG CAG ATG AAG GCT CTG CGG GAT GGT GAC<br>Phe Ala Cys Leu Ile Gly Lys Gln Met Lys Ala Leu Arg Asp Gly Asp<br>            655                      660                    665 | 2076 |
| TGG TTT TGG TGG GAG AAC AGC CAC GTC TTC ACG GAT GCA CAG AGG CGT<br>Trp Phe Trp Trp Glu Asn Ser His Val Phe Thr Asp Ala Gln Arg Arg<br>670                         675                      680 | 2124 |
| GAG CTG GAG AAG CAC TCC CTG TCT CGG GTC ATC TGT GAC AAC ACT GGC<br>Glu Leu Glu Lys His Ser Leu Ser Arg Val Ile Cys Asp Asn Thr Gly<br>685                         690                    695                    700 | 2172 |
| CTC ACC AGG GTG CCC ATG GAT GCC TTC CAA GTC GGC AAA TTC CCT GAA<br>Leu Thr Arg Val Pro Met Asp Ala Phe Gln Val Gly Lys Phe Pro Glu<br>                      705                      710                    715 | 2220 |
| GAC TTT GAG TCT TGT GAC AGC ATC CCT GGC ATG AAC CTG GAG GCC TGG<br>Asp Phe Glu Ser Cys Asp Ser Ile Pro Gly Met Asn Leu Glu Ala Trp<br>        720                      725                    730 | 2268 |
| AGG GAA ACC TTT CCT CAA GAC GAC AAG TGT GGC TTC CCA GAG AGC GTG<br>Arg Glu Thr Phe Pro Gln Asp Asp Lys Cys Gly Phe Pro Glu Ser Val<br>            735                      740                    745 | 2316 |
| GAG AAT GGG GAC TTT GTG CAC TGT GAG GAG TCT GGG AGG CGC GTG CTG<br>Glu Asn Gly Asp Phe Val His Cys Glu Glu Ser Gly Arg Arg Val Leu<br>        750                      755                    760 | 2364 |
| GTG TAT TCC TGC CGG CAC GGG TAT GAG CTC CAA GGC CGG GAG CAG CTC<br>Val Tyr Ser Cys Arg His Gly Tyr Glu Leu Gln Gly Arg Glu Gln Leu<br>765                       770                    775                  780 | 2412 |
| ACT TGC ACC CAG GAA GGA TGG GAT TTC CAG CCT CCC CTC TGC AAA GAT<br>Thr Cys Thr Gln Glu Gly Trp Asp Phe Gln Pro Pro Leu Cys Lys Asp<br>                785                      790                    795 | 2460 |
| GTG AAC GAG TGT GCA GAC GGT GCC CAC CCC CCC TGC CAC GCC TCT GCG<br>Val Asn Glu Cys Ala Asp Gly Ala His Pro Pro Cys His Ala Ser Ala<br>        800                      805                    810 | 2508 |
| AGG TGC AGA AAC ACC AAA GGC GGC TTC CAG TGT CTC TGC GCG GAC CCC<br>Arg Cys Arg Asn Thr Lys Gly Gly Phe Gln Cys Leu Cys Ala Asp Pro<br>815                       820                    825 | 2556 |
| TAC GAG TTA GGA GAC GAT GGG AGA ACC TGC GTA GAC TCC GGG AGG CTC<br>Tyr Glu Leu Gly Asp Asp Gly Arg Thr Cys Val Asp Ser Gly Arg Leu<br>830                       835                    840 | 2604 |
| CCT CGG GCG ACT TGG ATC TCC ATG TCG CTG GCT GCT CTG CTG ATC GGA<br>Pro Arg Ala Thr Trp Ile Ser Met Ser Leu Ala Ala Leu Leu Ile Gly<br>845                       850                    855                    860 | 2652 |
| GGC TTC GCA GGT CTC ACC TCG ACG GTG ATT TGC AGG TGG ACA CGC ACT<br>Gly Phe Ala Gly Leu Thr Ser Thr Val Ile Cys Arg Trp Thr Arg Thr<br>                      865                      870                    875 | 2700 |
| GGC ACT AAA TCC ACA CTG CCC ATC TCG GAG ACA GGC GGA GGA ACT CCC<br>Gly Thr Lys Ser Thr Leu Pro Ile Ser Glu Thr Gly Gly Gly Thr Pro<br>        880                      885                    890 | 2748 |
| GAG CTG AGA TGC GGA AAG CAC CAG GCC GTA GGG ACC TCA CCG CAG CGG<br>Glu Leu Arg Cys Gly Lys His Gln Ala Val Gly Thr Ser Pro Gln Arg<br>        895                      900                    905 | 2796 |
| GCC GCA GCT CAG GAC TCG GAG CAG GAG AGT GCT GGG ATG GAA GGC CGG<br>Ala Ala Ala Gln Asp Ser Glu Gln Glu Ser Ala Gly Met Glu Gly Arg<br>910                       915                    920 | 2844 |

```
GAT ACT CAC AGG CTG CCG AGA GCC CTC TGAGGGCAAA GTGGCAGGAC          2891
Asp Thr His Arg Leu Pro Arg Ala Leu
925                 930

ACTGCAGAAC AGCTTCATGT TCCCAAAATC ACCGTACGAC TCTTTTCCAA ACACAGGCAA  2951

ATCGGAAATC AGCAGGACGA CTGTTTTCCC AACACGGGTA AATCTAGTAC CATGTCGTAG  3011

TTACTCTCAG GCATGGATGA ATAAATGTTA TAGCTGC                          3048
```

(2) INFORMATION FOR SEQ ID NO:3:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Asn Glu Trp Arg Glu Phe Cys Gly Leu Pro Arg Leu Glu Thr Pro Ala
1               5                   10                  15
Asp Leu Ser Thr Ala Ile
            20
```

(2) INFORMATION FOR SEQ ID NO:4:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Asn Ala Trp Arg Arg Phe Cys Gly Leu Pro Gln Pro Glu Thr Val Gly
1               5                   10                  15
Gln Leu Gln Thr Val Leu
            20
```

(2) INFORMATION FOR SEQ ID NO:5:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Asn Ser Trp Arg Gly Phe Cys Gly Leu Ser Gln Pro Lys Thr Leu Lys
1               5                   10                  15
Gly Leu Gln Thr Val Leu
            20
```

(2) INFORMATION FOR SEQ ID NO:6:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Asn Glu Trp Arg Glu Phe Cys Gly Leu Pro Arg Leu Glu Thr Pro Ala
1               5                   10                  15

Asp Leu Ser Thr Ala Ile
            20
```

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Asn Glu Trp Arg Glu Phe Cys Gly Leu Ser Arg Leu Glu Thr Trp Ala
1               5                   10                  15

Asp Leu Ser Ala Ala Thr
            20
```

(2) INFORMATION FOR SEQ ID NO:8:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Asn Glu Trp Arg Glu Phe Cys Gly Leu Ser Arg Leu Asp Thr Gly Ala
1               5                   10                  15

Glu Leu Asn Lys Ala Thr
            20
```

(2) INFORMATION FOR SEQ ID NO:9:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Asn Glu Trp Arg Glu Phe Cys Gly Leu Ser Arg Leu Glu Thr Pro Ala
1               5                   10                  15

Glu Leu Asn Lys Ala Ile
            20
```

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Ile Glu Gly Arg Ile Ser Glu Phe
            5
```

(2) INFORMATION FOR SEQ ID NO:11:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:11:

CGATTAGGTA GGTAGT    16

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:12:

AATTCGACCT GCCC    14

(2) INFORMATION FOR SEQ ID NO:13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:13:

GGGCTGTAGT    10